US007550559B2

(12) United States Patent
Sannigrahi et al.

(10) Patent No.: US 7,550,559 B2
(45) Date of Patent: Jun. 23, 2009

(54) ACYLSULFONAMIDE COMPOUNDS AS INHIBITORS OF HEPATITIS C VIRUS NS3 SERINE PROTEASE

(75) Inventors: Mousumi Sannigrahi, Summit, NJ (US); F. George Njoroge, Warren, NJ (US); Viyyoor M. Girijavallabhan, Parsippany, NJ (US)

(73) Assignee: Schering Corporation, Kenilworth, NJ (US)

( * ) Notice: Subject to any disclaimer, the term of this patent is extended or adjusted under 35 U.S.C. 154(b) by 302 days.

(21) Appl. No.: 11/211,771

(22) Filed: Aug. 25, 2005

(65) Prior Publication Data

US 2006/0046956 A1 Mar. 2, 2006

Related U.S. Application Data

(60) Provisional application No. 60/605,234, filed on Aug. 27, 2004.

(51) Int. Cl.
*C07K 5/08* (2006.01)
(52) U.S. Cl. .......................... 530/331; 514/18; 514/19; 548/535
(58) Field of Classification Search .................. 514/19, 514/18; 530/331
See application file for complete search history.

(56) References Cited

U.S. PATENT DOCUMENTS

| 5,712,145 | A | 1/1998 | Houghton et al. | |
|---|---|---|---|---|
| 6,608,027 | B1 | 8/2003 | Tsantrizos et al. | |
| 6,995,174 | B2 * | 2/2006 | Wang et al. | 514/312 |

FOREIGN PATENT DOCUMENTS

| EP | 0 381 216 B1 | 12/1995 |
|---|---|---|
| WO | WO 89/04669 | 6/1989 |
| WO | WO 98/14181 | 4/1998 |
| WO | WO 98/17679 | 4/1998 |
| WO | WO 98/22496 | 5/1998 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 01/74768 A | 10/2001 |
| WO | WO 01/74768 A2 | 10/2001 |
| WO | WO 01/77113 A2 | 10/2001 |
| WO | WO 01/81325 A2 | 11/2001 |
| WO | WO 02/08187 A1 | 1/2002 |
| WO | WO 02/08198 A2 | 1/2002 |
| WO | WO 02/08244 A2 | 1/2002 |
| WO | WO 02/08251 A2 | 1/2002 |
| WO | WO 02/08256 A2 | 1/2002 |
| WO | WO 02/48172 A2 | 6/2002 |
| WO | WO 02/060926 A2 | 8/2002 |
| WO | WO 2005/021584 A | 3/2005 |

OTHER PUBLICATIONS

International Search Report for International Application No. PCT/US2005/030249 mailed Feb. 3, 2006—4pgs.
Berenguer, Marina, et al., "Hepatitis B and C . . . ," Proceedings of the Association of American Physicians 110(2):98-112 (1998).
Dimasi, Nazzareno, et al., "Characterization of Engineered . . . ," Journal of Virology 71(10):7461-69 (1997).
Elzouki, Abdul-Nasser, et al., "Serine protease inhibitors . . . ," Journal of Hepatology 27:42-48 (1997).
Failla, Cristina Maria, et al., "Redesigning the substrate . . . ," Folding & Design 1(1):35-42 (Jan. 10, 1996).
Han, Wei, et al., "alpha-Ketoamides, alpha-Ketoesters . . . ," Bioorganic & Medicinal Chemistry Letters 10:711-713 (2000).
Hoofnagle, Jay H., et al., "The Treatment of . . . ," Drug Therapy 336(5):347-56 (1997).
Ingallinella, Paolo, et al., "Potent Peptide Inhibitors . . . ," Biochemistry 37:8906-14 (1998).
Johansson, Anja, et al., "Tetrapeptides as Potent . . . ," Bioorganic & Medicinal Chemistry 3915-3922 (2002).
Johansson, Anja, et al., "Acyl Sulfonamides as Potent . . . ," Bioorganic & Medicinal Chemistry 11:2551-68 (2003).
Kolykhalov, Alexander A., et al., "Specificy of the Hepatitis . . . ," Journal of Virology 68(11):7525-7533 (Nov. 1994).
Komoda, Yasumasa, et al., "Substrate Requirements of Hepatitis C . . . ," Journal of Virology 68(11)7351-7 (Nov. 1994).
Landro, James A., et al., "Mechanistic Role of . . . ," Biochemistry 36:9340-8 (1997).
Llinas-Brunet, Montse, et al., "Peptide-Based Inhibitors . . . ," Bioorganic & Medicinal Chemistry Letters 8:1713-1718 (1998).
Marchetti, Antonella, et al., "Synthesis of Two Novel . . . ," Synlett S1:1000-1002 (1999).
Martin, F., et al., "Affinity selection of a . . . ," Protein Engineering 10(5):607-14 (1997).
Martin, Franck, et al., "Design of Selective . . . ," Biochemistry 37:11459-68 (1998).
Pizzi, Elisabetta, et al., "Molecular model of . . . ," Proc. Natl. Acad. Sci. USA 91:888-892 (Feb. 1994).
BioWorld Today 9(217):4 (Nov. 10, 1998).
U.S. Appl. No. 10/052,386, filed Jan. 18, 2002.

* cited by examiner

*Primary Examiner*—David Lukton
(74) *Attorney, Agent, or Firm*—Palaiyur S. Kalyanaraman; Serena Farquharson-Torres

(57) ABSTRACT

The present invention discloses novel compounds which have HCV protease inhibitory activity as well as methods for preparing such compounds. In another embodiment, the invention discloses pharmaceutical compositions comprising such compounds as well as methods of using them to treat disorders associated with the HCV protease.

57 Claims, No Drawings

```
                         SEQUENCE LISTING

<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: substrate derived from P side of NS5A-NS5B
      junction sequence
<220> FEATURE:
<221> NAME/KEY: MISC_FEATURE
<222> LOCATION: (7)..(7)
<223> OTHER INFORMATION: Alanine or Proline
<220> FEATURE:
<221> NAME/KEY: MISC_FEATURE
<222> LOCATION: (8)..(8)
<223> OTHER INFORMATION: Norvaline

<400> SEQUENCE: 1

Asp Thr Glu Asp Val Val Xaa Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: competitive inhibitor
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: gamma-carboxyglutamic acid
<222> LOCATION: (2)..(2)
<220> FEATURE:
<221> NAME/KEY: cyclohexylalanine
<222> LOCATION: (5)..(5)

<400> SEQUENCE: 2

Asp Xaa Leu Ile Xaa Cys
1               5

<210> SEQ ID NO 3
<211> LENGTH: 8
<212> TYPE: PRT
<213> ORGANISM: Artificial Sequence
<220> FEATURE:
<223> OTHER INFORMATION: competitive inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (8)..(8)
<223> OTHER INFORMATION: Norvaline

<400> SEQUENCE: 3

Asp Thr Glu Asp Val Val Ala Xaa
1               5

<210> SEQ ID NO 4
<211> LENGTH: 8
<212> TYPE: PRT
<213> ORGANISM: Artificial Sequence
<220> FEATURE:
<223> OTHER INFORMATION: competitive inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (8)..(8)
<223> OTHER INFORMATION: Norvaline

<400> SEQUENCE: 4

Asp Thr Glu Asp Val Val Pro Xaa
1               5
```

ACYLSULFONAMIDE COMPOUNDS AS INHIBITORS OF HEPATITIS C VIRUS NS3 SERINE PROTEASE

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention additionally discloses novel compounds containing acylsulfonamide P1' moieties as inhibitors of the HCV NS3/NS4a serine protease. This application claims priority from U.S. provisional patent application Ser. No. 60/605,234, filed Aug. 27, 2004.

FIELD OF THE INVENTION

Background of the Invention

Hepatitis C virus (HCV) is a (+)-sense single-stranded RNA virus that has been implicated as the major causative agent in non-A, non-B hepatitis (NANBH), particularly in blood-associated NANBH (BB-NANBH) (see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

Recently, an HCV protease necessary for polypeptide processing and viral replication has been identified, cloned and expressed. (See, e.g. U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy. The inventive compounds can inhibit such protease. They also can modulate the processing of hepatitis C virus (HCV) polypeptide.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e. trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) *Proc. Natl. Acad. Sci (USA)* 91:888-892, Failla et al. (1996) *Folding & Design* 1:35-42. The NS3/NS4a cleavage site is also more tolerant of mutagenesis than the other sites. See, e.g., Kollykhalov et al. (1994) *J. Virol.* 68:7525-7533. It has also been found that acidic residues in the region upstream of the cleavage site are required for efficient cleavage. See, e.g., Komoda et al. (1994) *J. Virol.* 68:7351-7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) *Biochem.* 36:9340-9348, Ingallinella et al. (1998) *Biochem.* 37:8906-8914, Llinàs-Brunet et al. (1998) *Bioorg. Med. Chem. Lett.* 8:1713-1718), inhibitors based on the 70-amino acid polypeptide eglin c (Martin et al. (1998) *Biochem.* 37:11459-11468, inhibitors affinity selected from human pancreatic secretory trypsin inhibitor (hPSTI-C3) and minibody repertoires (MBip) (Dimasi et al. (1997) *J. Virol.* 71:7461-7469), $cV_HE2$ (a "camelized" variable domain antibody fragment) (Martin et al. (1997) *Protein Eng.* 10:607-614), and α1-antichymotrypsin (ACT) (Elzouki et al.) (1997) *J. Hepat.* 27:42-28). A ribozyme designed to selectively destroy hepatitis C virus RNA has recently been disclosed (see, *BioWorld Today* 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

Reference is made to WO 00/59929 (U.S. Pat. No. 6,608, 027, Assignee: Boehringer Ingelheim (Canada) Ltd.; Published Oct. 12, 2000) which discloses peptide derivatives of the formula:

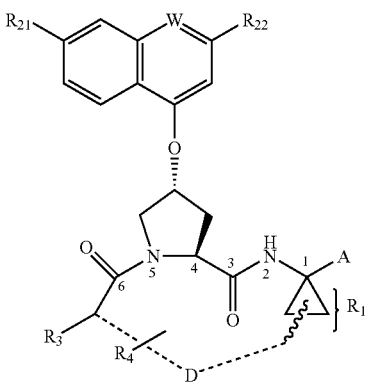

Reference is made to A. Marchetti et al, *Synlett*, S1, 1000-1002 (1999) describing the synthesis of bicylic analogs of an inhibitor of HCV NS3 protease. A compound disclosed therein has the formula:

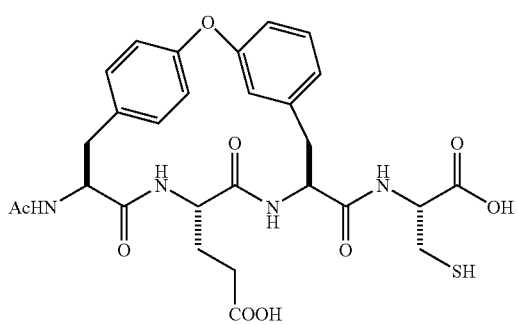

Reference is also made to W. Han et al, *Bioorganic & Medicinal Chem. Lett*, (2000) 10, 711-713, which describes the preparation of certain α-ketoamides, α-ketoesters and α-diketones containing allyl and ethyl functionalities.

Reference is also made to WO 00/09558 (Assignee: Boehringer Ingelheim Limited; Published Feb. 24, 2000) which discloses peptide derivatives of the formula:

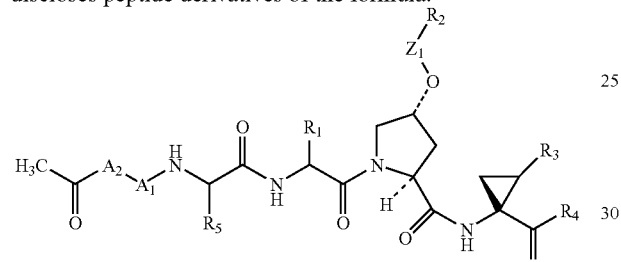

where the various elements are defined therein. An illustrative compound of that series is:

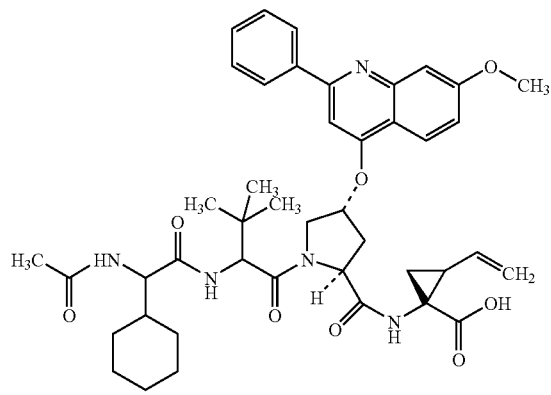

Reference is also made to WO 00/09543 (Assignee: Boehringer Ingelheim Limited; Published Feb. 24, 2000) which discloses peptide derivatives of the formula:

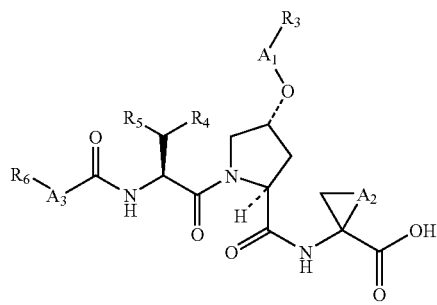

where the various elements are defined therein. An illustrative compound of that series is:

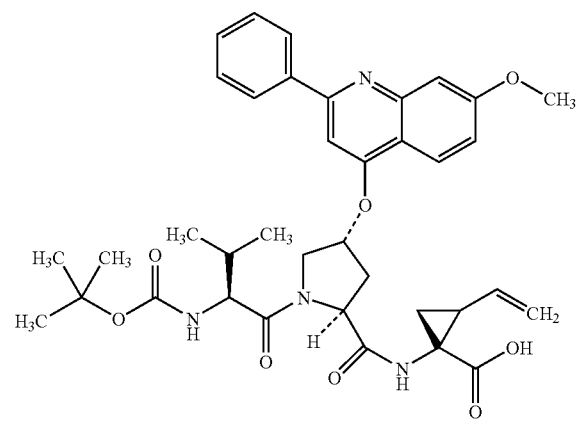

Reference is also made to WO02/060926 (Bristol-Myers Squibb Company; published Aug. 8, 2002) which discloses compounds of the formula:

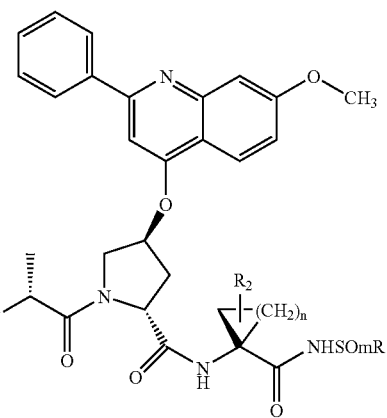

An illustrative compound from the WO02/060926 publication is:

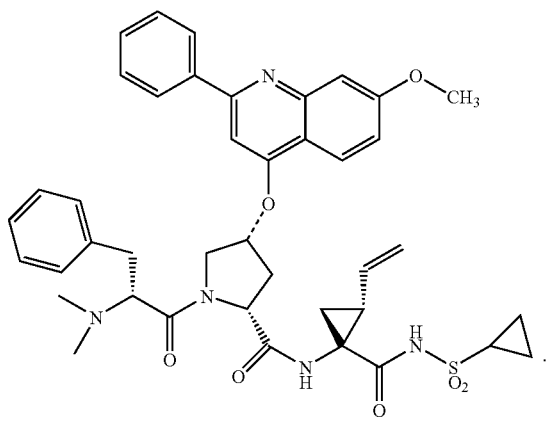

Reference is also made to A. Johansson et al, *Bioorg. and Med. Chem.*, 3915-3922 (2002) and A. Johansson et al, Bioorg. and Med. Chem., 2551-2568 (2003) which disclose certain acyl sulfonamides and tetrapeptides.

A specific compound disclosed in the afore-mentioned WO 01/74768 has the following formula:

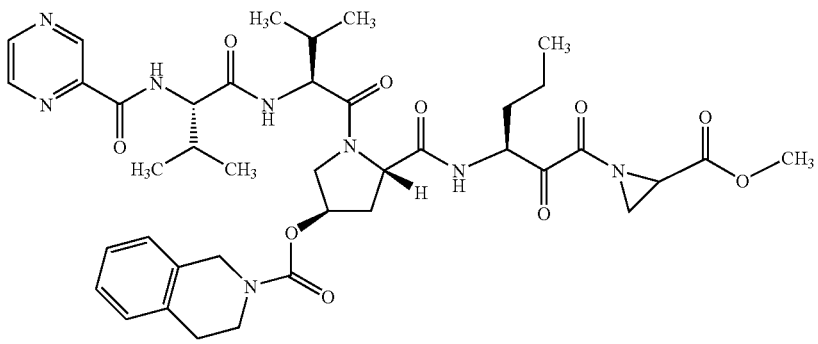

Reference is also made to U.S. Pat. No. 6,608,027 (Boehringer Ingelheim, Canada) which discloses NS3 protease inhibitors of the type:

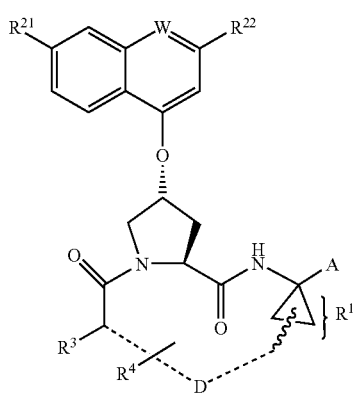

wherein the various moieties are defined therein.

Current therapies for hepatitis C include interferon-α (INF$_\alpha$) and combination therapy with ribavirin and interferon. See, e.g. Beremguer et al. (1998) Proc. Assoc. Am. Physicians 110(2):98-112. These therapies suffer from a low sustained response rate and frequent side effects. See, e.g., Hoofnagle et al. (1997) N. Engl. J. Med. 336:347. Currently, no vaccine is available for HCV infection.

Reference is further made to WO 01/74768 (Assignee: Vertex Pharmaceuticals Inc) published Oct. 11, 2001, which discloses certain compounds of the following general formula (R is defined therein) as NS3-serine protease inhibitors of Hepatitis C virus:

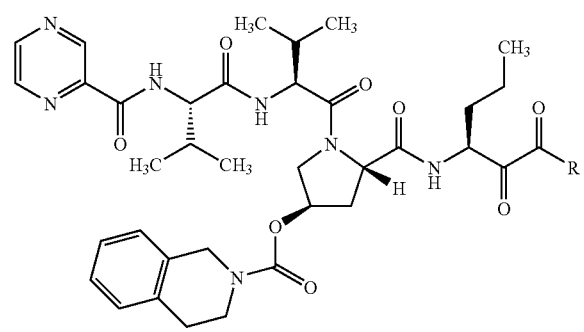

PCT Publications WO 01/77113; WO 01/081325; WO 02/08198; WO 02/08256; WO 02/08187; WO 02/08244; WO 02/48172; WO 02/08251; and pending U.S. patent application Ser. No. 10/052,386, filed Jan. 18, 2002, disclose various types of peptides and/or other compounds as NS-3 serine protease inhibitors of hepatitis C virus. The disclosures of those applications are incorporated herein by reference thereto.

There is a need for new treatments and therapies for HCV infection. There is a need for compounds useful in the treatment or prevention or amelioration of one or more symptoms of hepatitis C.

There is a need for methods of treatment or prevention or amelioration of one or more symptoms of hepatitis C.

There is a need for methods for modulating the activity of serine proteases, particularly the HCV NS3/NS4a serine protease, using the compounds provided herein.

There is a need for methods of modulating the processing of the HCV polypeptide using the compounds provided herein.

SUMMARY OF THE INVENTION

In its many embodiments, the present invention provides a novel class of inhibitors of the HCV protease, pharmaceutical compositions containing one or more of the compounds, methods of preparing pharmaceutical formulations comprising one or more such compounds, and methods of treatment or prevention of HCV or amelioration of one or more of the symptoms of hepatitis C using one or more such compounds or one or more such formulations. Also provided are methods of modulating the interaction of an HCV polypeptide with HCV protease. Among the compounds provided herein, compounds that inhibit HCV NS3/NS4a serine protease activity are preferred. The present invention discloses compounds having the general structure shown in structural Formula I:

Formula I

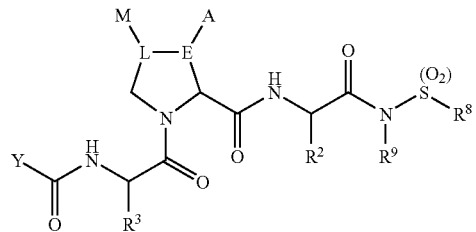

or a pharmaceutically acceptable salt, solvate or ester thereof, wherein:

$R^8$ is selected from the group consisting of alkyl-, aryl-, heteroalkyl-, heteroaryl-, cycloalkyl-, heterocyclyl-, arylalkyl-, heteroarylalkyl-, and heterocyclylalkyl;

$R^9$ is selected from the group consisting of H, alkyl, alkenyl, alkynyl, aryl and cycloalkyl;

A and M can be the same or different, each being independently selected from R, OR, N(H)R, N(RR'), SR, S(O$_2$)R, and halo; or A and M are connected to each other (in other words, A-E-L-M taken together) such that the moiety:

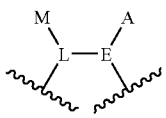

shown above in Formula I forms either a three, four, five, six, seven or eight-membered cycloalkyl, a four to eight-membered heterocyclyl, a six to ten-membered aryl, or a five to ten-membered heteroaryl;

E is C(H) or C(R);

L is C(H), C(R), CH$_2$C(R), or C(R)CH$_2$;

R and R' can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-;

or alternatively R and R' in NRR' are connected to each other such that NRR' forms a four to eight-membered heterocyclyl;

$R^2$ and $R^3$ can be the same or different, each being independently selected from the group consisting of H, alkyl, heteroalkyl, alkenyl, heteroalkenyl, alkynyl, heteroalkynyl, cycloalkyl, spiro-linked cycloalkyl, heterocyclyl, aryl, arylalkyl, heteroaryl, and heteroarylalkyl;

Y is selected from the following moieties:

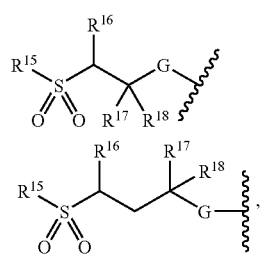

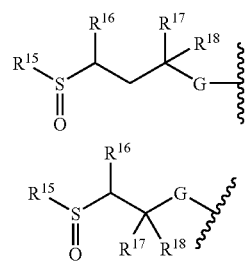

-continued

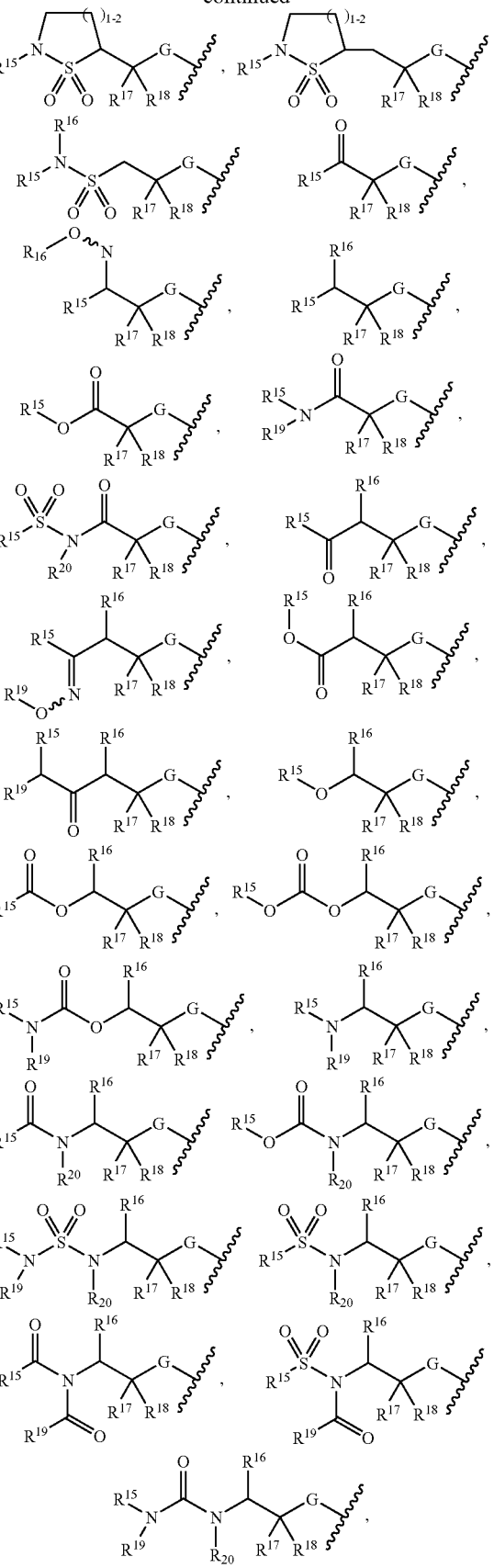

-continued

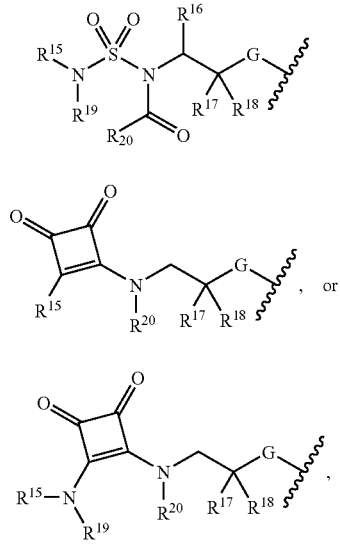

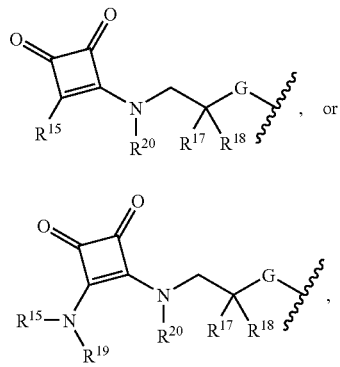

wherein G is NH or O; and $R^{15}$, $R^{16}$, $R^{17}$, $R^{18}$, $R^{19}$, $R^{20}$, $R^{21}$, $R^{22}$, $R^{23}$, $R^{24}$ and $R^{25}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl, spirolinked cycloalkyl, and heterocyclyl can be unsubstituted or optionally independently substituted with one or more moieties independently selected from the group consisting of hydroxy, alkoxy, aryloxy, thio, alkylthio, arylthio, amino, amido, alkylamino, arylamino, alkylsulfonyl, arylsulfonyl, sulfonamido, alkyl, alkenyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

The above-noted statement "A and M are connected to each other such that the moiety:

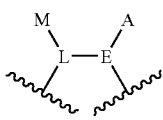

shown above in Formula I forms either a three, four, five, six, seven or eight-membered cycloalkyl, a four to eight-membered heterocyclyl, a six to ten-membered aryl, or a five to ten-membered heteroaryl" can be illustrated in a non-limiting matter as follows. Thus, for example, in the case where A and M are connected such that the moiety:

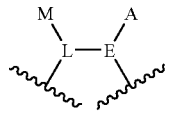

shown above in Formula I forms a six-membered cycloalkyl (cyclohexyl), Formula I can be depicted as:

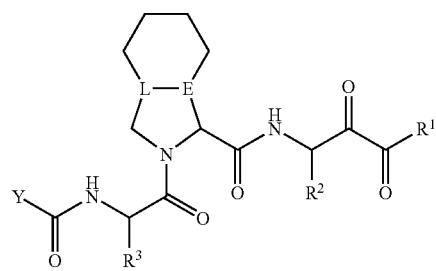

One with ordinary skill in the art will appreciate that similar depictions for Formula I can be arrived at when A and M shown above in the moiety:

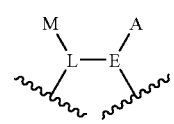

(i.e., M-L-E-A taken together) are connected to form a three, four, five, seven or eight-membered cycloalkyl, a four to eight-membered heterocyclyl, a six to ten-membered aryl, or a five to ten-membered heteroaryl.

The present invention also discloses compounds having the general structure shown in structural Formula II:

Formula II

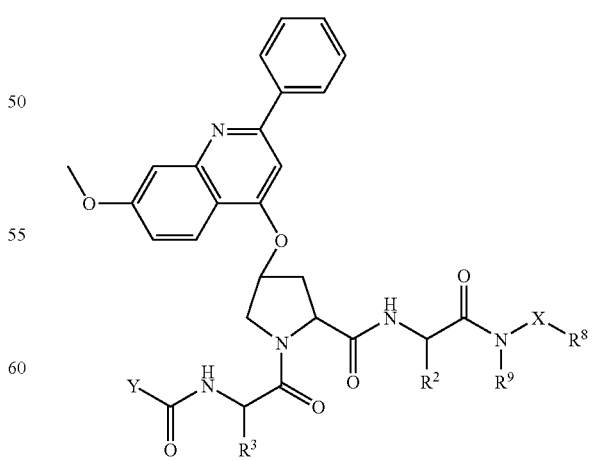

or a pharmaceutically acceptable salt, solvate or ester thereof, wherein:

R[8] is selected from the group consisting of alkyl-, aryl-, heteroalkyl-, heteroaryl-, cycloalkyl-, heterocyclyl-, arylalkyl-, heteroarylalkyl-, spiro-linked cycloalkyl, and heterocyclylalkyl;

R[9] is selected from the group consisting of H, alkyl, alkenyl, alkynyl, aryl and cycloalkyl;

X is S(O) or S(O$_2$);

R[2] is selected from the group consisting of H, alkyl, heteroalkyl, alkenyl, heteroalkenyl, alkynyl, heteroalkynyl, non-spiro-linked cycloalkyl, heterocyclyl, aryl, arylalkyl, heteroaryl, and heteroarylalkyl;

R[3] is selected from the group consisting of H, alkyl, heteroalkyl, alkenyl, heteroalkenyl, alkynyl, heteroalkynyl, cycloalkyl, spiro-linked cycloalkyl, heterocyclyl, aryl, arylalkyl, heteroaryl, and heteroarylalkyl;

Y is selected from the following moieties:

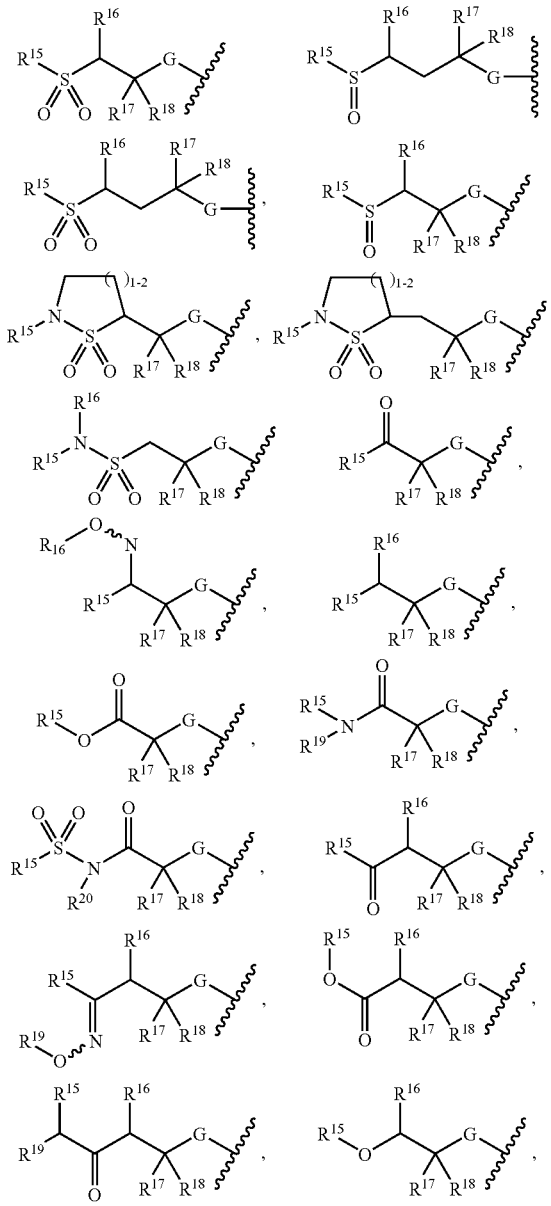
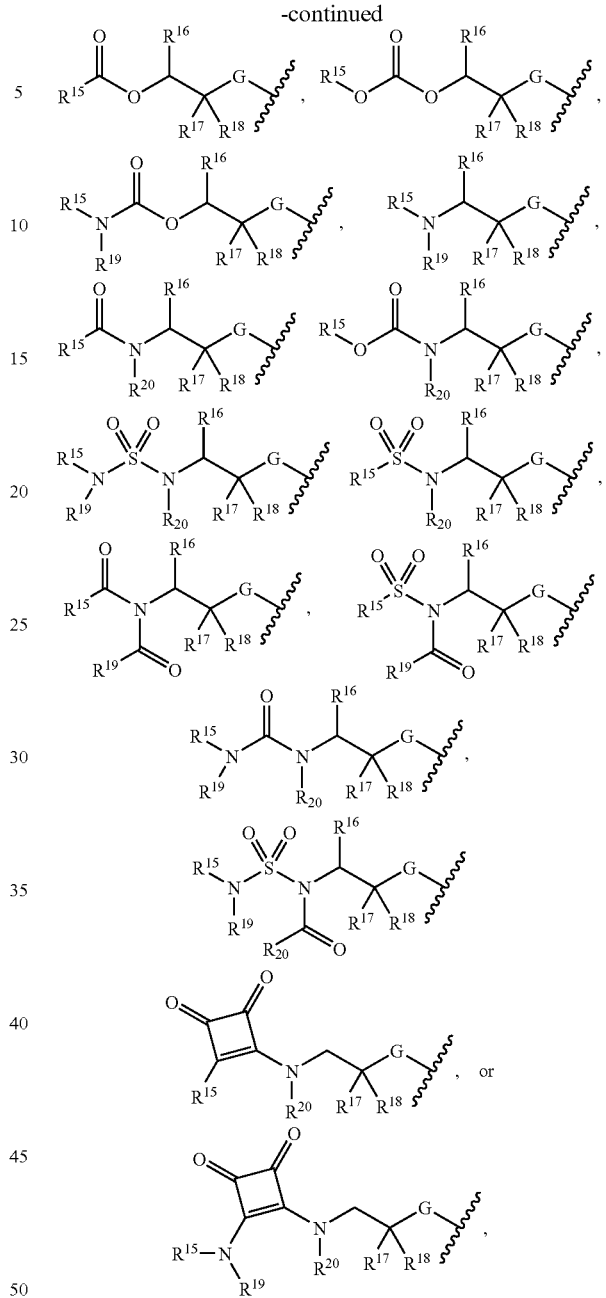

wherein G is NH or O; and R[15], R[16], R[17], R[18], R[19], R[20], and R[21] can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) R[17] and R[18] are independently connected to each other to form a three to eight-membered cycloalkyl or heterocyclyl; (ii) likewise independently R[15] and R[19] are connected to each other to form a four to eight-membered heterocyclyl; (iii) likewise independently R[15] and R[16] are connected to each other to form a four to eight-membered heterocyclyl; and (iv) likewise independently R[15] and R[20] are connected to each other to form a four to eight-membered heterocyclyl;

wherein each of said alkyl, aryl, heteroaryl, cycloalkyl or heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, alkenyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In the above-noted definitions, preferred alkyl is made of one to ten carbon atoms, preferred alkenyl or alkynyl is made of two to ten carbon atoms, preferred cycloalkyl is made of three to eight carbon atoms, and preferred heteroalkyl, heteroaryl or heterocycloalkyl (heterocyclyl) has one to six oxygen, nitrogen, sulfur, or phosphorus atoms. Preferred spiro-linked cycloalkyl is spiro-linked cyclopropyl.

The compounds represented by Formula I or Formula II, by themselves or in combination with one or more other suitable agents disclosed herein, can be useful for treating diseases such as, for example, HCV, HIV, AIDS (Acquired Immune Deficiency Syndrome), and related disorders, as well as for modulating the activity of hepatitis C virus (HCV) protease, preventing HCV, or ameliorating one or more symptoms of hepatitis C. Such modulation, treatment, prevention or amelioration can be done with the inventive compounds as well as with pharmaceutical compositions or formulations comprising such compounds. Without being limited to theory, it is believed that the HCV protease may be the NS3 or NS4a protease. The inventive compounds can inhibit such protease. They can also modulate the processing of hepatitis C virus (HCV) polypeptide.

DETAILED DESCRIPTION

In an embodiment, the present invention discloses compounds which are represented by structural Formula I or II, or a pharmaceutically acceptable salt, solvate or ester thereof, wherein the various moieties are as defined above.

Additional embodiments of the present invention are detailed below in three separate segments: the first one listing the additional embodiments that are applicable to the compounds represented by both Formula I and Formula II, the second one listing the additional embodiments that are applicable to the compounds represented by Formula I only, and the third one listing the additional embodiments that are applicable to the compounds represented by Formula II only.

1. The Following Additional Embodiments Apply to Both the Compound of Formula I and the Compound of Formula II:

In another embodiment, $R^8$ is selected from the group consisting of alkyl-, aryl-, heteroaryl-, cycloalkyl-, arylalkyl- and heteroarylalkyl-.

In another embodiment, $R^8$ is aryl or cycloalkyl.

In another embodiment, $R^8$ is phenyl or cyclopropyl.

In another embodiment, $R^9$ is H, alkyl or cycloalkyl.

In another embodiment, $R^9$ is H, methyl or cyclopropyl.

In another embodiment, $R^2$ is selected from the group consisting of the following moieties:

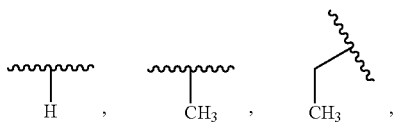

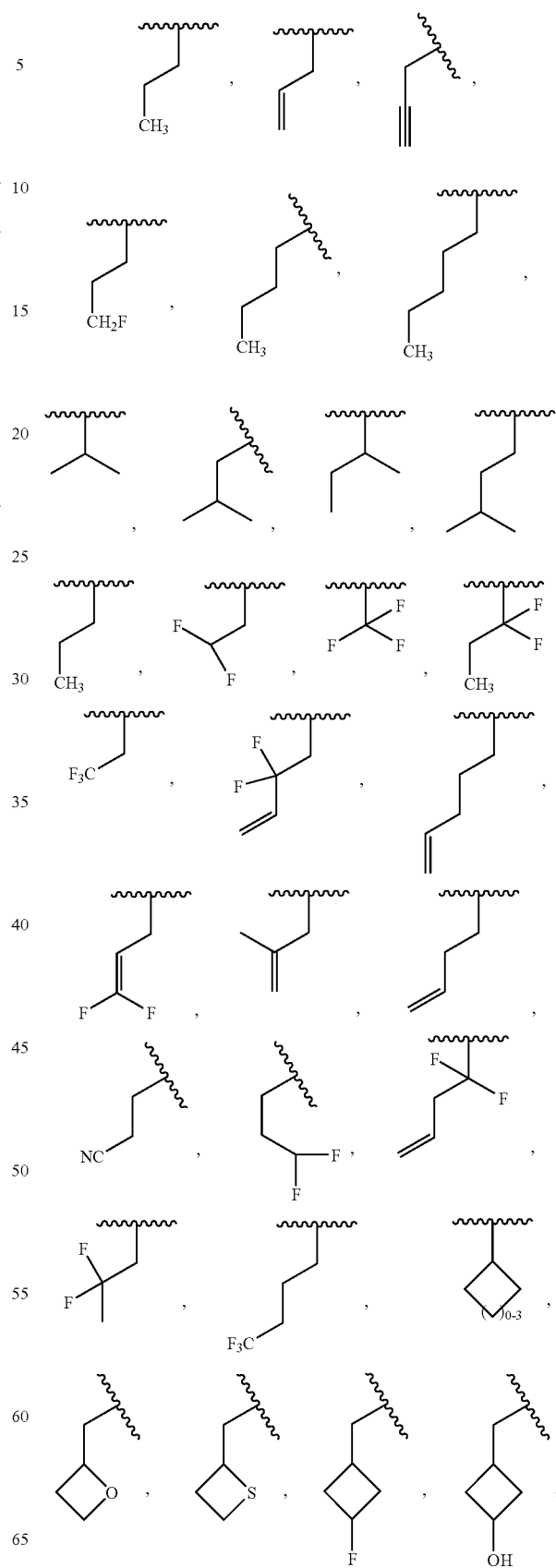

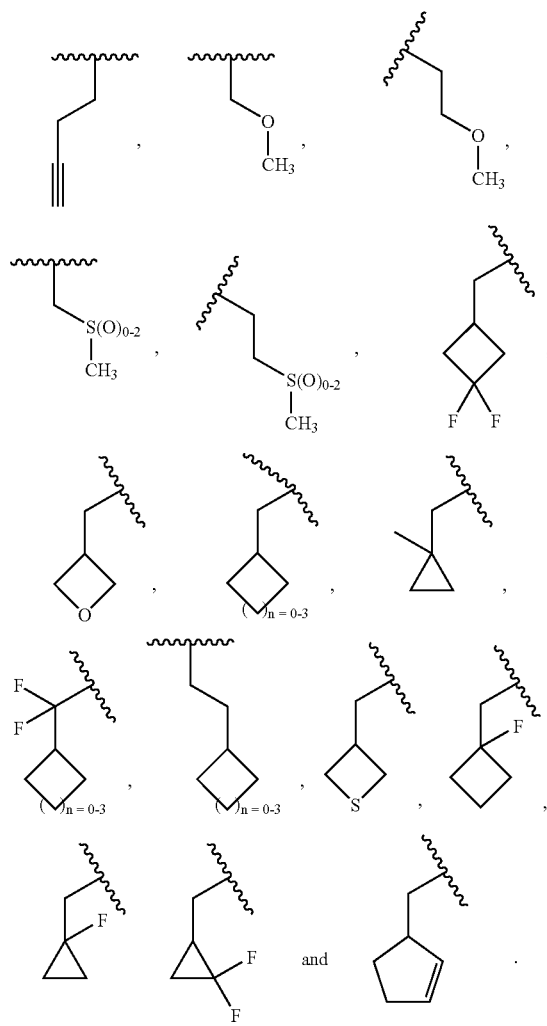
In a further embodiment, $R^3$ is selected from the group consisting of:
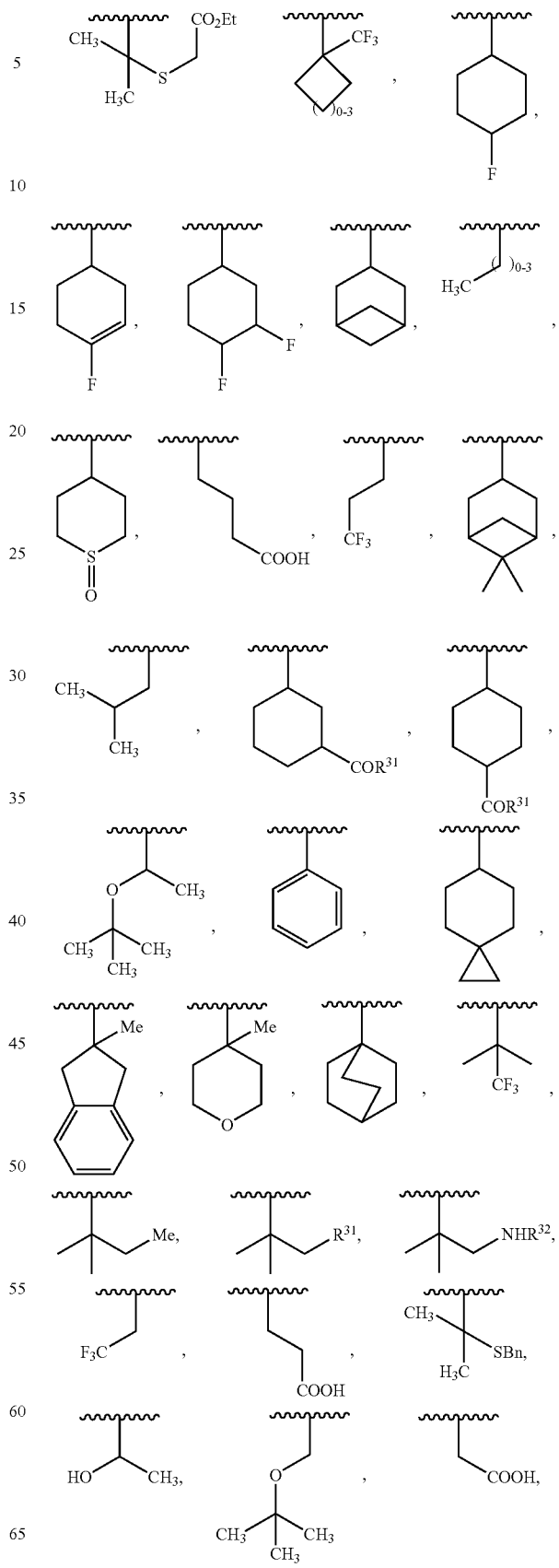

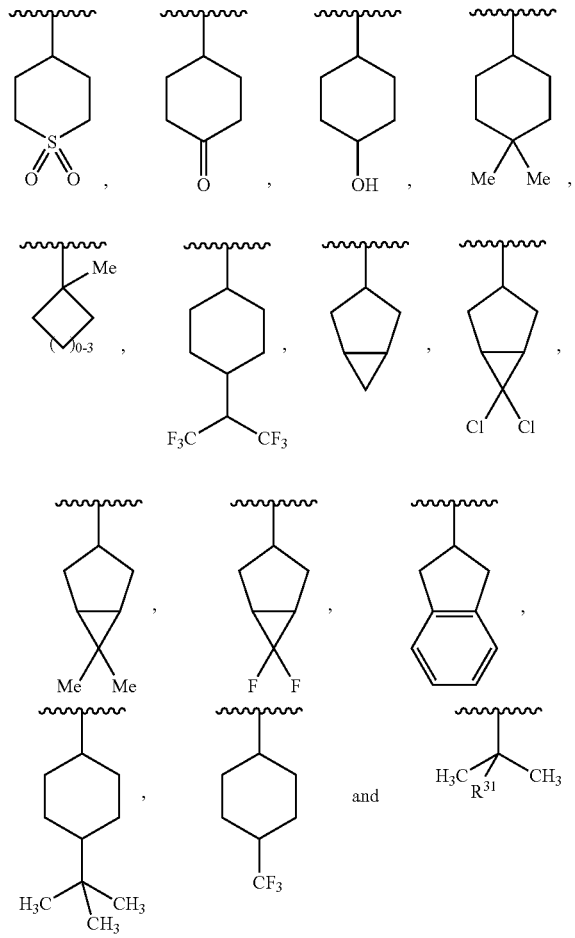
wherein $R^{31}$ is OH or O-alkyl; and
$R^{32}$ is H, C(O)CH$_3$, C(O)OtBu or C(O)N(H)tBu.
In an additional embodiment, $R^3$ is selected from the group consisting of the following moieties:
In yet another embodiment, G is NH.
In a further embodiment, Y is selected from the following moieties:
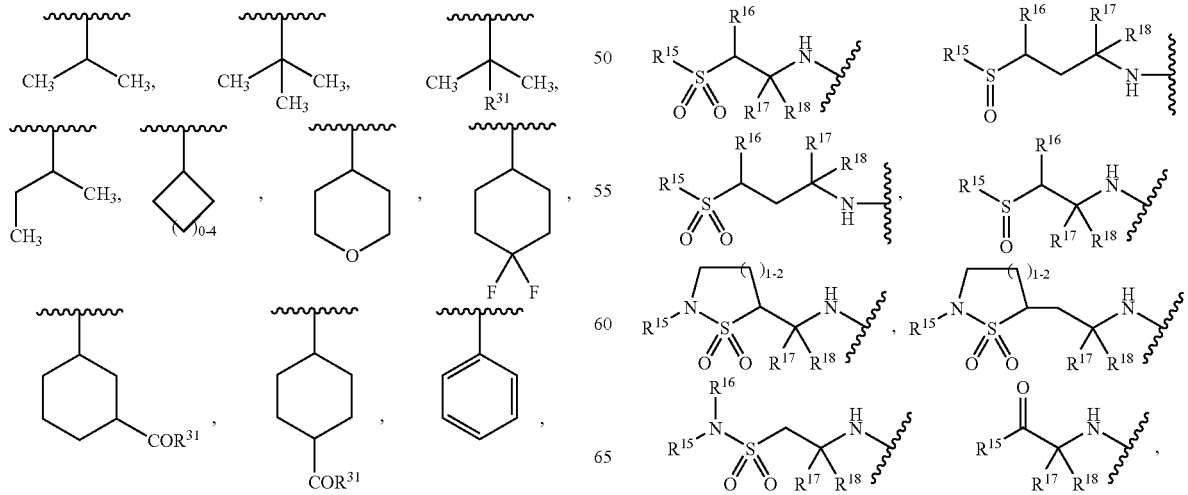

-continued

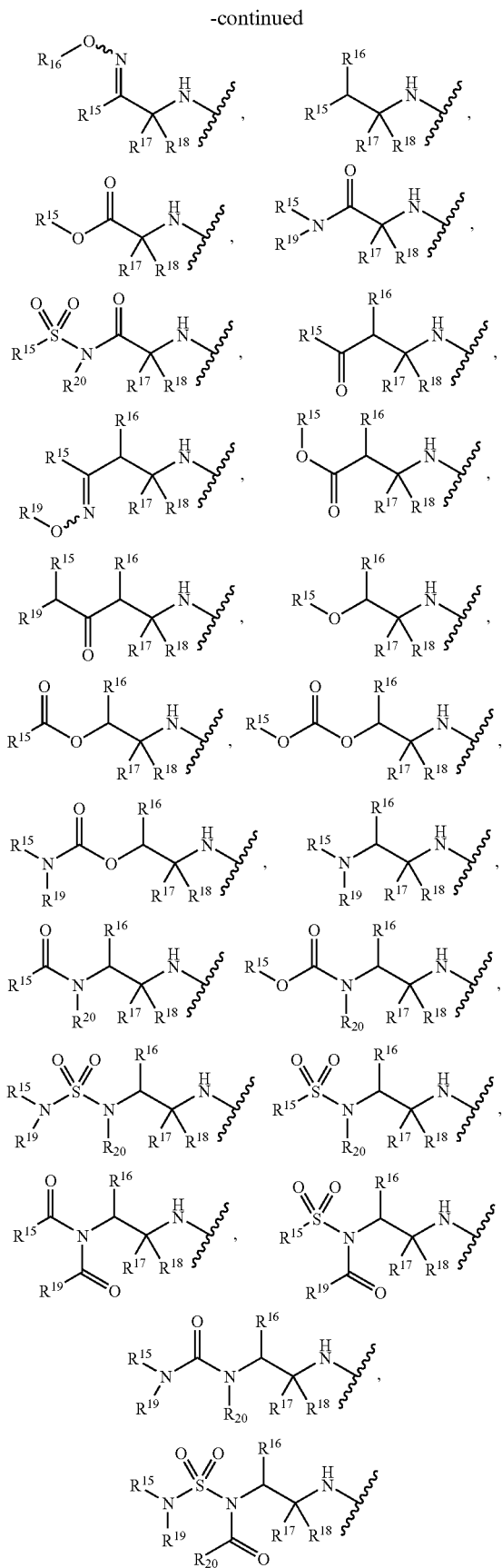

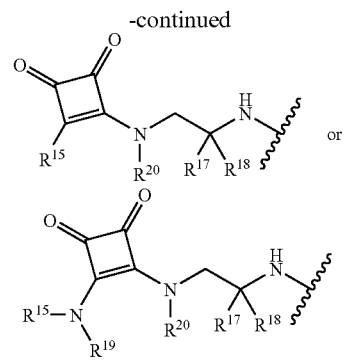

wherein $R^{15}$, $R^{16}$, $R^{17}$, $R^{18}$, $R^{19}$, $R^{20}$, $R^{21}$, $R^{22}$, $R^{23}$, $R^{24}$, and $R^{25}$ each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In a still additional embodiment, the moiety:

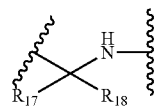

is selected from the following:

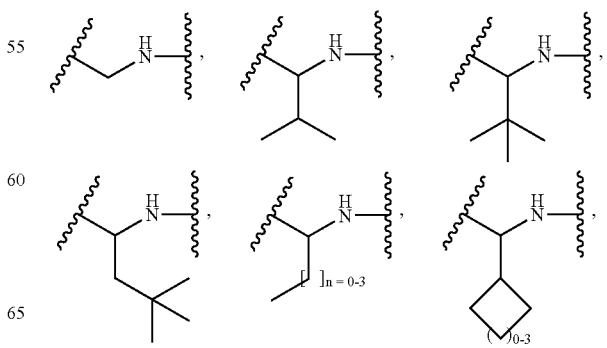

-continued
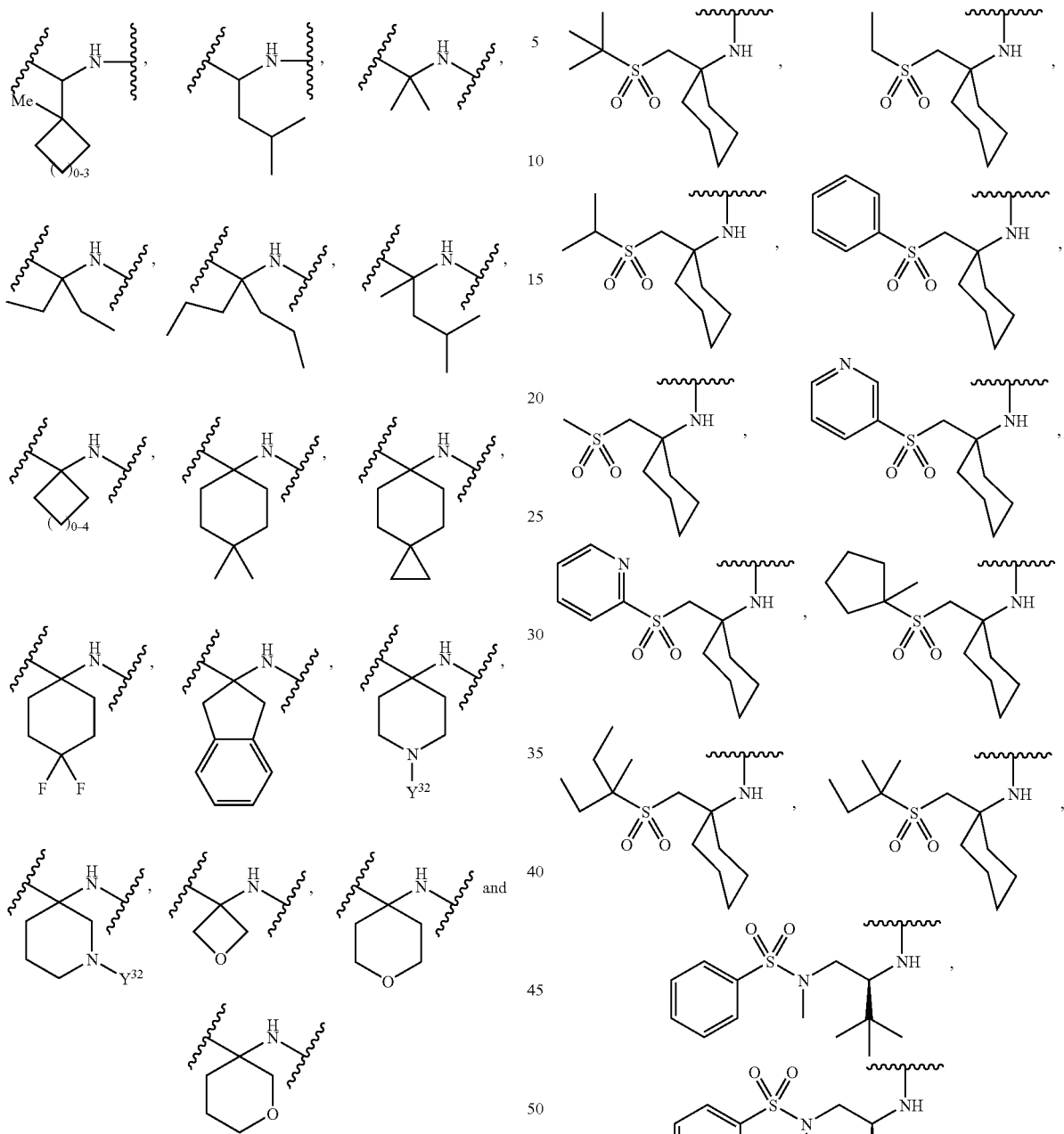
wherein $Y^{32}$ is selected from the group consisting of:
In a further embodiment, Y is selected from:
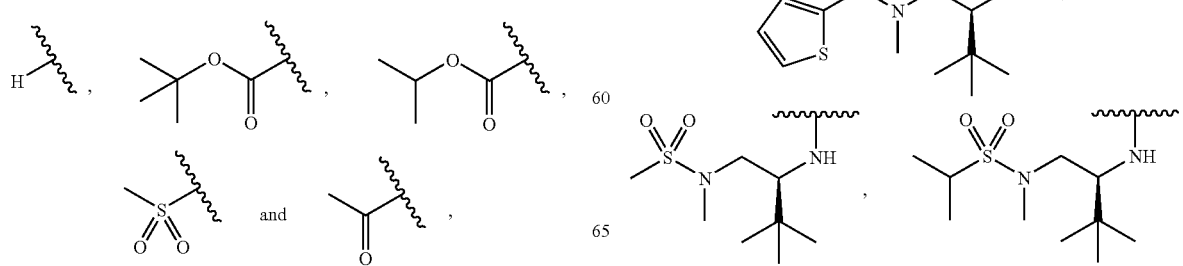

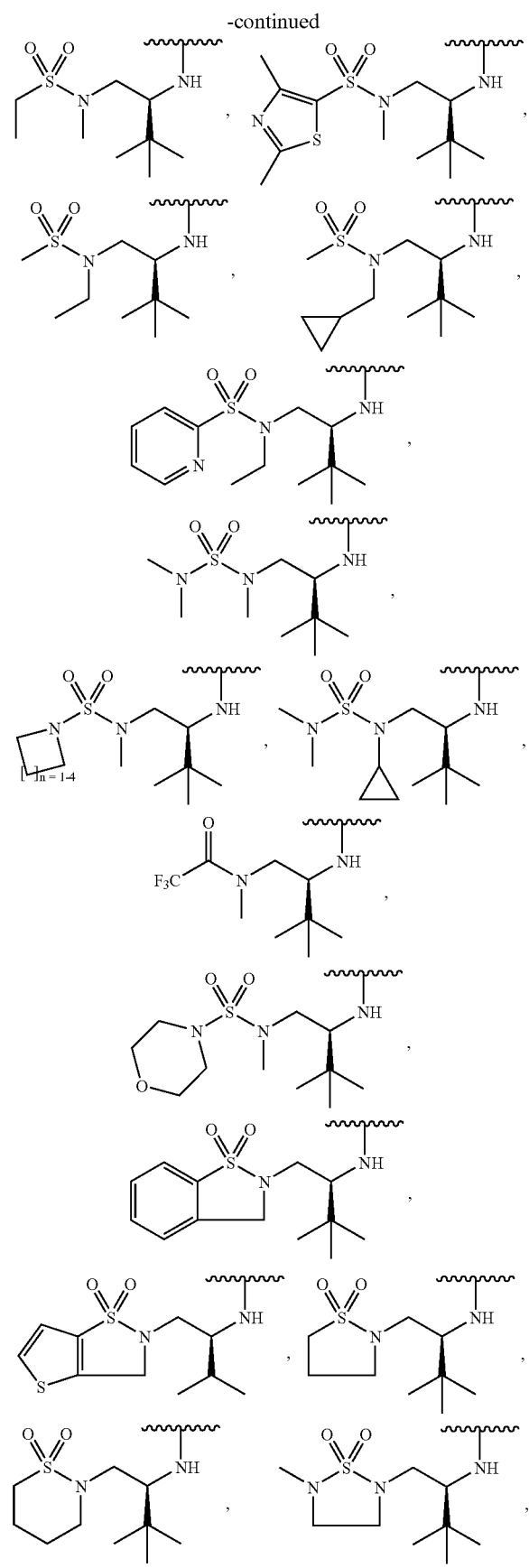

-continued

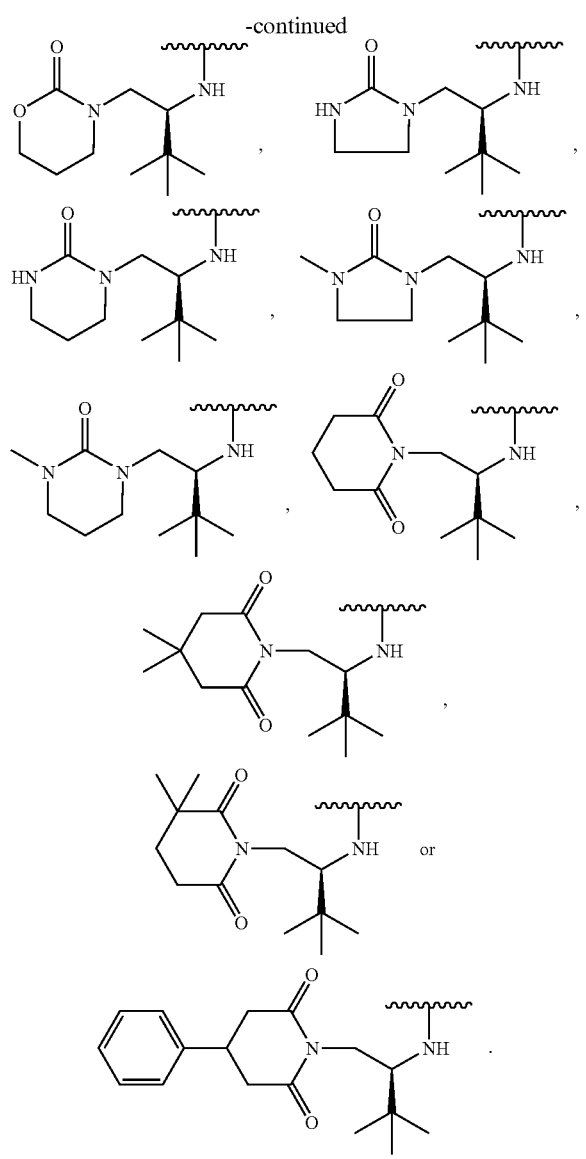

2. The Following Additional Embodiments Apply Specifically and Only to the Compound of Formula I:

In another embodiment, in addition to the earlier-defined embodiments for $R^2$, $R^2$ is selected from the group consisting of:

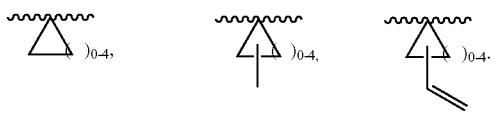

In another embodiment, $R^2$ is selected from the group consisting of:

In another embodiment, $R^8$ is phenyl or cyclopropyl.

In another embodiment, the moiety:

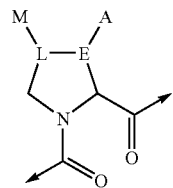

is selected from the following structures:

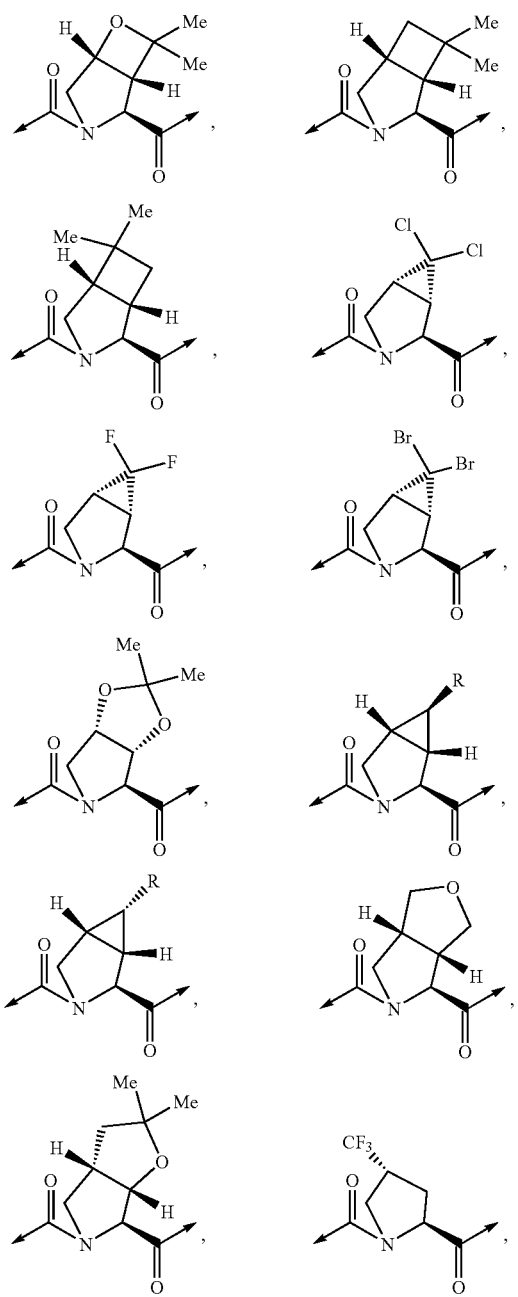

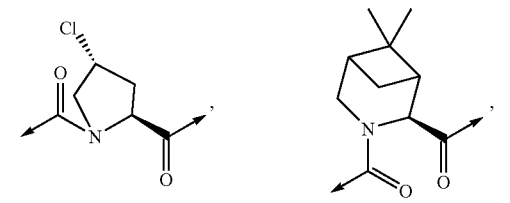
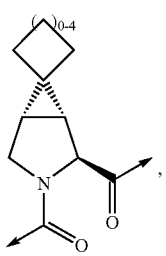
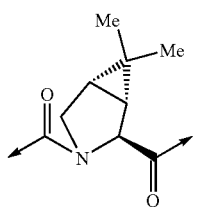
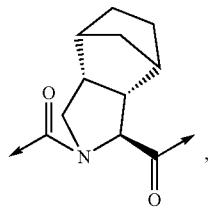
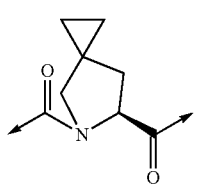
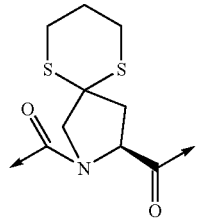
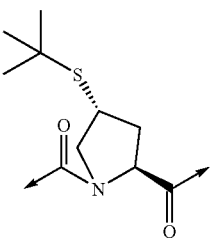
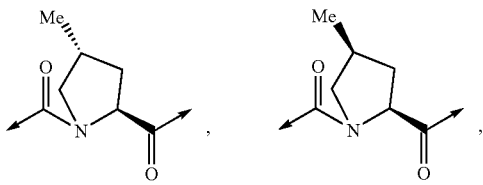
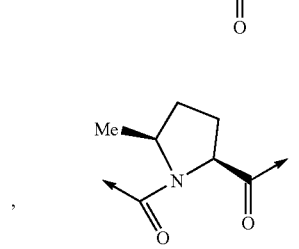
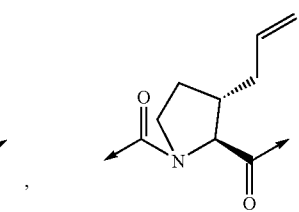
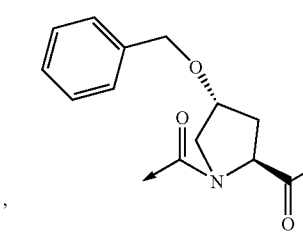
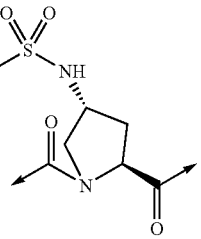
and
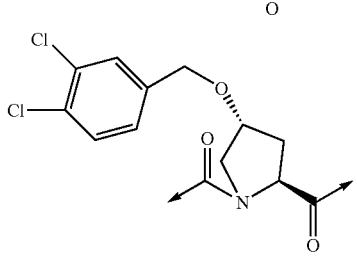

In an additional embodiment, the moiety:
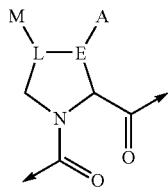
is selected from the following structures:
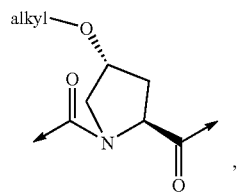 , 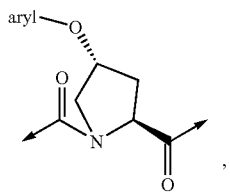 ,
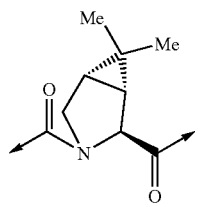 , 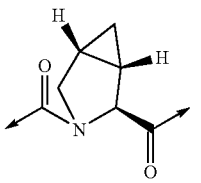 ,
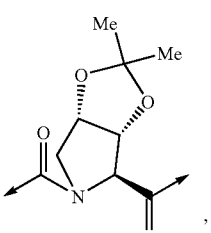 , 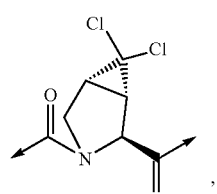 ,
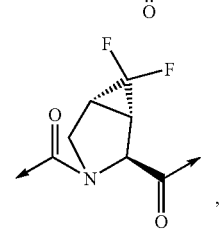 , 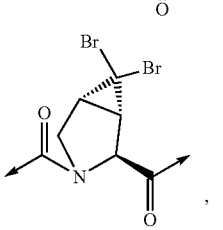 ,
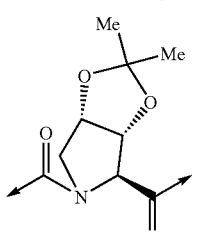 , 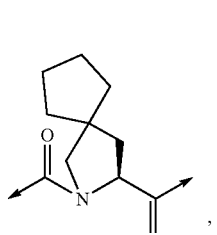 ,
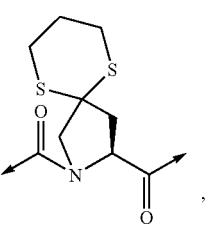 , 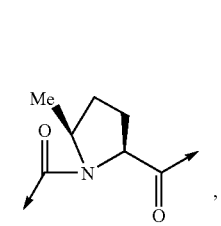 ,
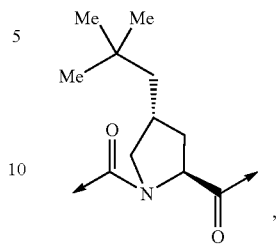 , 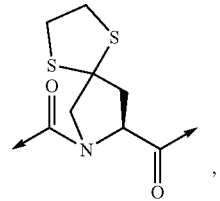 ,
, ,
, ,
, and
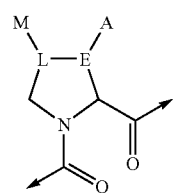
In a still additional embodiment, the moiety:

is selected from the following structures:
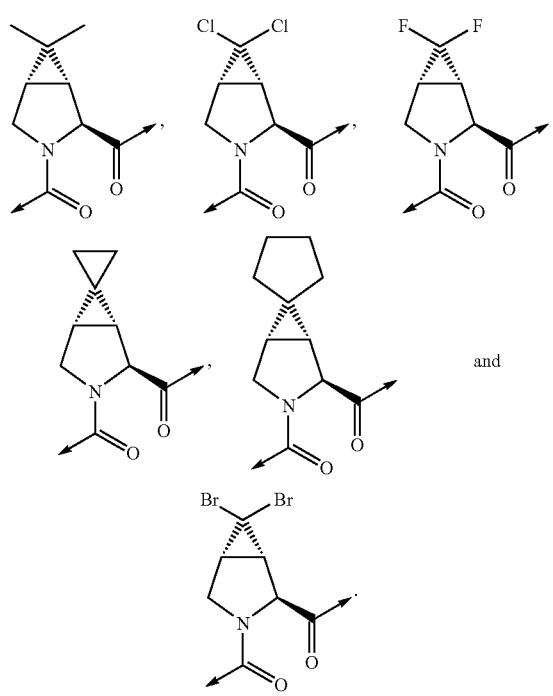
In a still additional embodiment,
R[8] is phenyl or cyclopropyl;
R[9] is H or methyl;
R[2] is selected from the group consisting of the following moieties:
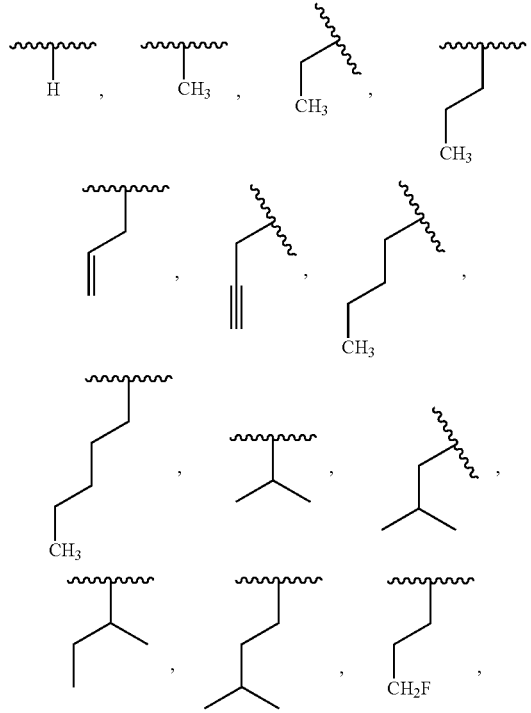
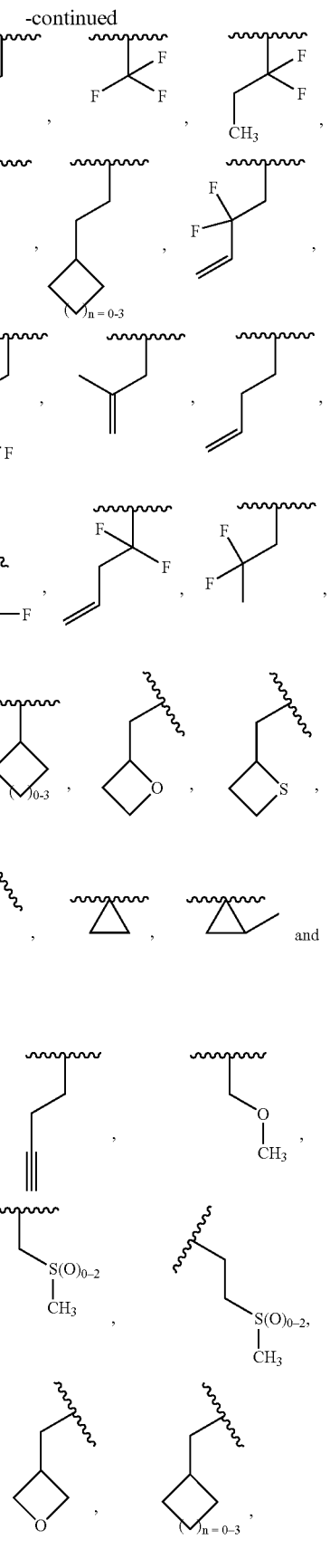

-continued
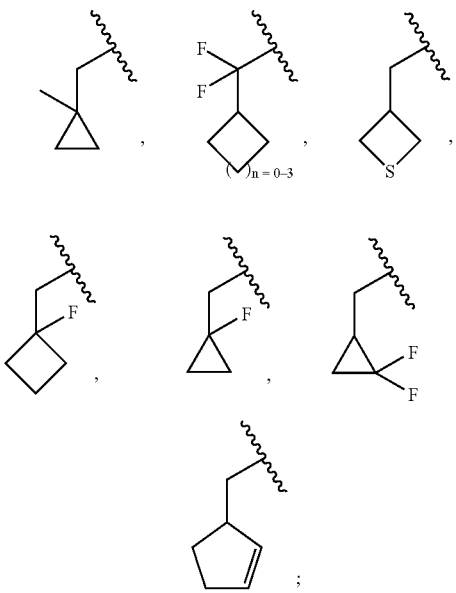
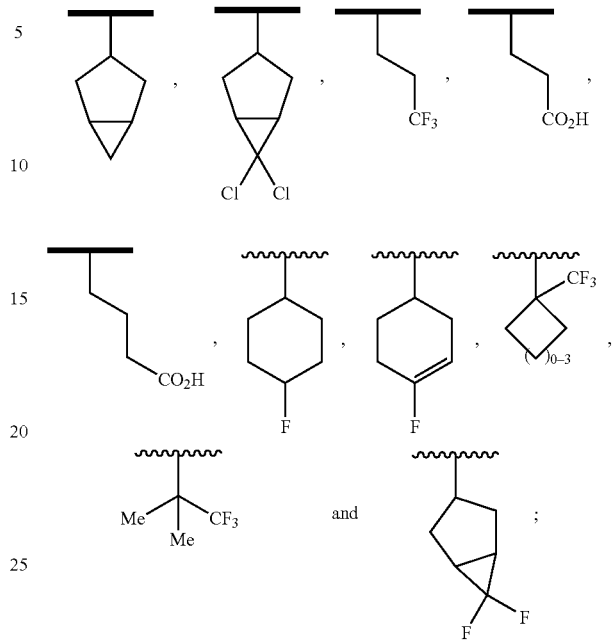
$R^3$ is selected from the group consisting of the following moieties:
and the moiety:
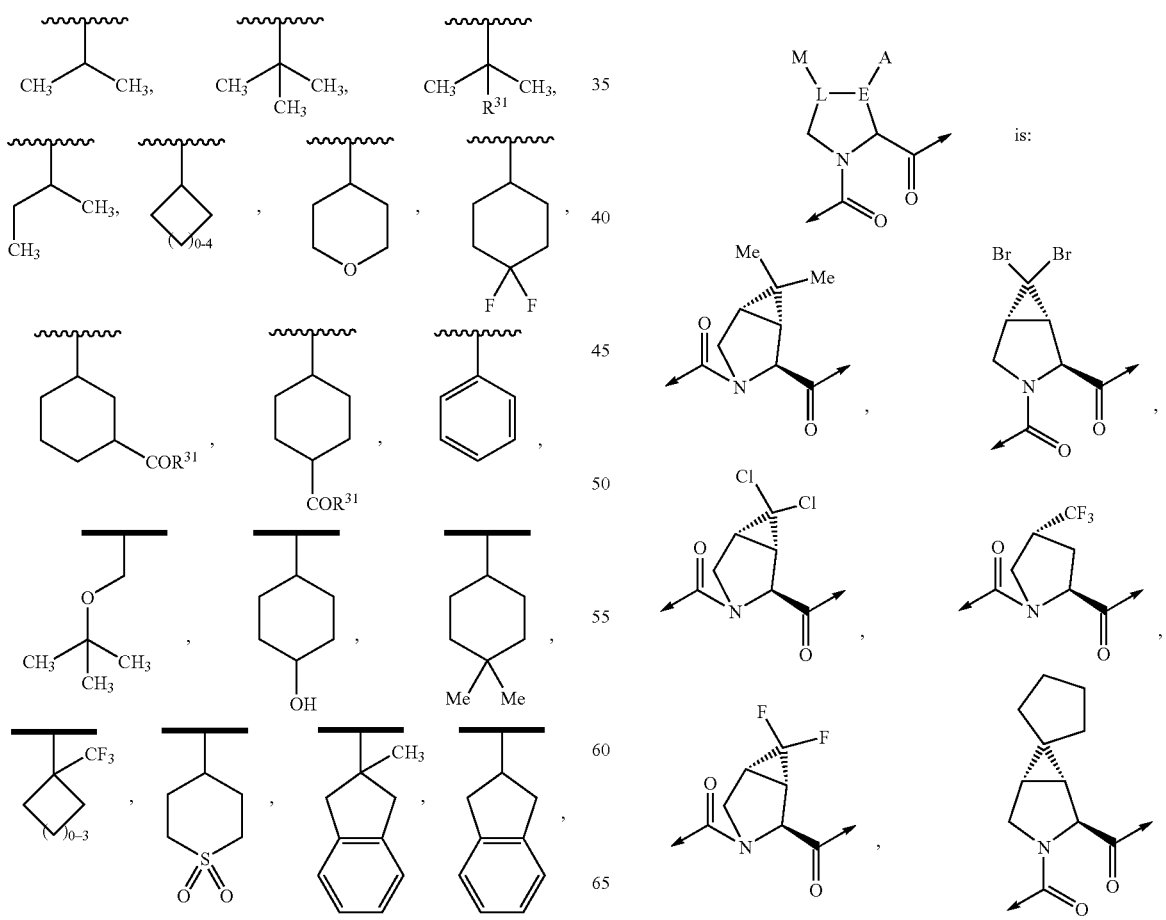
is:

-continued
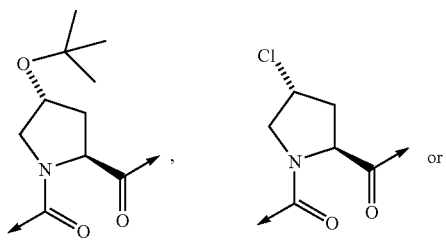
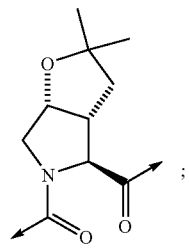
and Y is selected from:
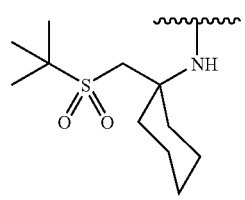 , 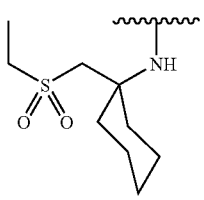 ,
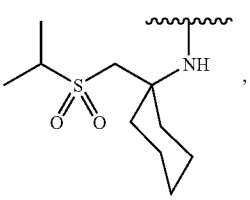 , 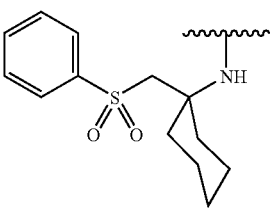 ,
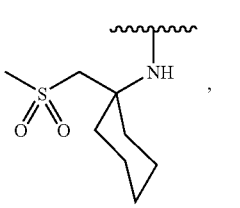 , 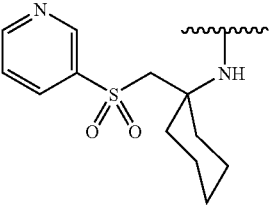 ,
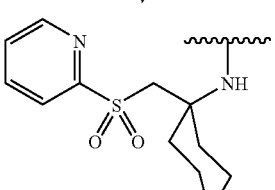 , 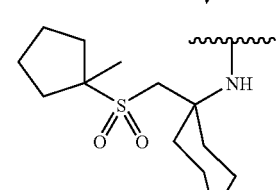 ,
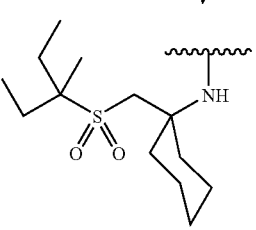 , 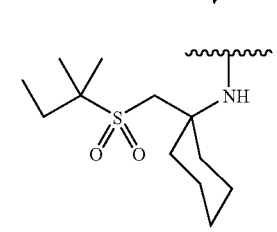 ,
-continued
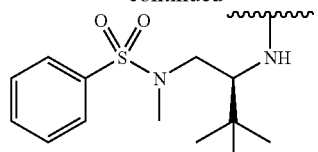 ,
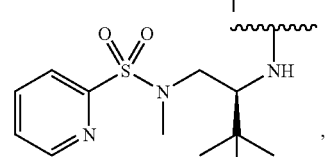 ,
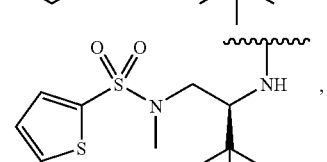 ,
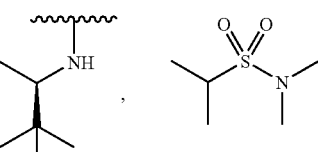 ,
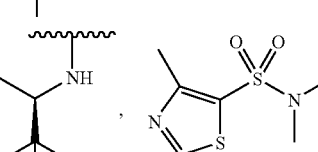 ,
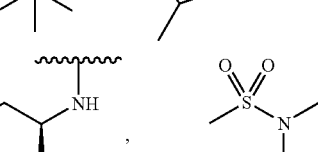 ,
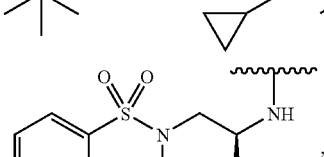 ,
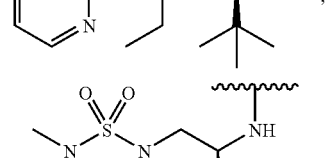 ,
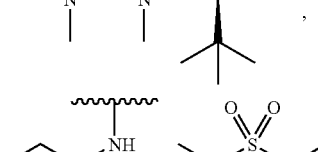 ,
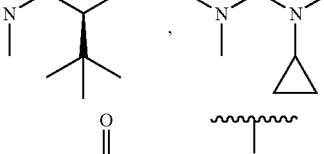 ,
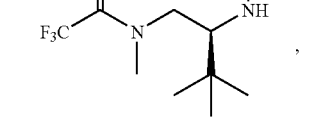 ,

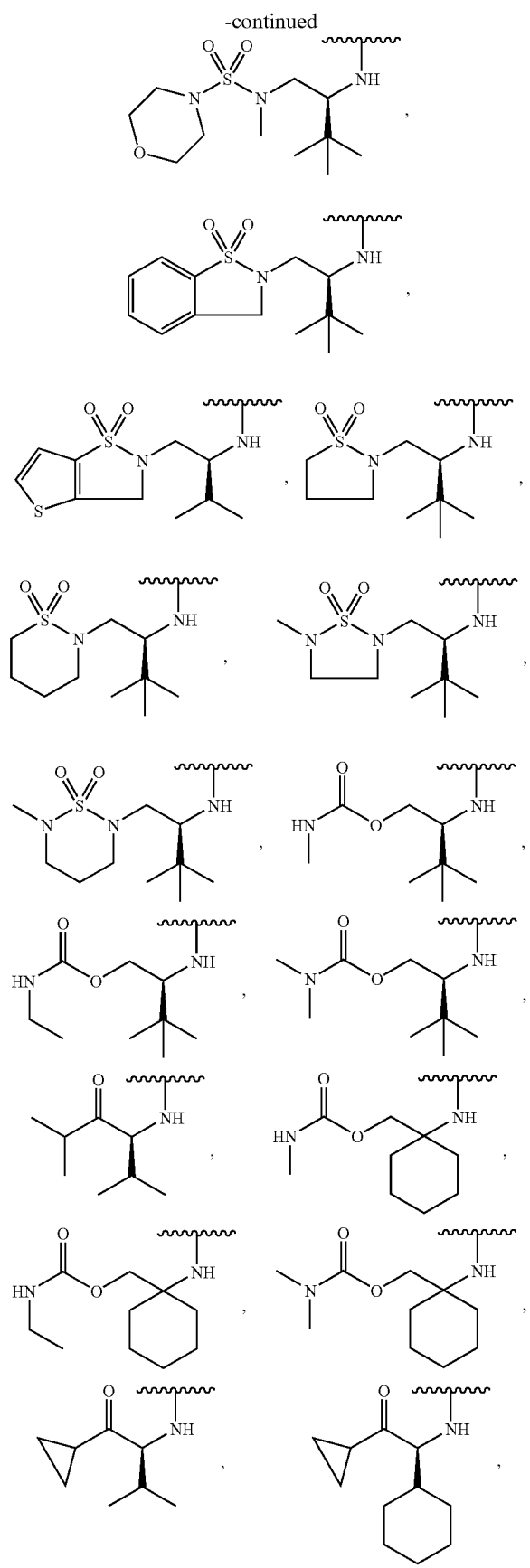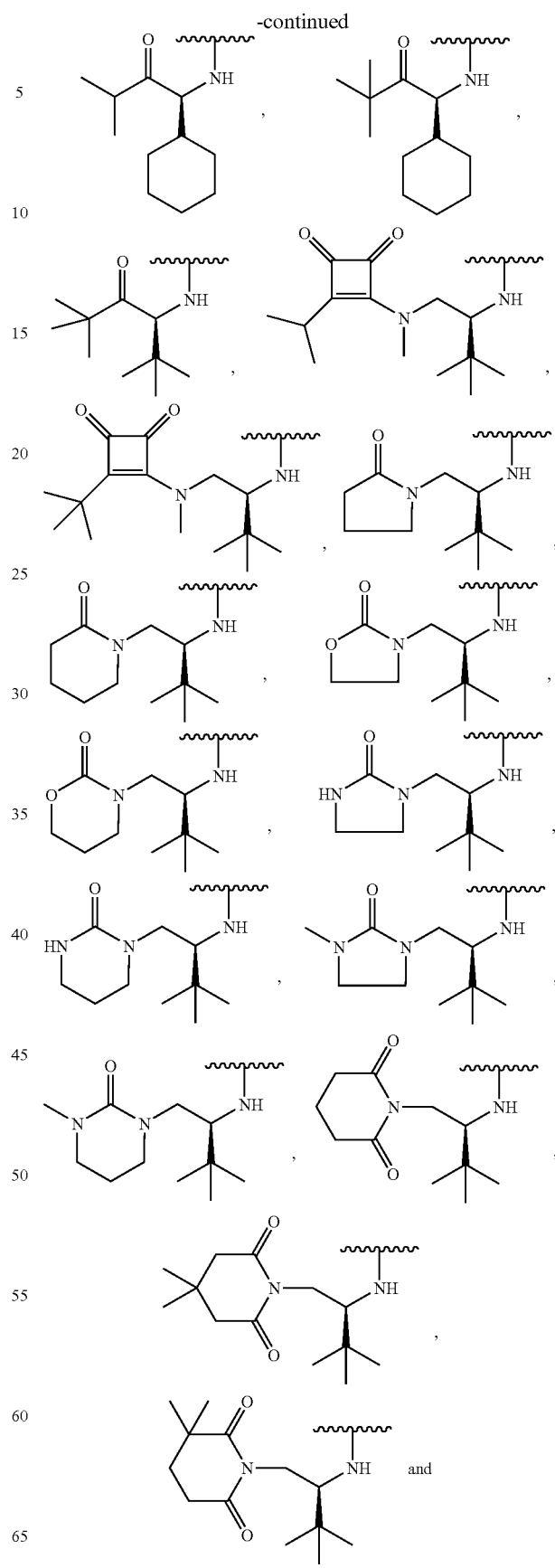

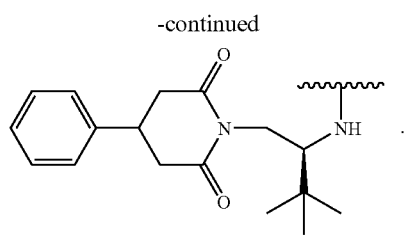
3. The Following Additional Embodiments Apply Specifically and Only to the Compound of Formula II:
In an additional embodiment, $R^8$ is phenyl or cyclopropyl; $R^9$ is H or methyl;
$R^2$ is selected from the group consisting of the following moieties:
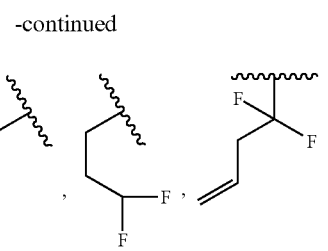
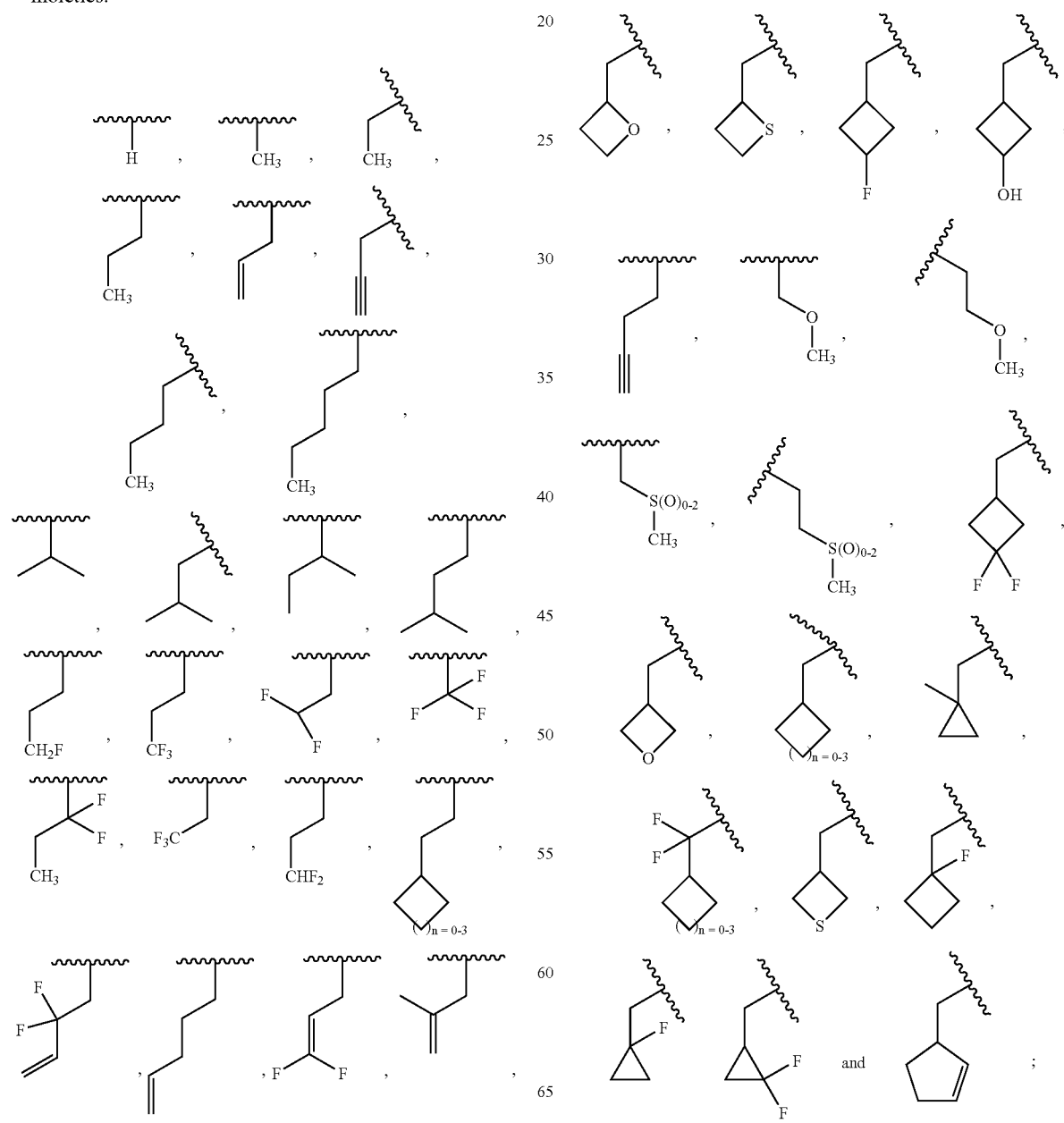

$R^3$ is selected from the group consisting of the following moieties:
and Y is selected from:
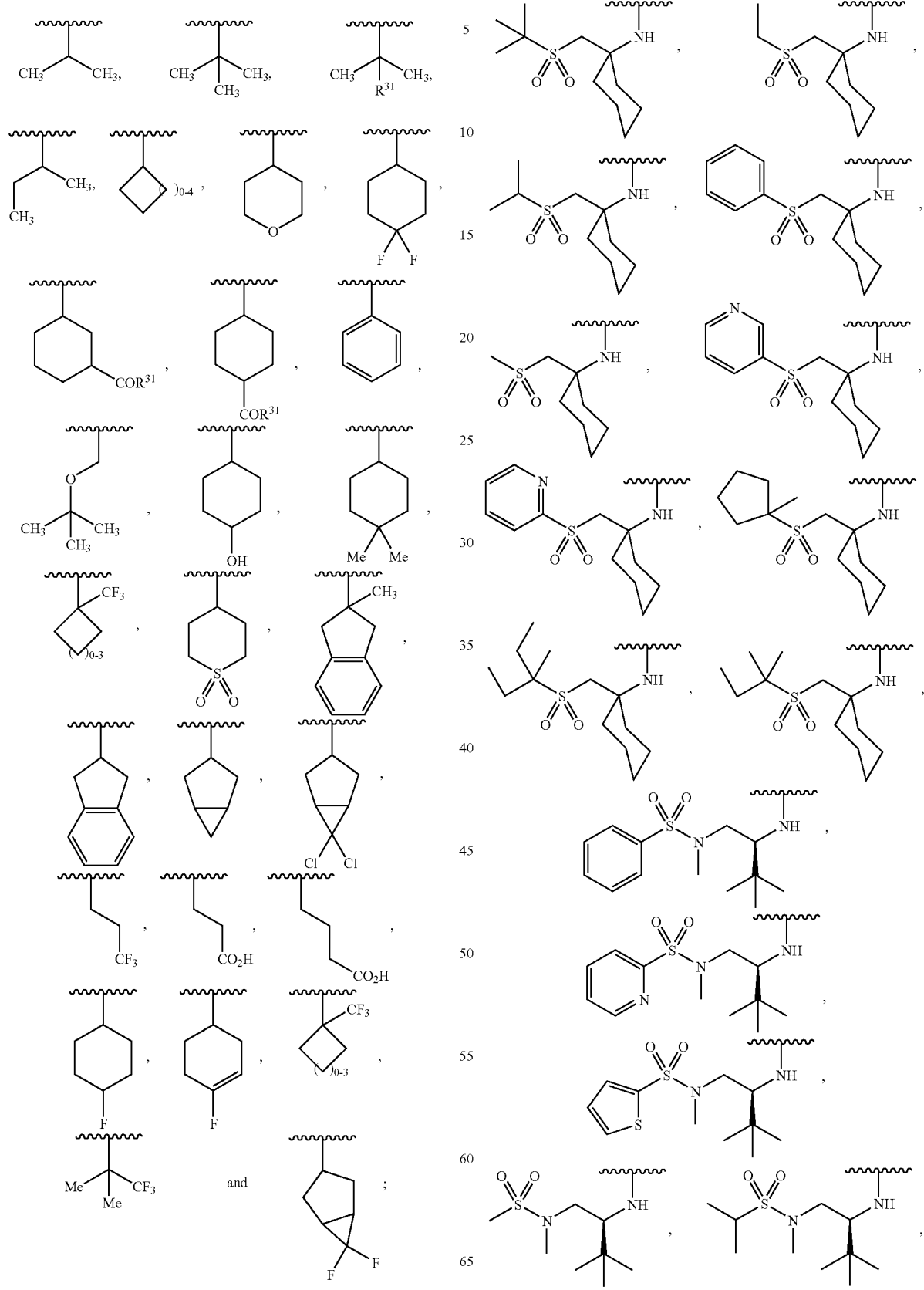

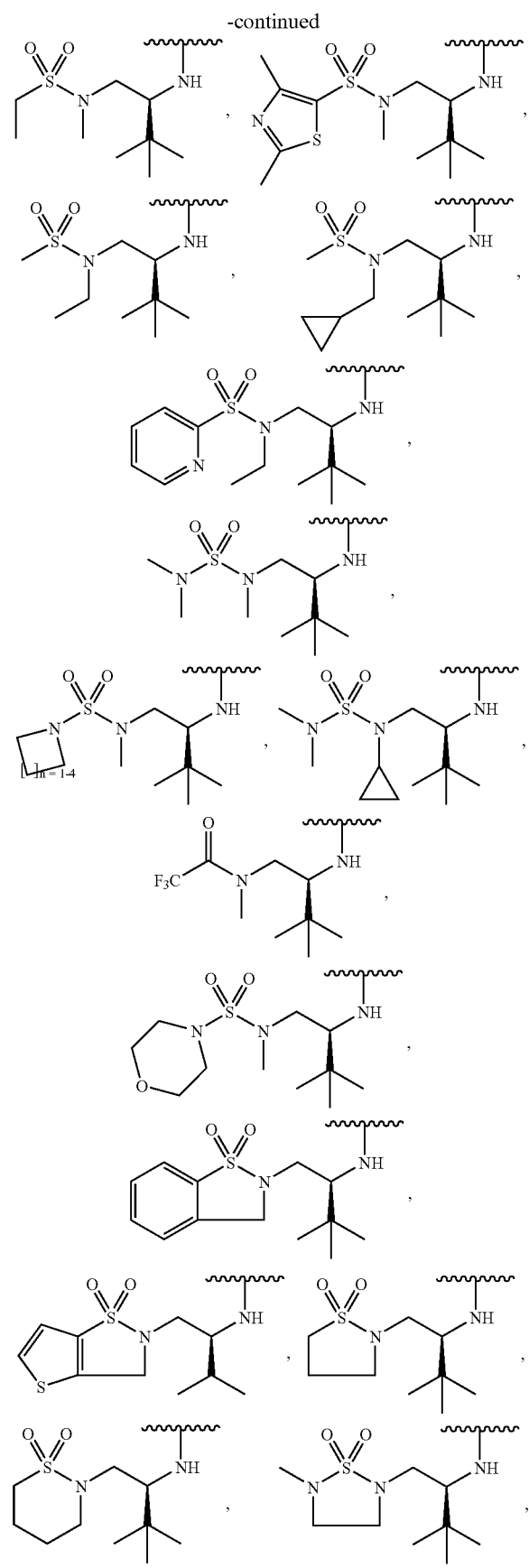
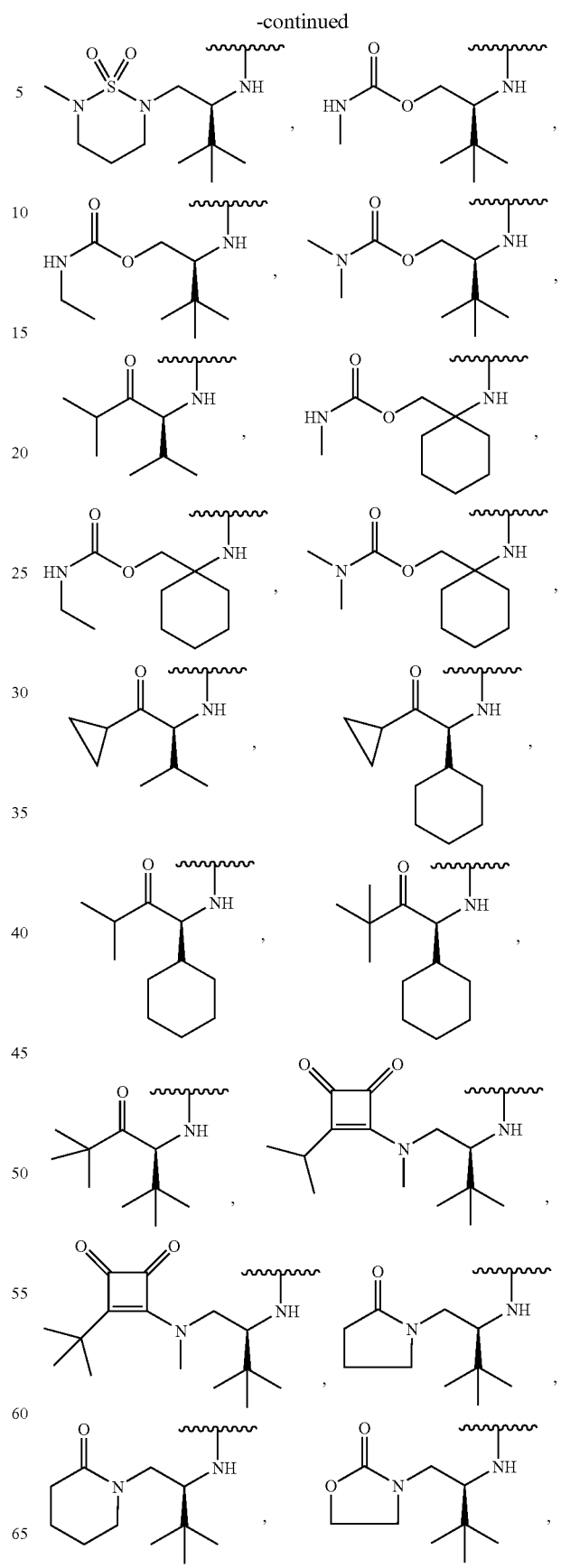

-continued
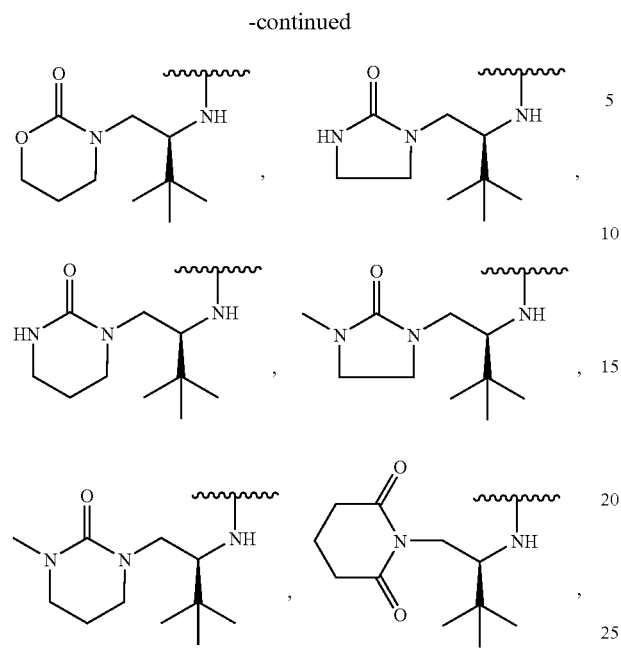
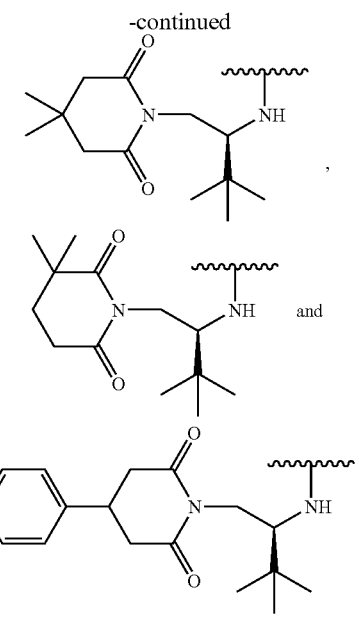
Yet another embodiment of the invention discloses compounds shown in Table 1.
TABLE 1
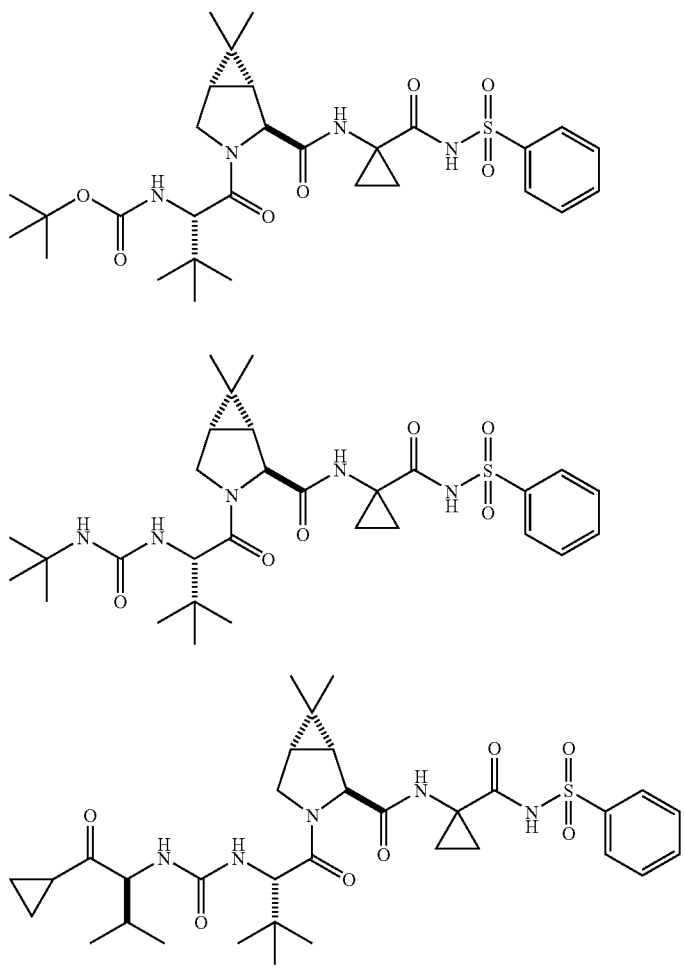

TABLE 1-continued
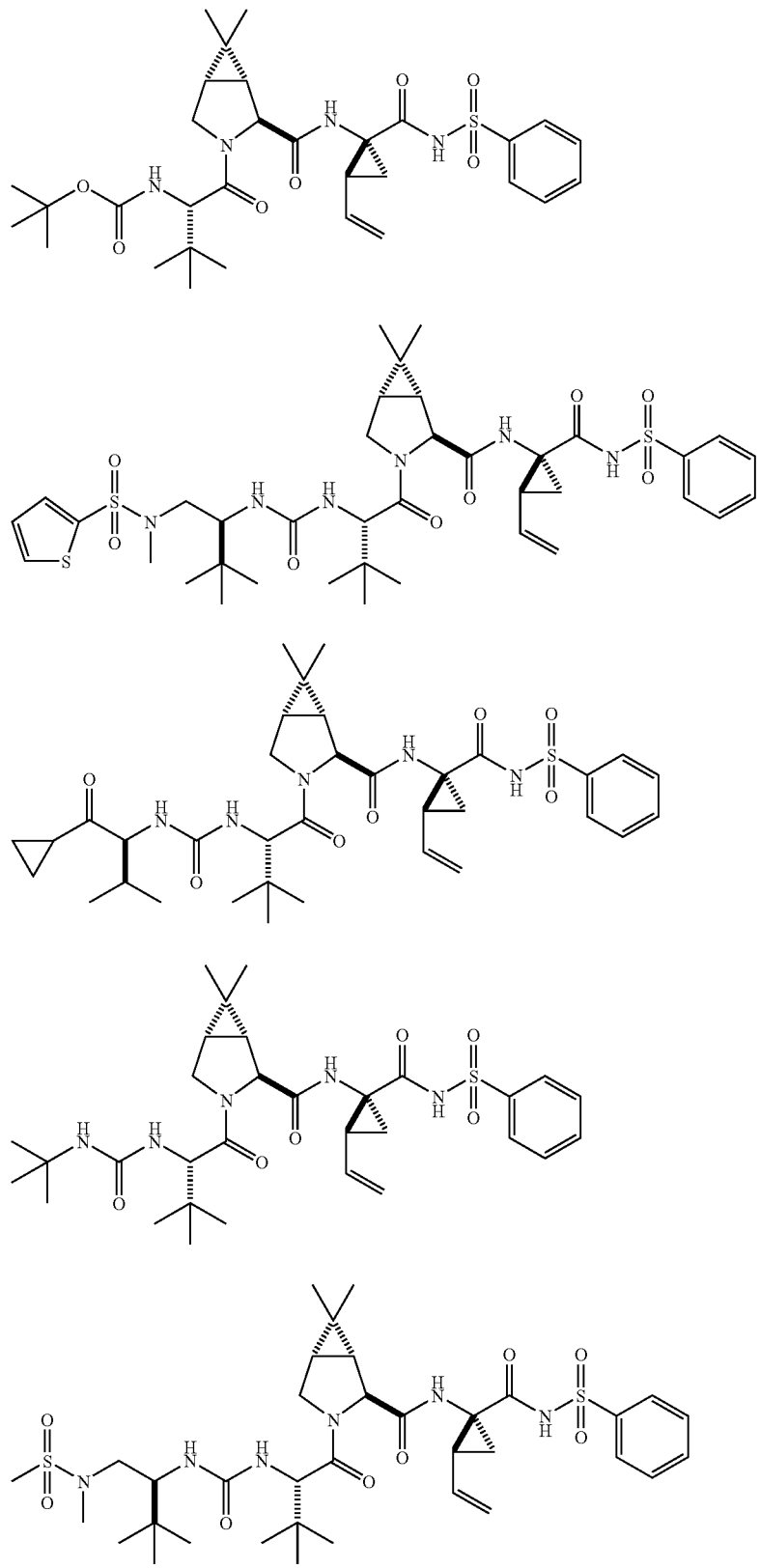

TABLE 1-continued
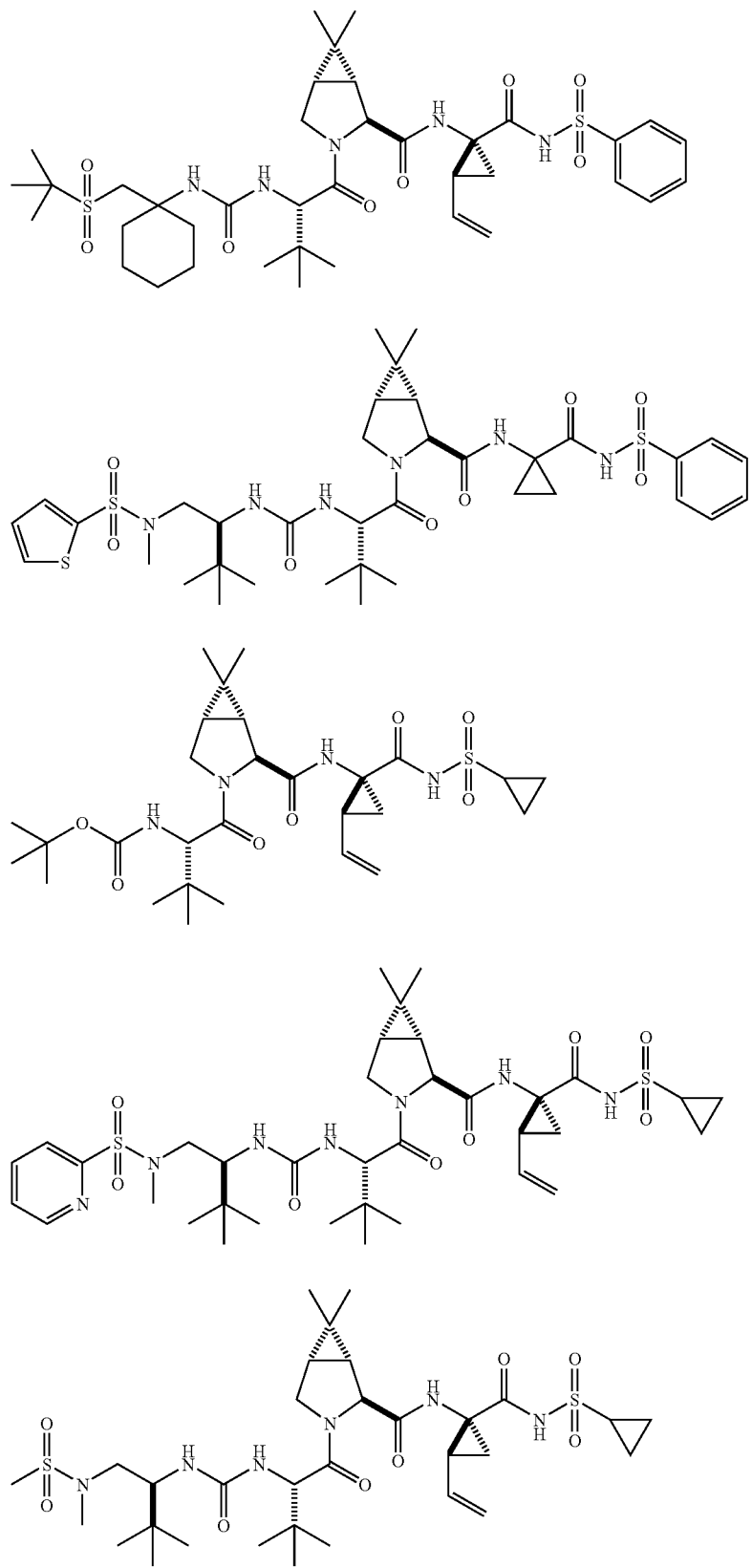

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

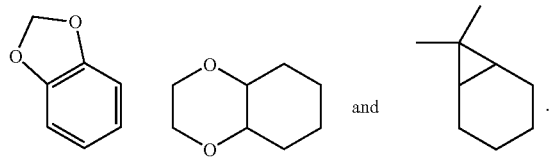

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, dihydroimidazole, dihydrooxazole, dihydrooxadiazole, dihydrothiazole, 3,4-dihydro-2H-pyran, dihydrofuranyl, fluorodihydrofuranyl, 7-oxabicyclo[2.2.1]heptenyl, dihydrothiophenyl, dihydrothiopyranyl, and the like.

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

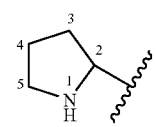

there is no —OH attached directly to carbons marked 2 and 5.

It should also be noted that tautomeric forms such as, for example, the moieties:

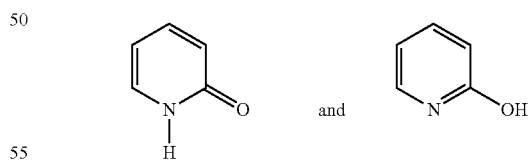

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Where used in naming the compounds of the present invention, the designations "P1', P1, P2, P3, P4" and the like, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend towards the C-terminus. For example, P1' refers to the first position away from the right hand end of the C-terminus of the cleavage site (i.e., N-terminus first position); whereas P1 starts the numbering from the left hand side of the C-terminus cleavage site, P2: second position from the C-terminus, etc. See, A. Berger et al, *Transactions of the Royal Society London Series*, B250, 249-264 (1970).

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy $(C_1-C_6)$alkyl, amino $(C_1-C_4)$alkyl or mono-N— or di-N,N-$(C_1-C_6)$alkylaminoalkyl, —$C(Y^4)Y^5$ wherein $Y^4$ is H or methyl and $Y^5$ is mono-N— or di-N,N-$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvates" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I or II can form salts which are also within the scope of this invention. Reference to a compound of Formula I or II herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I or II contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I or II may be formed, for example, by reacting a compound of Formula I or II with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I or II, and salts, solvates, esters and prodrugs thereof, may exist in their tautomeric form (for example, as an amide or imino ether). All such tautomeric forms are contemplated herein as part of the present invention.

The compounds of Formula I or II may contain asymmetric or chiral centers, and, therefore, exist in different stereoisomeric forms. It is intended that all stereoisomeric forms of the compounds of Formula I or II as well as mixtures thereof, including racemic mixtures, form part of the present invention. In addition, the present invention embraces all geometric and positional isomers. For example, if a compound of Formula I or II incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I or II may be atropisomers (e.g., substituted biaryls) and are considered as part of this invention. Enantiomers can also be separated by use of chiral HPLC column.

It is also possible that the compounds of Formula I or II may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I or II, and of the salts, solvates, esters and prodrugs of the compounds of Formula I or II, are intended to be included in the present invention.

The compounds according to the invention have pharmacological properties; in particular, the compounds of Formulas I and II can be inhibitors of HCV protease, each compound by itself or one or more compounds of Formula I or II can be combined with one or more compounds selected from within Formula I or II. The compound(s) can be useful for treating diseases such as, for example, HCV, HIV, (AIDS, Acquired Immune Deficiency Syndrome), and related disorders, as well as for modulating the activity of hepatitis C virus (HCV) protease, preventing HCV, or ameliorating one or more symptoms of hepatitis C.

The compounds of Formula I and II may be used for the manufacture of a medicament to treat disorders associated with the HCV protease, for example, the method comprising bringing into intimate contact a compound of Formula I and II and a pharmaceutically acceptable carrier.

In another embodiment, this invention provides pharmaceutical compositions comprising the inventive compound or compounds as an active ingredient. The pharmaceutical compositions generally additionally comprise at least one pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

The compounds of the invention may also be administered orally, intravenously, intranasally or subcutaneously.

The compounds of the invention may also comprise preparations which are in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the inventive compounds or pharmaceutical compositions disclosed above for treatment of diseases such as, for example, hepatitis C and the like. The method comprises administering a therapeutically effective amount of the inventive compound or pharmaceutical composition to a patient having such a disease or diseases and in need of such a treatment.

In yet another embodiment, the compounds of the invention may be used for the treatment of HCV in humans in monotherapy mode or in a combination therapy (e.g., dual combination, triple combination etc.) mode such as, for example, in combination with antiviral and/or immunomodulatory agents. Examples of such antiviral and/or immunomodulatory agents include Ribavirin (from Schering-Plough Corporation, Madison, N.J.) and Levovirin™ (from ICN Pharmaceuticals, Costa Mesa, Calif.), VP50406™ (from Viropharma, Incorporated, Exton, Pa.), ISIS14803™ (from ISIS Pharmaceuticals, Carlsbad, Calif.), Heptazyme™ (from Ribozyme Pharmaceuticals, Boulder, Colo.), VX497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

When administering a combination therapy to a patient in need of such administration, the therapeutic agents in the combination, or a pharmaceutical composition or compositions comprising the therapeutic agents, may be administered in any order such as, for example, sequentially, concurrently, simultaneously and the like. The amounts of the various actives in such combination therapy may be different amounts (dosage amounts) or same amounts (dosage amounts). The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units. Thus, for illustration purposes, a compound of Formula I and an antiviral agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

As stated earlier, the invention includes tautomers, rotamers, enantiomers and other stereoisomers of the inventive compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Illustrative procedures are outlined in the following reaction schemes. The illustrations should not be construed to limit the scope of the invention which is defined in the appended claims. Alternative mechanistic pathways and analogous structures will be apparent to those skilled in the art.

It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

Abbreviations

Abbreviations which are used in the descriptions of the schemes, preparations and the examples that follow are:
THF: Tetrahydrofuran
DMF: N,N-Dimethylformamide
EtOAc: Ethyl acetate
ACOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et2O: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
iBoc: isobutoxycarbonyl
iPr: isopropyl
$^t$Bu or Bu$^t$: tert-Butyl
Boc: tert-Butyloxycarbonyl
Cbz: Benzyloxycarbonyl
Cp: Cylcopentyldienyl
Ts: p-toluenesulfonyl
Me: Methyl
HATU: O-(7-azabenzotriazol-1-yl)-1,1,3,3-tetramethyluronium hexafluorophosphate
DMAP: 4-N,N-Dimethylaminopyridine
BOP: Benzotriazol-1-yl-oxy-tris(dimethylamino)hexafluorophosphate
PCC: Pyridiniumchlorochromate
KHMDS: Potassium Hexamethyldisilazide or Potassium bis(trimethylsilylamide)
NaHMDS: Sodium Hexamethyldisilazide or Sodium bis(trimethylsilylamide)
LiHMDS: Lithium Hexamethyldisilazide or Lithium bis(trimethylsilylamide)
10% Pd/C: 10% Palladium on carbon (by weight).
TG: Thioglycerol

EXAMPLES

Preparation of Intermediate 1.01

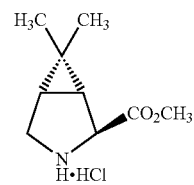

The amino ester 1.01 was prepared following the method of R. Zhang and J. S. Madalengoitia (*J. Org. Chem.* 1999, 64, 330), with the exception that the Boc group was cleaved by the reaction of the Boc-protected amino acid with methanolic HCl (4M HCl in dioxane was also employed for the deprotection).

(Note: In a variation of the reported synthesis, the sulfonium ylide was replaced with the corresponding phosphonium ylide).

Preparation of Intermediate 1.04

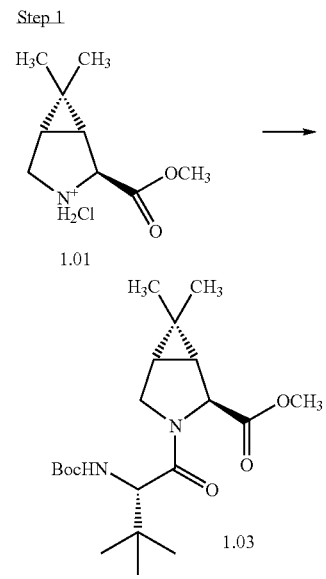

A solution of Boc-tert-Leu 1.02 (Fluka, 5.0 g 21.6 mmol) in dry CH$_2$Cl$_2$/DMF (50 mL, 1:1) was cooled to 0° C. and treated with the amine salt 1.02 (5.3 g, 25.7 mmol), NMM (6.5 g, 64.8 mmol) and BOP reagent (11.6 g, 25.7 mmol). The reaction was stirred at rt for 24 h, diluted with aq. HCl (1 M) and extracted with CH$_2$Cl$_2$. The combined organic layers were washed with HCl (aq, 1 M), sat'd. NaHCO$_3$, brine, dried (MgSO$_4$), filtered and concentrated in vacuo and purified by chromatography (SiO$_2$, Acetone/Hexane 1:5) to yield 1.03 as a colorless solid.

Step 2

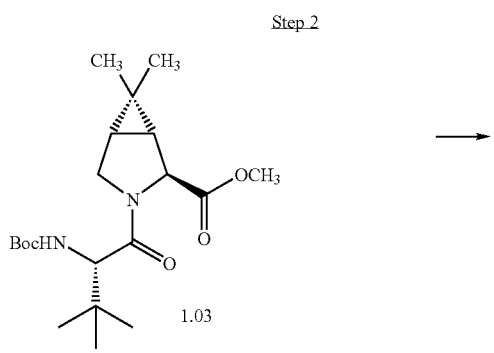

A solution of methyl ester 1.03 (4.0 g, 10.05 mmol) in THF/H$_2$O (1:1) was treated with LiOH.H$_2$O (429 mg, 10.05 mmol) and stirred at rt. for 3 h. The reaction mixture was acidified with aq. HCl and concentrated in vacuo to obtain the required intermediate, free acid 1.04.

Preparation of Intermediate 1.06

Step 1.

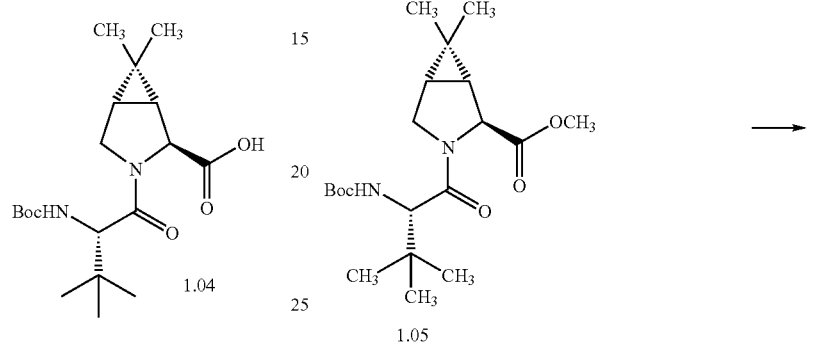

A solution of methyl ester 1.03 (4.0 g, 10.46 mmol) was dissolved in HCl (4 M soln. dioxane) and stirred at rt for 3 h. The reaction mixture was concentrated in vacuo to obtain the amine hydrochloride salt used in the next step without further purification.

A solution of the amine hydrochloride salt (397 mg, 1.24 mmol) in CH$_2$Cl$_2$ (10 mL) was cooled to −78° C. and treated with tert-butyl isocyanate (250 mg, 2.5 mmol) and stirred at rt overnight. The reaction mixture was concentrated in vacuo and the residue was diluted with aq. HCl (1M) and extracted with CH$_2$Cl$_2$. The combined organic layers were washed with aq. HCl (1M), sat'd. NaHCO$_3$ and brine. The organic layers were dried, filtered and concentrated in vacuo and the residue was purified by chromatography (SiO$_2$, acetone/Hex 1:4) to yield 1.05 as a colorless solid.

Step 2.

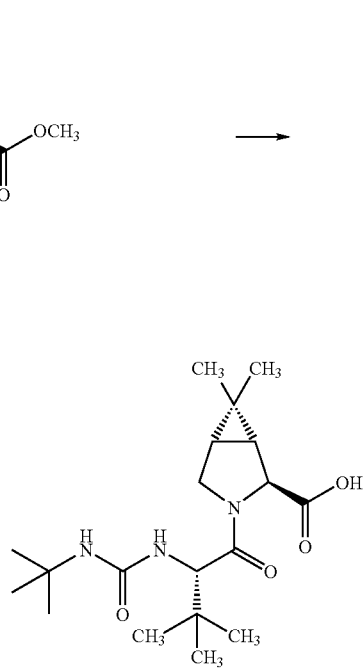

A solution of methyl ester 1.05 (381 mg, 1.0 mmol) in THF/H$_2$O (1:1, 5 mL) was treated with LiOH.H$_2$O (62 mg, 1.5 mmol) and stirred at rt for 3 h. The reaction mixture was acidified with aq. HCl and concentrated in vacuo to obtain the free acid, 1.06.

Preparation of Intermediate 1.09

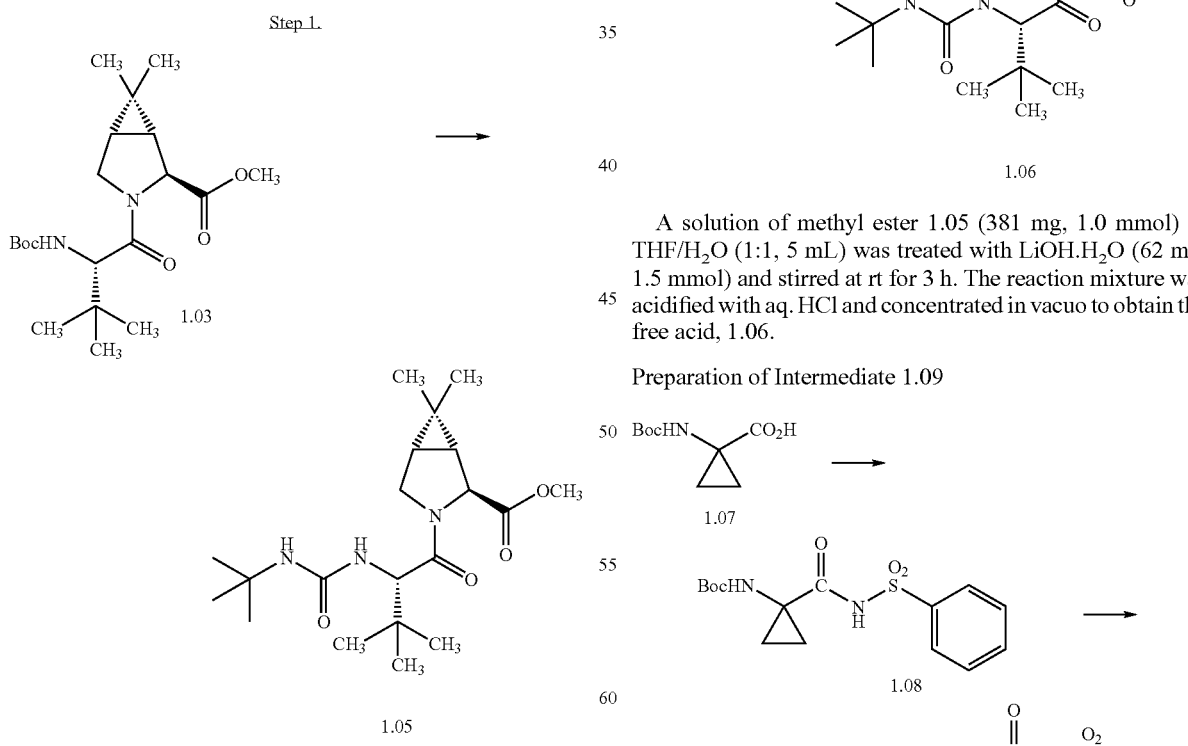

To the carboxylic acid 1.07 (Fluka, 1.0 g, 4.97 mmol) in DMF (10.0 mL) was added phenyl sulfonamide (780.8 mg, 4.97 mmol), followed by HATU (1.9 g, 4.97 mmol) at 0° C. After 3 h, the reaction was quenched with 1N HCl, washed with water, after dilution with EtOAc. The organic layer was concentrated and treated with 4N HCl in dioxane to obtain 1.09 (200.0 mg, 0.144 mmol).

Preparation of Intermediate 1.12

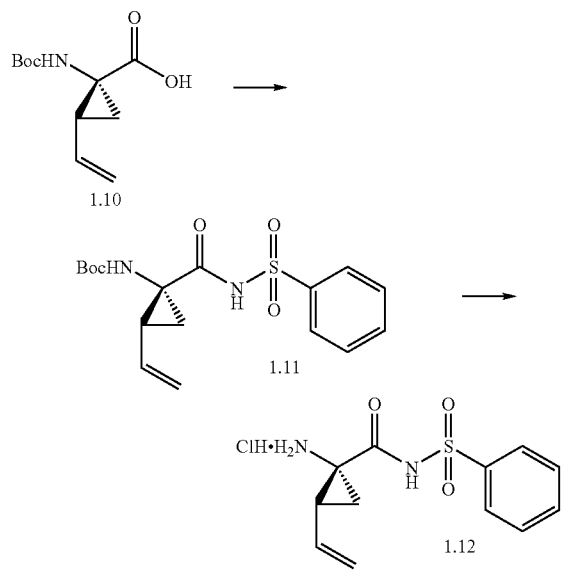

The intermediate 1.12 was prepared following the method for preparation of intermediate 1.09 starting from 1.10. Compound 1.10 can be prepared using the method of C. Fliche et al. (*Synthetic Communications* 1994, 24(20), 2873).

Preparation of Intermediate 1.14

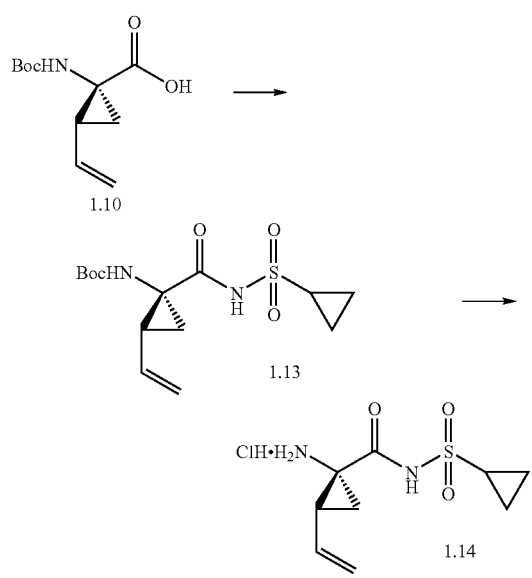

The intermediate 1.13 was prepared using the method of Campbell et al. (WO 2002060926). The intermediate 1.14 was prepared following the method for preparation of intermediate 1.09 starting from 1.08.

Example 2

Preparation of Compound of Formula 2

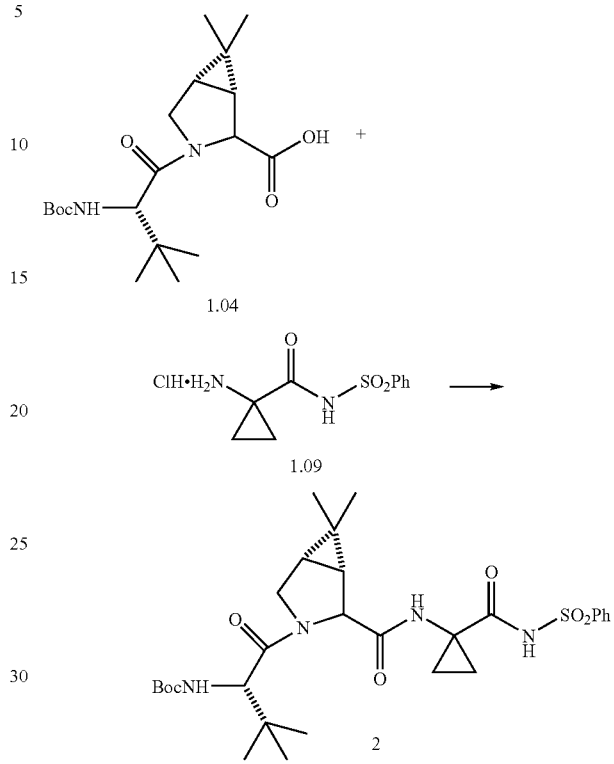

To a cooled solution (0° C.) of the intermediate 1.04 (75.0 mg, 0.20 mmol) and 1.09 (100.0 mg, 0.36 mmol) in DMF (5.0 mL) was added HATU (Aldrich, 76.05 mg, 0.20 mmol), followed by DIPEA (0.102 mL, 6 mmol). The reaction mixture was stirred for two days then warmed up to room temperature, diluted with ethyl acetate (40.0 mL), washed with 5% $KH_2PO_4$ containing 0.05 vol. of 1M $H_3PO_4$ and brine. The organic layer was dried over $MgSO_4$, filtered and concentrated to dryness. Residue was purified over silica gel using acetone-$CH_2Cl_2$ (1:9 to 1:1) to get 34.0 mg of product of formula 2 (28% yield); LCMS: (591.1: M+1).

Example 3

Preparation of Compound of Formula 3

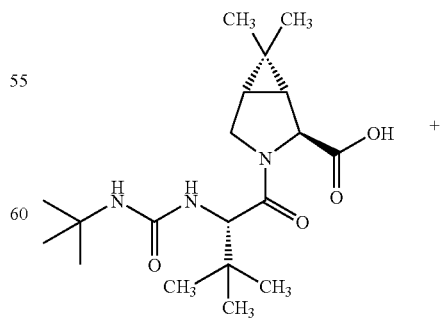

1.06

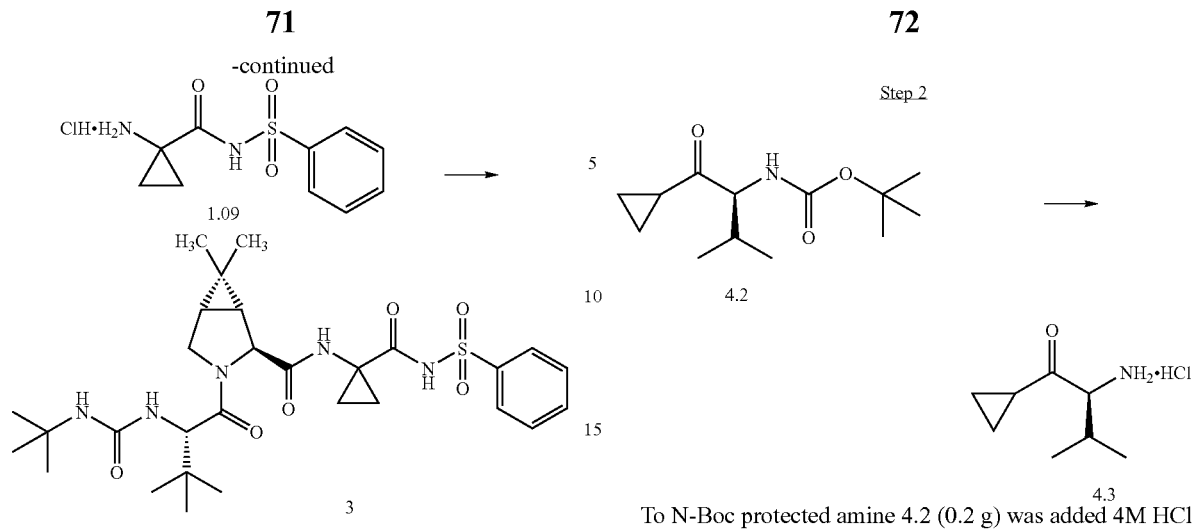

To a cooled solution (0° C.) of the intermediates 1.06 (75.0 mg, 0.2 mmol) and 1.09 (100.0 mg, 0.36 mmol) in DMF (5.0 mL) was added HATU (Aldrich, 76.05 mg, 0.20 mmol), followed by DIPEA (0.102 mL, 6 mmol). The reaction mixture was stirred for two days then warmed up to room temperature, diluted with ethyl acetate (40.0 mL), washed with 5% KH$_2$PO$_4$ containing 0.05 vol. of 1M H$_3$PO$_4$ and brine. Organic layer was dried over MgSO$_4$, filtered and concentrated to dryness. Residue was purified over silica gel using acetone-CH$_2$Cl$_2$ (1:9 to 1:1) to get 8.0 mg of product of formula 3 (6.5% yield); LCMS: (590.1).

Example 4

Preparation of Compound of Formula 4

Step 1

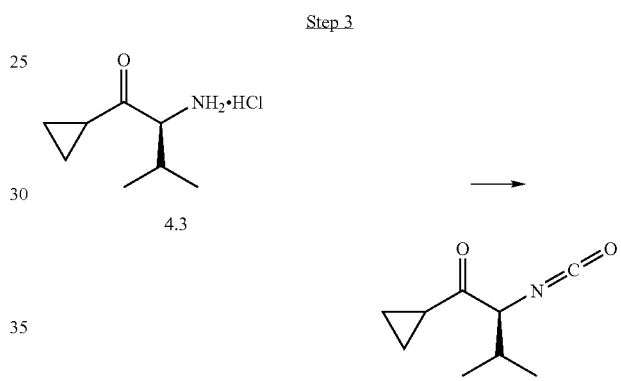

To amide 4.1 (0.5 g, 1 eq) in THF was added cyclopropylmagnesium bromide (4 eq, 7.68 mmol) at 0° C. The reaction was warmed up to RT after 15 min. and the reaction was stirred at RT for 5 hrs, then it was quenched by the addition of 1N HCl. Reaction was diluted with EtOAc and washed with brine. The organic layer was dried over MgSO$_4$, purified by column chromatography with 10% EtOAc in hexane to get 0.2 g of product 4.2. Yield 43.1%.

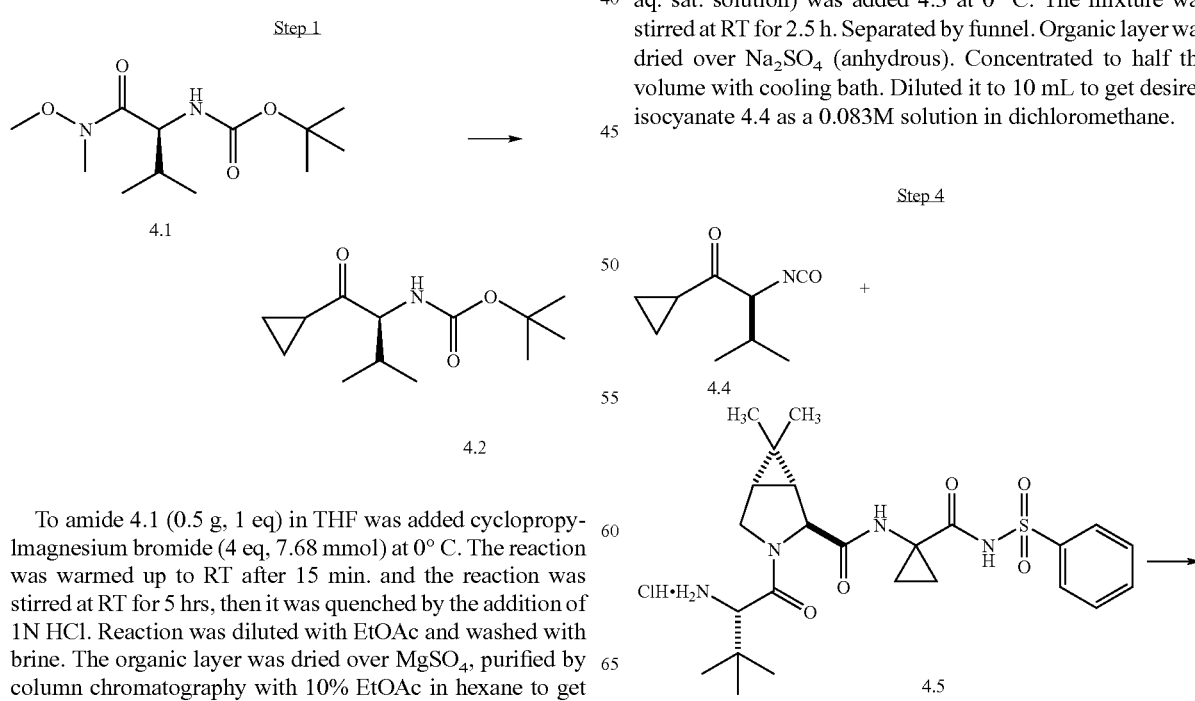

To N-Boc protected amine 4.2 (0.2 g) was added 4M HCl (in Dioxane). The reaction was stirred at RT for 50 min, TLC indicated the reaction had been completed. The mixture was concentrated to dryness to get 0.162 g of product 4.3.

Step 3

To phosgene in CH$_2$Cl$_2$ (2 eq, 1.65 mmol), NaHCO$_3$ (5 mL aq. sat. solution) was added 4.3 at 0° C. The mixture was stirred at RT for 2.5 h. Separated by funnel. Organic layer was dried over Na$_2$SO$_4$ (anhydrous). Concentrated to half the volume with cooling bath. Diluted it to 10 mL to get desired isocyanate 4.4 as a 0.083M solution in dichloromethane.

Step 4

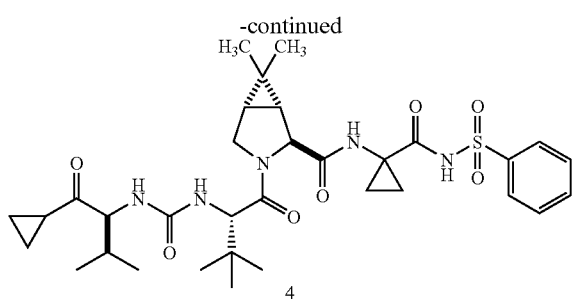

4

To a cooled solution (0° C.) of the amine hydrochloride 4.5 (30.0 mg, 0.062 mmol), prepared by treating 2 with 4N HCl for 30 min., in $CH_2Cl_2$ (2.0 mL) was added 4.4 (2.5 mL, 1.25 mmol), followed by DIPEA (3 eq.). The reaction mixture was stirred at room temperature for 1.2 h, diluted with ethyl acetate (20.0 mL), washed with 3% citric acid, brine and sat'd $NaHCO_3$. The organic layer was dried over $MgSO_4$, filtered and concentrated to dryness. Residue was purified over silica gel using acetone-$CH_2Cl_2$ (1:9 to 1:1) to get 17.0 mg of product of formula 4 (40% yield); LCMS: (658.2: M+1).

Example 5

Preparation of Compound of Formula 5

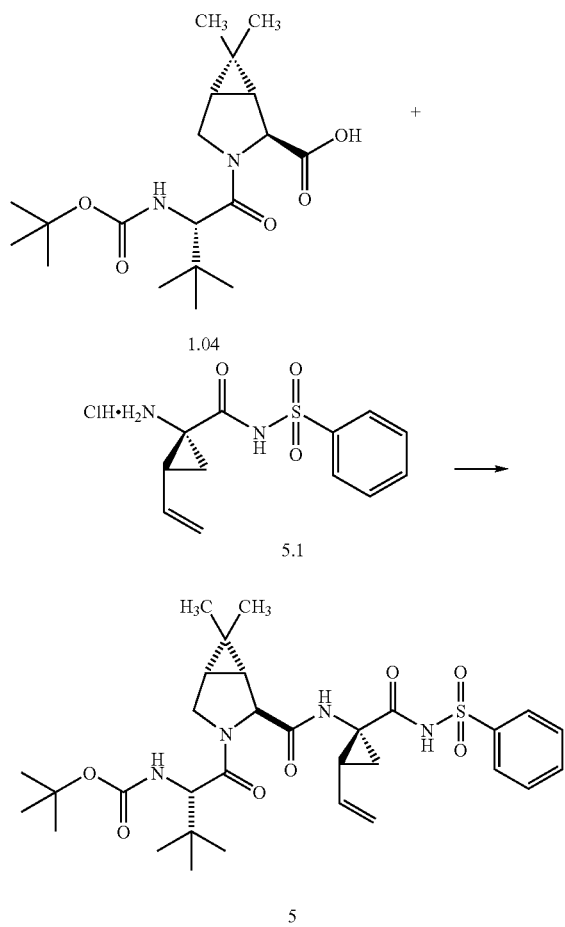

To a cooled solution (0° C.) of the acid 1.04 (763 mg, 3.36 mmol) and amine salt 5.1 (791.8 mg, 5.04 mmol) in DMF (10.0 mL) was added HATU (1.64 g, 5.6 mmol), followed by DIPEA (2.24 mL, 12.96 mmol). The reaction mixture was stirred for two days then warmed up to room temperature, diluted with ethyl acetate (40.0 mL), washed with 5% $H_3PO_4$ in $KH_2PO_4$ (0.05 M), brine and $NaHCO_3$. The organic layer was dried over $MgSO_4$, filtered and concentrated to dryness. Residue was purified over silica gel using acetone-$CH_2Cl_2$ (1:9 to 1:1) to get 134.0 mg of product of formula 5 (6% yield); LCMS: (617.1: M+1).

Example 6

Preparation of Compound of Formula 6

Step 1

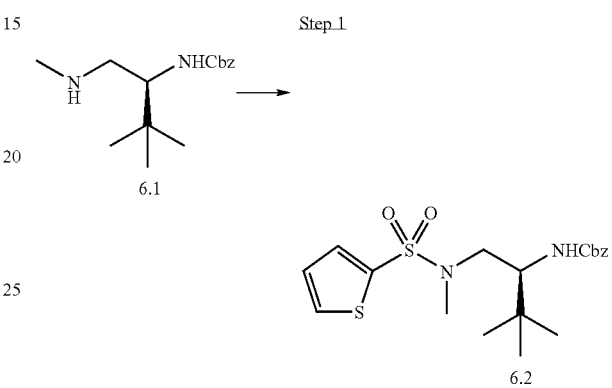

A solution of amine 6.1* (900 mg, 3.40 mmol) in $CH_2Cl_2$ at 0° C. was treated with NMM (511 mg, 5.10 mmol) and thiophene sulfonyl chloride (928 mg, 5.10 mmol) and stirred at 0° C. for 12 h. The reaction mixture was diluted with $CH_2Cl_2$ (300 mL) and washed with excess aq. HCl (1M, 500 mL). The organic layer was dried ($MgSO_4$) filtered concentrated in vacuo and purified by chromatography ($SiO_2$, Hex/EtOAc 1:9→1:1) to yield sulfonamide 6.2 (1.00 g) as a colorless solid.

* Obtained by Cbz protection of tert-Leu-NH—$CH_3$ (TCl, Jpn) followed by reduction with $BH_3$.DMS Step 2

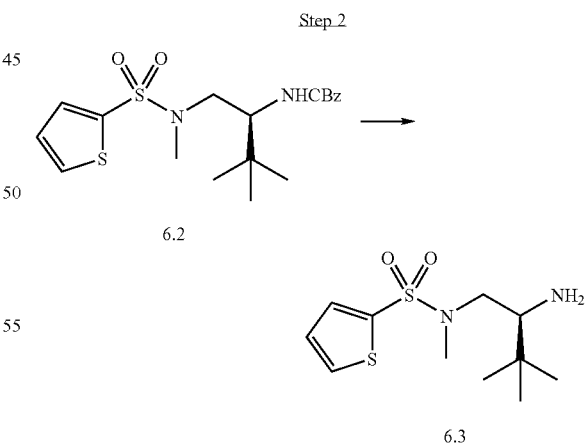

A solution of Cbz-protected compound 6.2 (1.00 g, 2.118 mmol) was treated with TFA (30 mL) and dimethylsulfide (7.78 mL) at 0° C. and stirred at rt. for 3 h. The reaction mixture was concentrated in vacuo and diluted with aq. NaOH (100 mL). The amine was extracted with methylene chloride (2×100 mL) and the combined organic layers were dried with $MgSO_4$, filtered, concentrated in vacuo and to yield 6.3 (800 mg) that was used in further reaction without purification. MS (m/z, relative intensity) 277 [(M+H)+, 100], 190 (50).

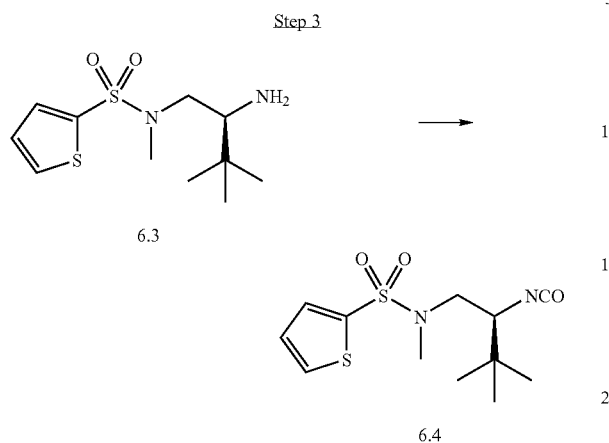

Step 3

6.3

6.4

A solution of deprotected amine 6.3 (800 mg, 2.9 mmol) in CH$_2$Cl$_2$ (10 mL) aq. saturated NaHCO$_3$ (10 mL) at 0° C. was treated with phosgene (5 mL, 15% soln. in toluene) and stirred at 0° C. for 2 h. The reaction mixture was diluted with CH$_2$Cl$_2$ (50 mL) and the organic layer was washed with cold aq. NaHCO$_3$. The organic layer was dried over MgSO$_4$, filtered and further diluted with 10 mL toluene, concentrated the methylene chloride layer and used as a solution of 6.4.

To a cooled solution (0° C.) of the amine hydrochloride of 5 (18 mg, 0.03 mmol) in CH$_2$Cl$_2$ (2.0 mL) was added 6.4 (0.5 mL, 0.075 mmol), followed by DIPEA (3 eq.). The reaction mixture was stirred at room temperature for 1.2 h, diluted with ethyl acetate (20.0 mL), washed with 3% citric acid, brine and sat'd NaHCO$_3$. The organic layer was dried over MgSO$_4$, filtered and concentrated to dryness. Residue was purified over silica gel using acetone-CH$_2$Cl$_2$ (1:9 to 1:1) to get 10.0 mg of product of formula 6 (43% yield); LCMS: (819.2: M+1).

HCV inhibitor 11, described in Table 1 was prepared using intermediate of formula 2 according to the general procedures described before.

Example 7

Preparation of Compound of Formula 7

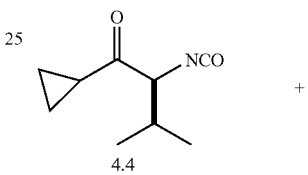

4.4

Step 4

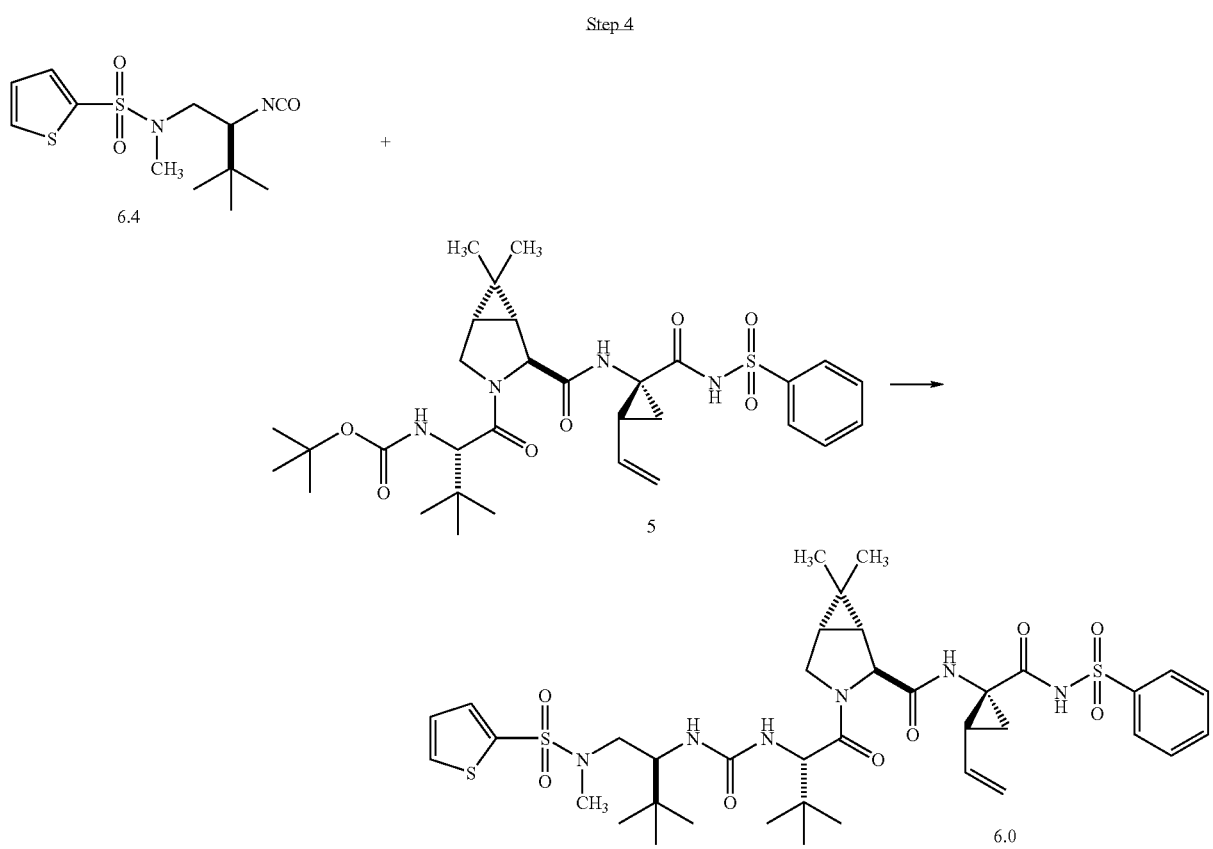

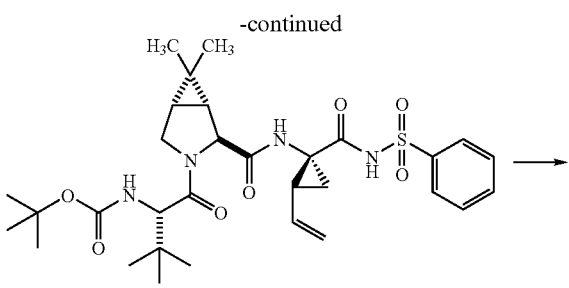

5.0

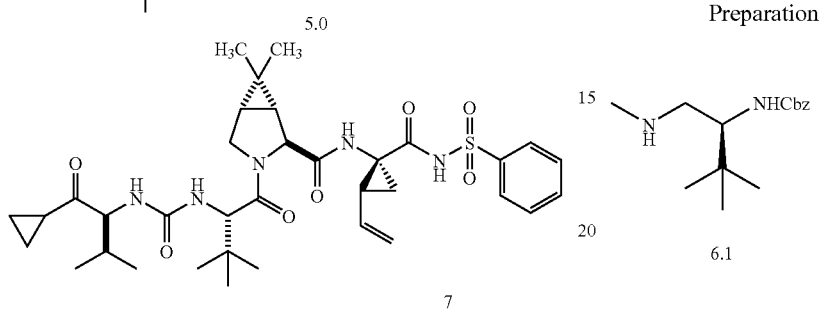

7

To compound 5 (18 mg, 0.03 mmol) was added 2 mL of 4N HCL/dioxane and stirred for 30 min and concentrated to give a pale yellow solid. To a cooled solution (0° C.) of the amine hydrochloride of 5 in CH$_2$Cl$_2$ (2.0 mL) was added 4.4 (0.18 mL, 0.09 mmol), followed by DIPEA (3 eq.). The reaction mixture was stirred at room temperature for 1.2 h, diluted with ethyl acetate (20.0 mL), washed with 3% citric acid and sat'd NaHCO$_3$. The organic layer was dried over MgSO$_4$, filtered and concentrated to dryness. Residue was purified over silica gel using acetone-CH$_2$Cl$_2$ (1:9 to 1:1) to get 8.0 mg of product of formula 7 (37% yield); LCMS: (684.2: M+1).

Example 8

Preparation of Compound of Formula 8

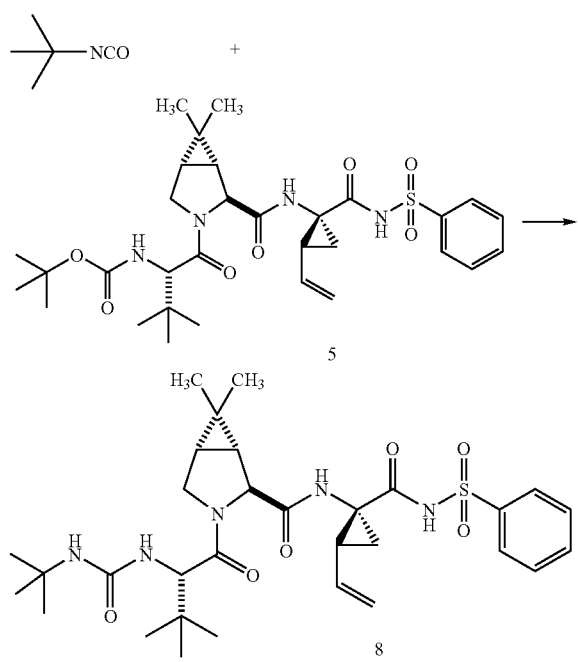

To a cooled solution (0° C.) of the amine hydrochloride of compound 5 (18 mg, 0.03 mmol) in CH$_2$Cl$_2$ (2.0 mL) was added t-butyl isocyanate (Aldrich, 10 mg, 0.10 mmol), followed by DIPEA (3 eq.). The reaction mixture was stirred at room temperature for 1.2 h, diluted with ethyl acetate (20.0 mL), washed with 3% citric acid, brine and sat'd NaHCO$_3$. The organic layer was dried over MgSO$_4$, filtered and concentrated to dryness. Residue was purified over silica gel using acetone-CH$_2$Cl$_2$ (1:9 to 1:1) to get 4.0 mg of product of formula 8 (24% yield); LCMS: (617.1: M+1).

Example 9

Preparation of Compound of Formula 9

Step 1

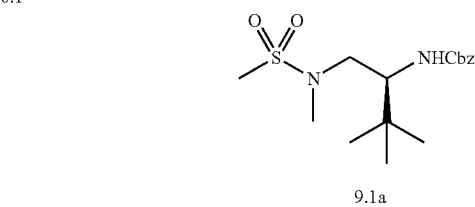

6.1

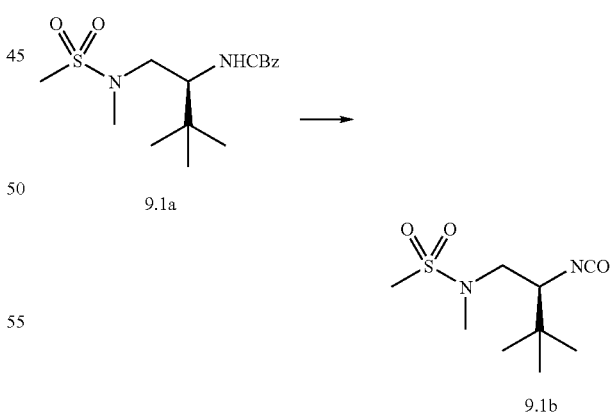

9.1a

A solution of the amine 6.1* (900 mg, 3.40 mmol) in CH$_2$Cl$_2$ at 0° C. was treated with NMM (511 mg, 5.10 mmol) and methanesulfonyl chloride (585 mg, 5.10 mmol) and stirred at 0° C. for 12 h. The reaction mixture was diluted with CH$_2$Cl$_2$ (300 mL) and washed with excess aq. HCl (1M, 500 mL). The organic layer was dried (MgSO$_4$) filtered, concentrated in vacuo and purified by chromatography (SiO$_2$, Hex/EtOAc 1:9→1:1) to yield methylsulfonamide 9.1a (1.00 g).

* Obtained by Cbz protection of tert-Leu-NH—CH$_3$ (TCI, Jpn) followed by reduction with BH$_3$.DMS.

Step 2

9.1a 9.1b

A solution of methanesulfonamide 9.1a (1.0 g, 2.9 mmol) in methanol (30 mL) was treated with palladium (200 mg, 10% wt/C) and hydrogenated at 60 psi for 3 h. The reaction mixture was filtered through a plug of celite and the filtrate was concentrated in vacuo. The residue was directly used in further reaction without further purification.

A solution of deprotected amine in CH$_2$Cl$_2$ (10 mL)/aq. saturated NaHCO$_3$ (10 mL) at 0° C. was treated with phosgene (5 mL, 15% soln. in toluene) and stirred at 0° C. for 2 h. The reaction mixture was diluted with CH₂Cl₂ (50 mL) and the organic layer was washed with cold aq NaHCO₃. The organic layer was dried (MgSO₄), filtered and further diluted with 10 mL toluene, concentrated the methylene chloride layer and used as a solution of 9.1b.

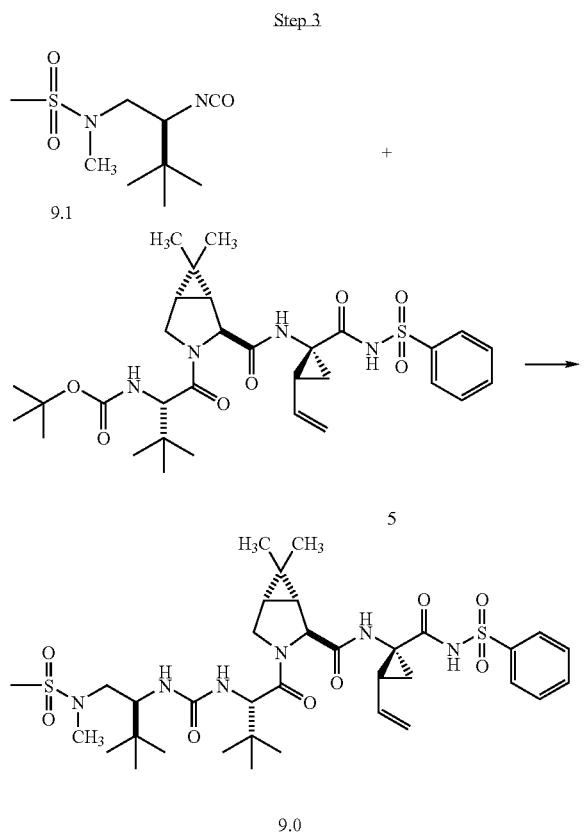

To compound 5 (18 mg, 0.03 mmol) was added 2 mL of 4N HCL/dioxane and stirred for 30 min and concentrated to give a pale yellow solid. To a cooled solution (0° C.) of the amine hydrochloride of 5 in CH₂Cl₂ (2.0 mL) was added 9.1b (0.5 mL, 0.075 mmol), followed by DIPEA (3 eq.). The reaction mixture was stirred at room temperature for 1.2 h, diluted with ethyl acetate (20.0 mL), washed with 3% citric acid, brine and sat'd NaHCO₃. The organic layer was dried over MgSO₄, filtered and concentrated to dryness. Residue was purified over silica gel using acetone-CH₂Cl₂ (1:9 to 1:1) to get 10.0 mg of product of formula 9 (43% yield); LCMS: (752.2: M+1).

Example 10

Preparation of Compound of Formula 10

Step 1

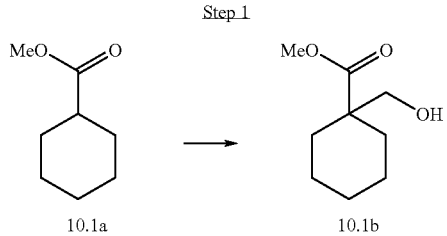

KHMDS (200 ml of a 0.5 M solution in toluene) was added, dropwise to a stirred solution of Methyl cyclohexanecarboxylate 10.1a (11.1 g; 78 mmol) in anhydrous THF (200 ml), at −78° C. under an atmosphere of nitrogen. When the addition was complete the reaction was maintained at this temperature for a further 0.5 h. before the addition of benzyl chloromethyl ether (TCI, 18.6 ml; 134 mmol). The reaction was allowed to warm to room temperature overnight and water (100 ml) was added. Aqueous work-up provided a residue which was purified by silica gel column chromatography using EtOAc; hexanes (1:10) as eluent to give the desired, impure, intermediate ether (14.98 g) as a colorless oil.

A black suspension of 10% Pd/C (0.5 g) and the aforementioned crude ether (4.1 g) in MeOH (80 ml) was exposed to an atmosphere of nitrogen (balloon) at room temp., overnight. The reaction was filtered through a pad of celite and the solid was washed thoroughly with methanol. The combined filtrate was concentrated under reduced pressure and the crude product was purified by silica gel column chromatography using EtOAc; hexanes (1:5) to give the primary alcohol (10.1b; 0.62 g), a colorless oil.

Step 2

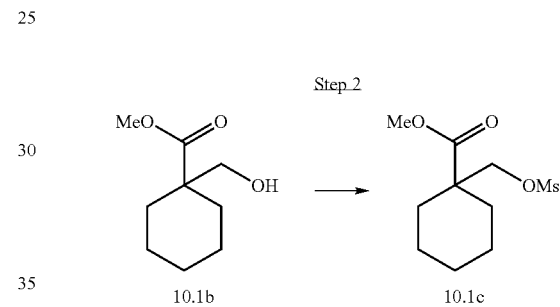

Methanesulfonyl chloride (0.31 ml) followed by triethylamine (0.75 ml) were added to a stirred solution of the primary alcohol (10.1b; 0.62 g) at 0° C., under an atmosphere of nitrogen. The resulting mixture was stirred at this temperature for 0.5 h. The reaction mixture was extracted into EtOAc and washed with 1M HCl, sat. aq. NaHCO₃, water, dried (MgSO₄) and concentrated. The residue (mesylate 10.1c; 0.74 g), was obtained as a yellow oil, which was used in subsequent steps without purification.

Step 3

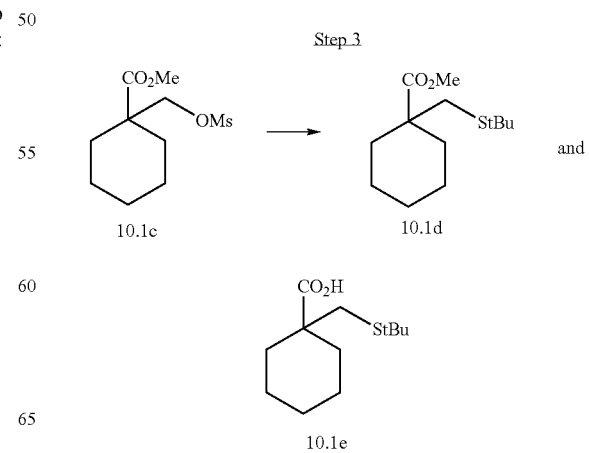

Dimethylformamide (20 ml; anhydrous; Aldrich) was added to sodium hydride (0.56 g; Aldrich) and tert-butyl mercaptan was added to the suspension while cooled in an ice bath under an atmosphere of nitrogen. Once the addition was complete the mesylate (10.1c; prepared as above from 2.00 g of alcohol; 10.1b) was added and the resulting mixture was stirred overnight at room temperature. The reaction was partitioned between EtOAc and water and the organic phase was separated, dried (MgSO$_4$). Column chromatography on silica gel using EtOAc-Hexanes (2:98) provided the methyl ester-sulfide (10.1d; 1.75 g).

EtOAc was added to the aqueous phase and 10% aq. HCl was added until the water layer pH=1. The organic layer was separated, washed with water, dried and concentrated under reduced pressure to give the sulfide-carboxylic acid (10.1e; 0.747 g) as a white solid.

Step 4

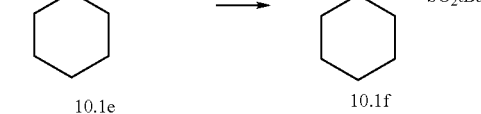

10.1e    10.1f

To the sulfide (10.1e; 2.287 g) in methanol (75 ml) was added a solution of oxone (18.00 g; from Aldrich) and the resulting white suspension was stirred overnight at room temperature. The volatiles were removed under reduced pressure and the white solid partitioned between EtOAc and water. The organic phase was separated, dried and concentrated to provide the sulfone (10.1f; 2.52 g; contains some solvent).

Step 5

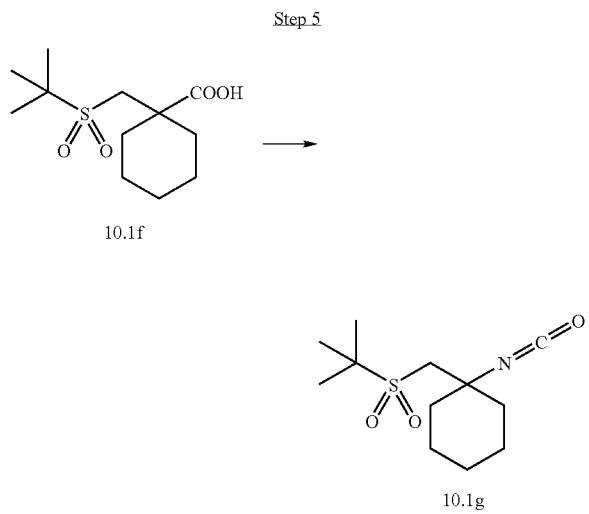

A solution of acid 10.1f (1.61 g) in 50 mL of toluene was treated with DPPA (1 eq, 1.33 mL, d 1.270) and triethylamine (1 eq, 0.85 mL, d 0.726). The mixture was heated to 100° C. for 2 h. The reaction mixture was diluted with aq sat NaHCO$_3$ and extracted with dichloromethane (2×100 mL). The combined organic layers were washed with aq sat NaHCO$_3$ and brine. The organic layer was dried over MgSO$_4$, filtered and concentrated under reduced pressure until approximately 20 mL of solvent were left. The solution of the product 10.1g was adjusted to 0.2M concentration of isocyanate using toluene.

Step 6

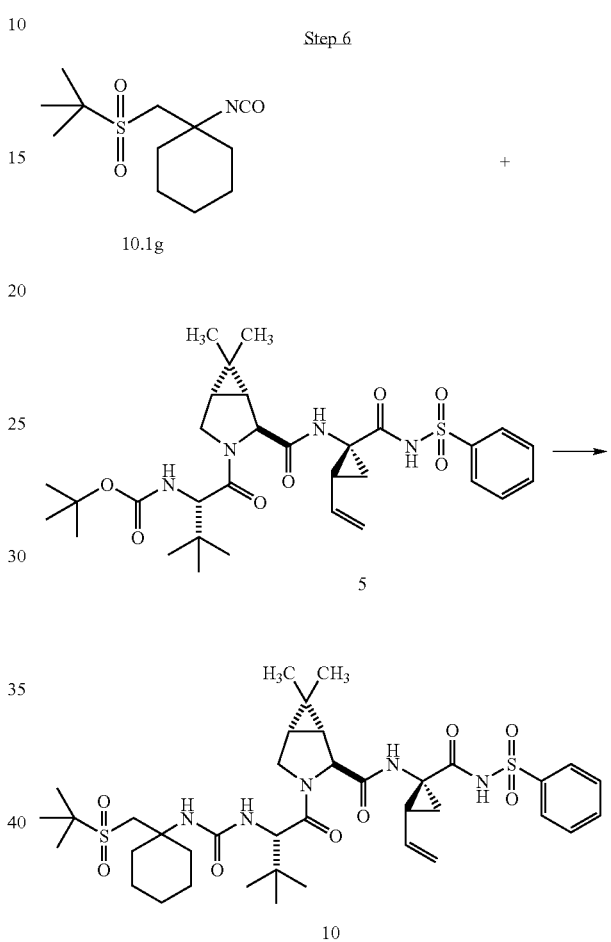

To a cooled solution (0° C.) of the amine hydrochloride of the compound 5 (18 mg, 0.07 mmol) in CH$_2$Cl$_2$ (2.0 mL) was added 10.1g (19.7 mg, 0.076 mmol) followed by DIPEA (3 eq.). The reaction mixture was stirred at room temperature for 1.2 h, diluted with ethyl acetate (20.0 mL), washed with 3% citric acid, brine, dried over NaHCO$_3$. The organic layer was dried over MgSO$_4$, filtered and concentrated to dryness. Residue was purified over silica gel using acetone-CH$_2$Cl$_2$ (1:9 to 1:1) to get 10.0 mg of product of formula 10, (43% yield); LCMS: (777.2: M+1).

HCV inhibitors 12, 13 and 14, described in Table 1 were prepared using intermediate of formula 1.14 according to general procedures described before for the preparation of compounds 5 and 6.

The compounds shown in the following Table 1 under category A have Ki<100 nM, and under category B have Ki>100 nM.

TABLE 1

| Entry | Structure | Ki |
|-------|-----------|-----|
| 2 | 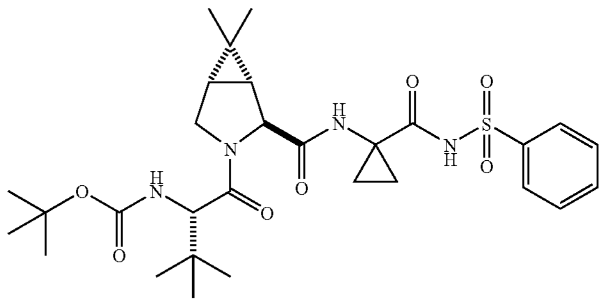 | B |
| 3 | 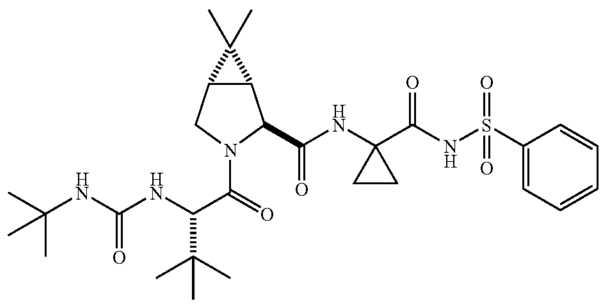 | B |
| 4 | 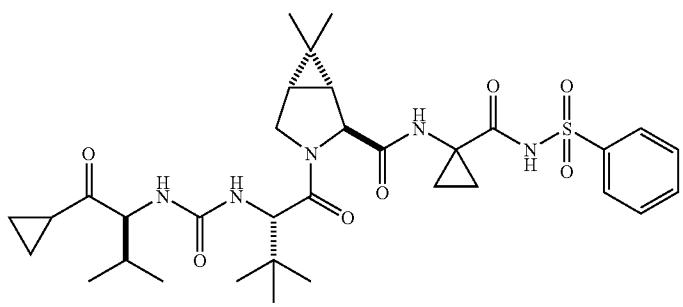 | B |
| 5 | 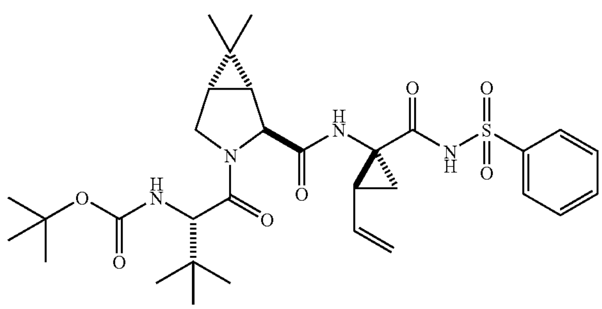 | B |
| 6 | 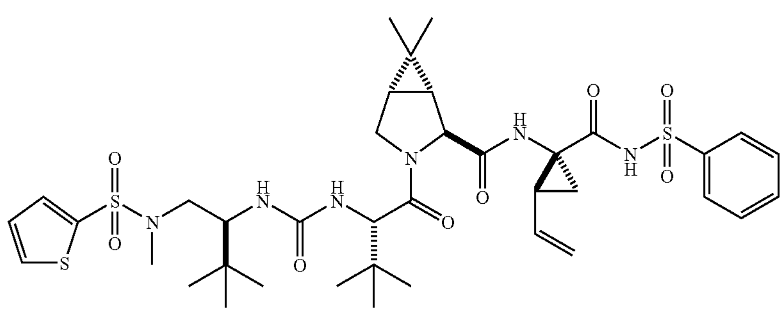 | A |

TABLE 1-continued

| Entry | Structure | Ki |
|---|---|---|
| 7 | 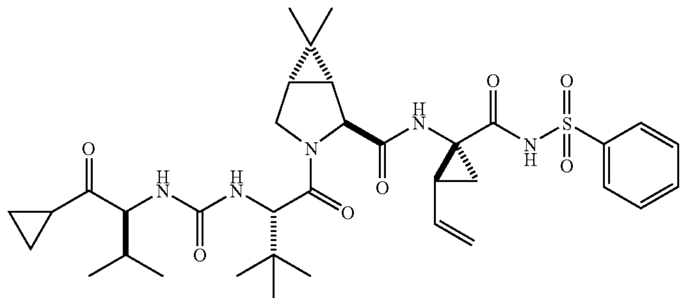 | A |
| 8 | 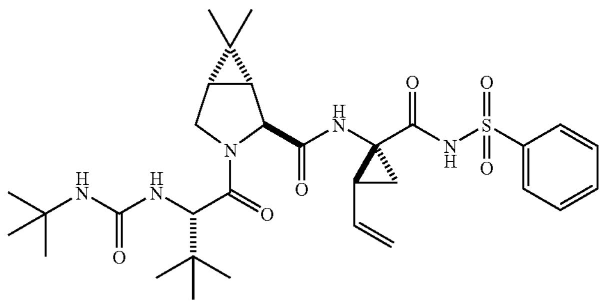 | B |
| 9 | 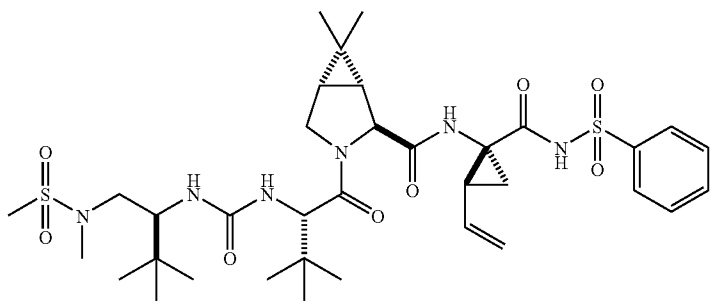 | A |
| 10 | 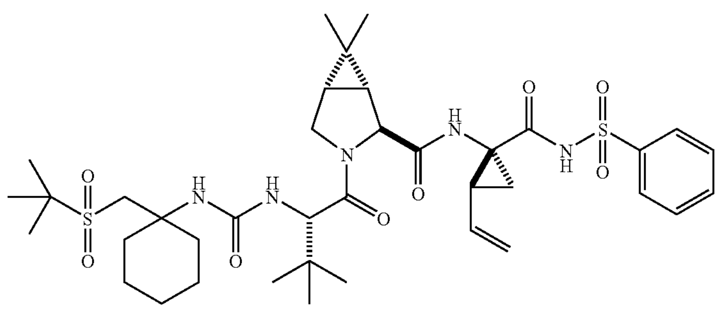 | A |
| 11 | 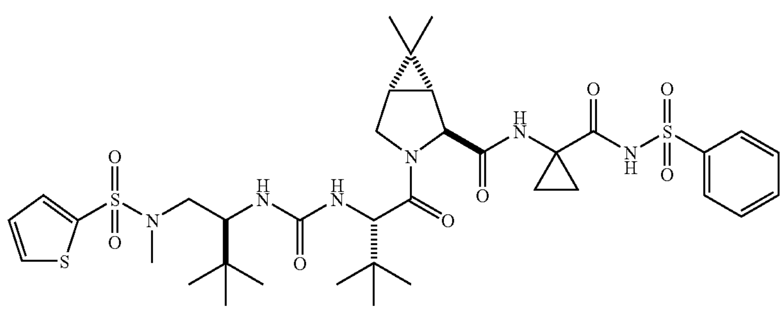 | B |

TABLE 1-continued

| Entry | Structure | Ki |
|---|---|---|
| 12 | 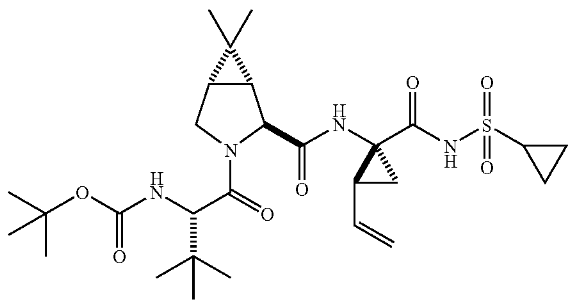 | A |
| 13 | 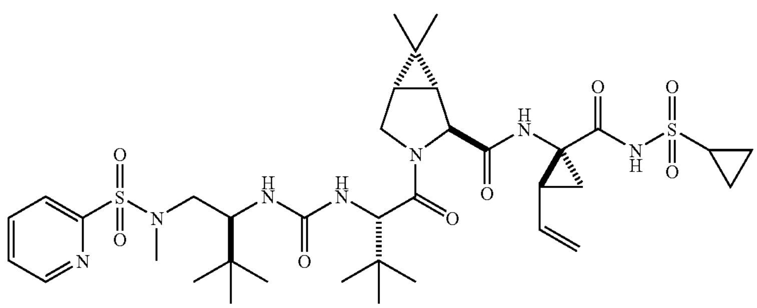 | A |
| 14 | 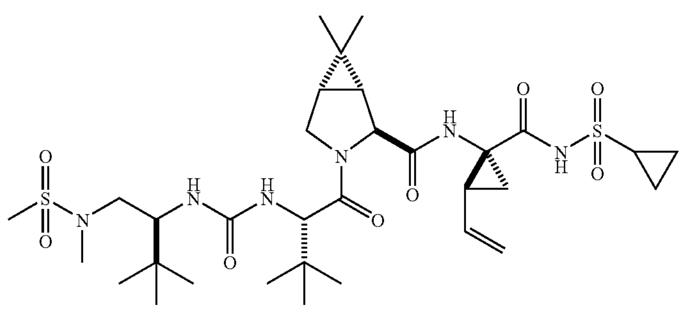 | A |

The present invention relates to novel HCV protease inhibitors. This utility can be manifested in their ability to inhibit the HCV NS3/NS4a serine protease. A general procedure for such demonstration is illustrated by the following in vitro assay.

Assay for HCV Protease Inhibitory Activity:

Spectrophotometric Assay: Spectrophotometric assay for the HCV serine protease can be performed on the inventive compounds by following the procedure described by R. Zhang et al, *Analytical Biochemistry*, 270 (1999) 268-275, the disclosure of which is incorporated herein by reference. The assay based on the proteolysis of chromogenic ester substrates is suitable for the continuous monitoring of HCV NS3 protease activity. The substrates are derived from the P side of the NS5A-NS5B junction sequence (Ac-DTEDVVX(Nva), where X=A or P) (SEQ ID NO: 1) whose C-terminal carboxyl groups are esterified with one of four different chromophoric alcohols (3- or 4-nitrophenol, 7-hydroxy-4-methyl-coumarin, or 4-phenylazophenol). Illustrated below are the synthesis, characterization and application of these novel spectrophotometric ester substrates to high throughput screening and detailed kinetic evaluation of HCV NS3 protease inhibitors.

Materials and Methods:

Materials: Chemical reagents for assay related buffers are obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides are synthesized manually or on an automated ABI model 431A synthesizer (from Applied Biosystems). UV/VIS Spectrometer model LAMBDA 12 was from Perkin Elmer (Norwalk, Conn.) and 96-well UV plates were obtained from Corning (Corning, N.Y.). The prewarming block can be from USA Scientific (Ocala, Fla.) and the 96-well plate vortexer is from Labline Instruments (Melrose Park, Ill.). A Spectramax Plus microtiter plate reader with monochrometer is obtained from Molecular Devices (Sunnyvale, Calif.).

Enzyme Preparation: Recombinant heterodimeric HCV NS3/NS4A protease (strain 1a) is prepared by using the procedures published previously (D. L. Sali et al, *Biochemistry*, 37 (1998)

3392-3401). Protein concentrations are determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) is exchanged for the assay buffer (25 mM MOPS pH 6.5, 300 mM NaCl, 10% glycerol, 0.05% lauryl maltoside, 5 µM EDTA and 5 µM DTT) utilizing a Biorad Bio-Spin P-6 prepacked column.

Substrate Synthesis and Purification: The synthesis of the substrates is done as reported by R. Zhang et al, (ibid.) and is initiated by anchoring Fmoc-Nva-OH to 2-chlorotrityl chloride resin using a standard protocol (K. Barlos et al, *Int. J. Pept. Protein Res.*, 37 (1991), 513-520). The peptides are subsequently assembled, using Fmoc chemistry, either manually or on an automatic ABI model 431 peptide synthesizer. The N-acetylated and fully protected peptide fragments are cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash is evaporated azeotropically (or repeatedly extracted by aqueous $Na_2CO_3$ solution) to remove the acid used in cleavage. The DCM phase is dried over $Na_2SO_4$ and evaporated.

The ester substrates are assembled using standard acid-alcohol coupling procedures (K. Holmber et al, *Acta Chem. Scand.*, B33 (1979) 410-412). Peptide fragments are dissolved in anhydrous pyridine (30-60 mg/ml) to which 10 molar equivalents of chromophore and a catalytic amount (0.1 eq.) of para-toluenesulfonic acid (pTSA) were added. Dicyclohexylcarbodiimide (DCC, 3 eq.) is added to initiate the coupling reactions. Product formation is monitored by HPLC and can be found to be complete following 12-72 hour reaction at room temperature. Pyridine solvent is evaporated under vacuum and further removed by azeotropic evaporation with toluene. The peptide ester is deprotected with 95% TFA in DCM for two hours and extracted three times with anhydrous ethyl ether to remove excess chromophore. The deprotected substrate is purified by reversed phase HPLC on a C3 or C8 column with a 30% to 60% acetonitrile gradient (using six column volumes). The overall yield following HPLC purification can be approximately 20-30%. The molecular mass can be confirmed by electrospray ionization mass spectroscopy. The substrates are stored in dry powder form under desiccation.

Spectra of Substrates and Products: Spectra of substrates and the corresponding chromophore products are obtained in the pH 6.5 assay buffer. Extinction coefficients are determined at the optimal off-peak wavelength in 1-cm cuvettes (340 nm for 3-Np and HMC, 370 nm for PAP and 400 nm for 4-Np) using multiple dilutions. The optimal off-peak wavelength is defined as that wavelength yielding the maximum fractional difference in absorbance between substrate and product (product OD-substrate OD)/substrate OD).

Protease Assay: HCV protease assays are performed at 30° C. using a 200 µl reaction mix in a 96-well microtiter plate. Assay buffer conditions (25 mM MOPS pH 6.5, 300 mM NaCl, 10% glycerol, 0.05% lauryl maltoside, 5 µM EDTA and 5 µM DTT) are optimized for the NS3/NS4A heterodimer (D. L. Sali et al, ibid.)). Typically, 150 µl mixtures of buffer, substrate and inhibitor are placed in wells (final concentration of DMSO≦4% v/v) and allowed to preincubate at 30° C. for approximately 3 minutes. Fifty µls of prewarmed protease (12 nM, 30° C.) in assay buffer, is then used to initiate the reaction (final volume 200 µl). The plates are monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore is monitored at the appropriate wavelength against a no enzyme blank as a control for non-enzymatic hydrolysis. The evaluation of substrate kinetic parameters is performed over a 30-fold substrate concentration range (~6-200 µM). Initial velocities are determined using linear regression and kinetic constants are obtained by fitting the data to the Michaelis-Menten equation using non-linear regression analysis (Mac Curve Fit 1.1, K. Raner). Turnover numbers ($k_{cat}$) are calculated assuming the enzyme is fully active.

Evaluation of Inhibitors and Inactivators: The inhibition constants ($K_i$) for the competitive inhibitors Ac-D-(D-Gla)-L-I-(Cha)-C-OH (27) (SEQ ID NO: 2), Ac-DTEDVVA(Nva)-OH (SEQ ID NO: 3) and Ac-DTEDVVP(Nva)-OH (SEQ ID NO: 4) are determined experimentally at fixed concentrations of enzyme and substrate by plotting $v_o/v_i$ vs. inhibitor concentration ($[I]_o$) according to the rearranged Michaelis-Menten equation for competitive inhibition kinetics: $v_o/v_i=1+[I]_o/(K_i(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data are fitted using linear regression and the resulting slope, $1/(K_i(1+[S]_o/K_m)$, is used to calculate the $K_i$ value. The obtained Ki* values (in nanoMolar) for some of the inventive compounds are shown below in Table 2.

TABLE 2

| Compound structure | Ki (nM) |
|---|---|
| (structure shown) | 9 |

TABLE 2-continued

| Compound structure | Ki (nM) |
|---|---|
| | 7 |
| | 7 |

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound, or enantiomers, stereoisomers, rotamers, tautomers, and racemates of said compound, said compound having the general structure shown in Formula I:

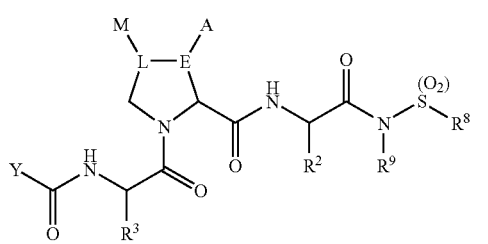

Formula I or a pharmaceutically acceptable salt, solvate or ester thereof, wherein:

$R^8$ is selected from the group consisting of alkyl-, aryl-, heteroalkyl-, heteroaryl-, cycloalkyl-, heterocyclyl-, arylalkyl-, heteroarylalkyl-, and heterocyclylalkyl-;

$R^9$ is selected from the group consisting of H, alkyl, alkenyl, alkynyl, aryl and cycloalkyl;

A and M can be the same or different, each being independently selected from R, OR, N(H)R, N(RR'), SR, S(O$_2$)R, and halo; or A and M are connected to each other (in other words, A-E-L-M taken together) such that the moiety:

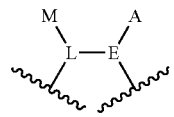

shown above in Formula I forms either a three, four, five, six, seven or eight-membered cycloalkyl, a four to eight-membered heterocyclyl, a six to ten-membered aryl, or a five to ten-membered heteroaryl;

E is C(H) or C(R);

L is C(H), C(R), CH$_2$C(R), or C(R)CH$_2$;

R and R' can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in N(RR') are connected to each other such that N(RR') forms a four to eight-membered heterocyclyl;

R$^2$ and R$^3$ can be the same or different, each being independently selected from the group consisting of H, alkyl, heteroalkyl, alkenyl, heteroalkenyl, alkynyl, heteroalkynyl, cycloalkyl, spiro-linked cycloalkyl, heterocyclyl, aryl, arylalkyl, heteroaryl, and heteroarylalkyl;

Y is selected from the following moieties:

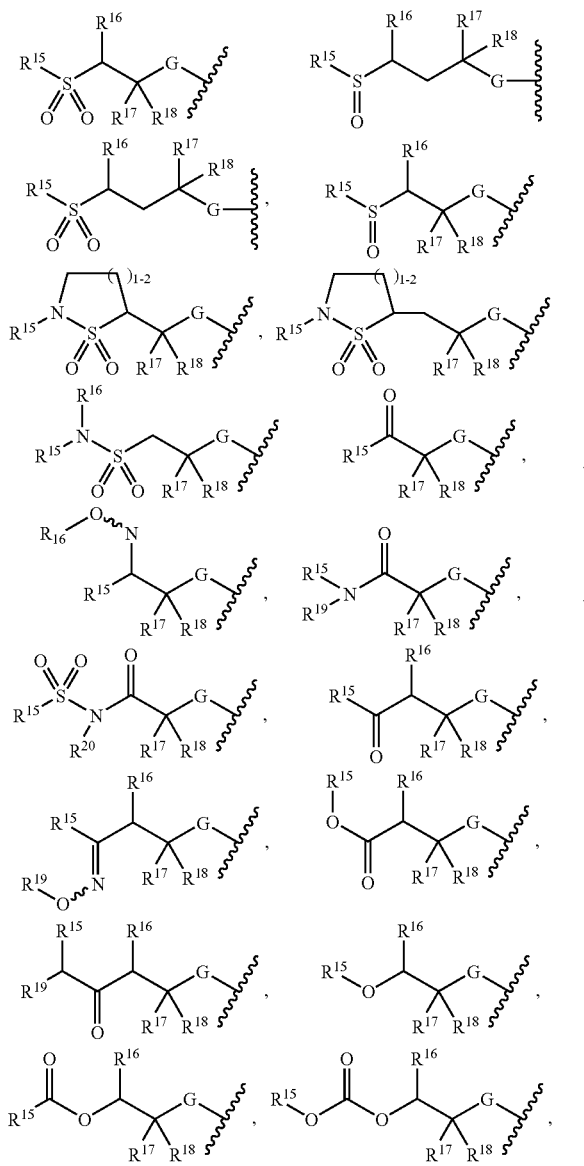

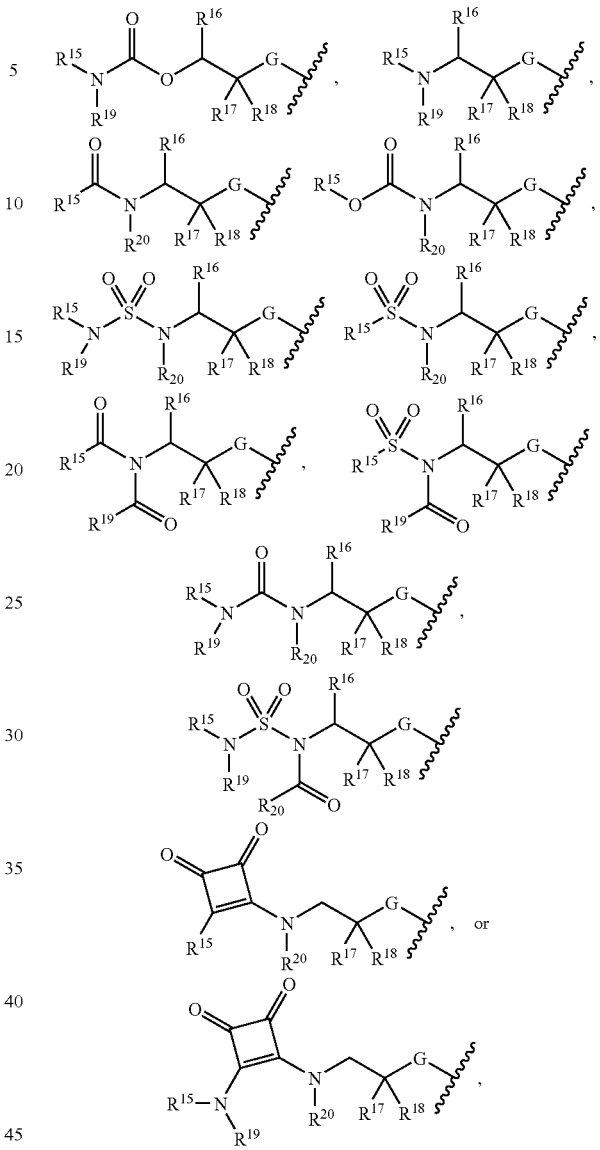

wherein G is NH; and R$^{15}$, R$^{16}$, R$^{17}$, R$^{18}$, R$^{19}$ and R$^{20}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) R$^{17}$ and R$^{18}$ are independently connected to each other to form a three to eight-membered cycloalkyl or heterocyclyl; (ii) likewise independently R$^{15}$ and R$^{19}$ are connected to each other to form a four to eight-membered heterocyclyl; (iii) likewise independently R$^{15}$ and R$^{16}$ are connected to each other to form a four to eight-membered heterocyclyl; and (iv) likewise independently R$^{15}$ and R$^{20}$ are connected to each other to form a four to eight-membered heterocyclyl;

wherein each of said alkyl, aryl, heteroaryl, cycloalkyl, spiro-linked cycloalkyl, and heterocyclyl can be unsubstituted or optionally independently substituted with one or more moieties independently selected from the group consisting of hydroxy, alkoxy, aryloxy, thio, alkylthio, arylthio, amino, amido, alkylamino, arylamino, alkylsulfonyl, arylsulfonyl, sulfonamido, alkyl, alkenyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

2. The compound of claim 1, wherein $R^8$ is selected from the group consisting of alkyl-, aryl-, heteroaryl-, cycloalkyl-, arylalkyl- and heteroarylalkyl-.

3. The compound of claim 2, wherein $R^8$ is an aryl or cycloalkyl.

4. The compound of claim 3, wherein $R^8$ is phenyl or cyclopropyl.

5. The compound of claim 1, wherein $R^9$ is H, alkyl, alkenyl or cycloalkyl.

6. The compound of claim 1, wherein $R^9$ is H, methyl, allyl or cyclopropyl.

7. The compound of claim 1, wherein $R^2$ is selected from the group consisting of the following moieties:

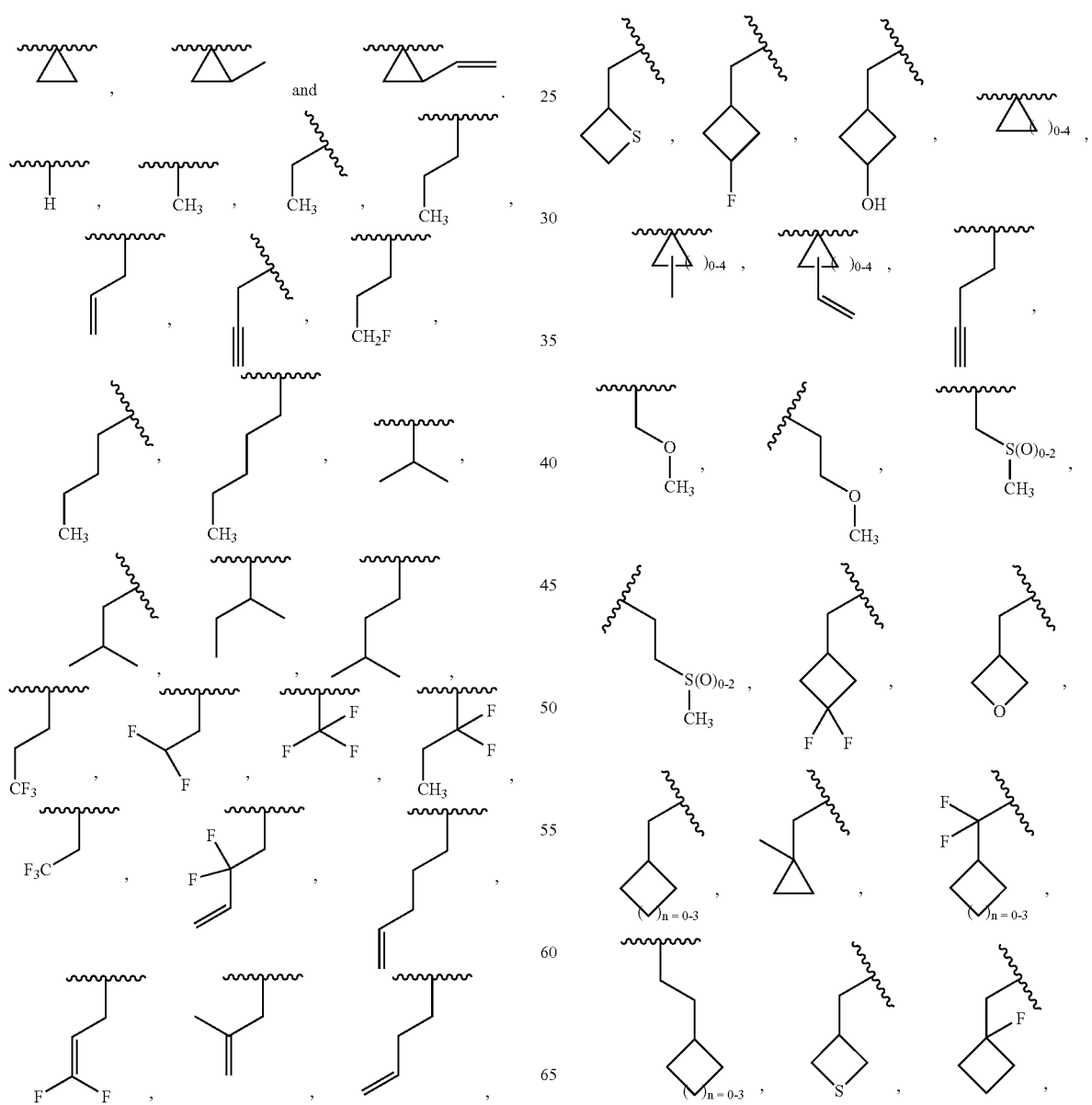

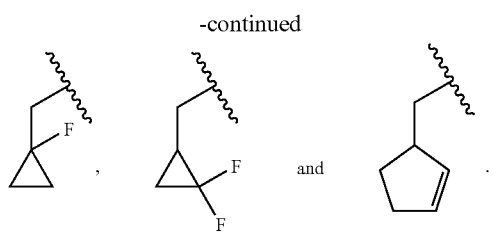
8. The compound of claim 7, wherein $R^2$ is selected from the group consisting of:
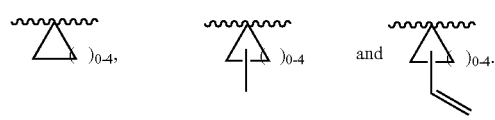
9. The compound of claim 1, wherein $R^3$ is selected from the group consisting of:
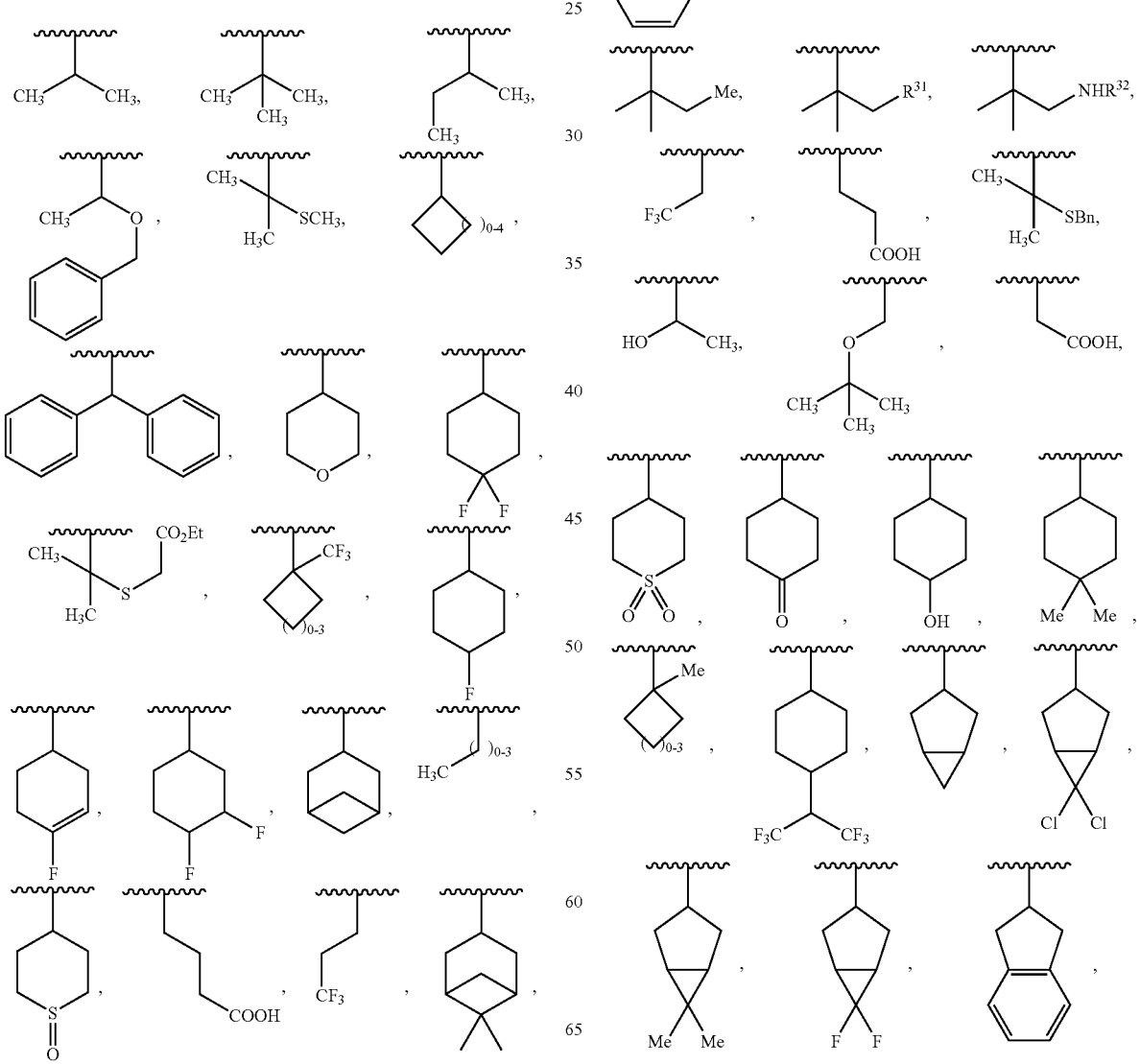
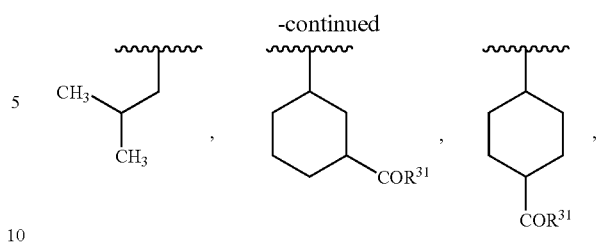

-continued
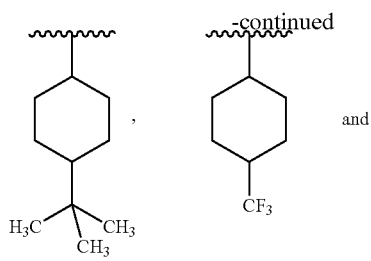
wherein R³¹ is OH or O-alkyl; and
R³² is H, C(O)CH₃, C(O)OtBu or C(O)N(H)tBu.
10. The compound of claim 9, wherein R³ is selected from the group consisting of the following moieties:
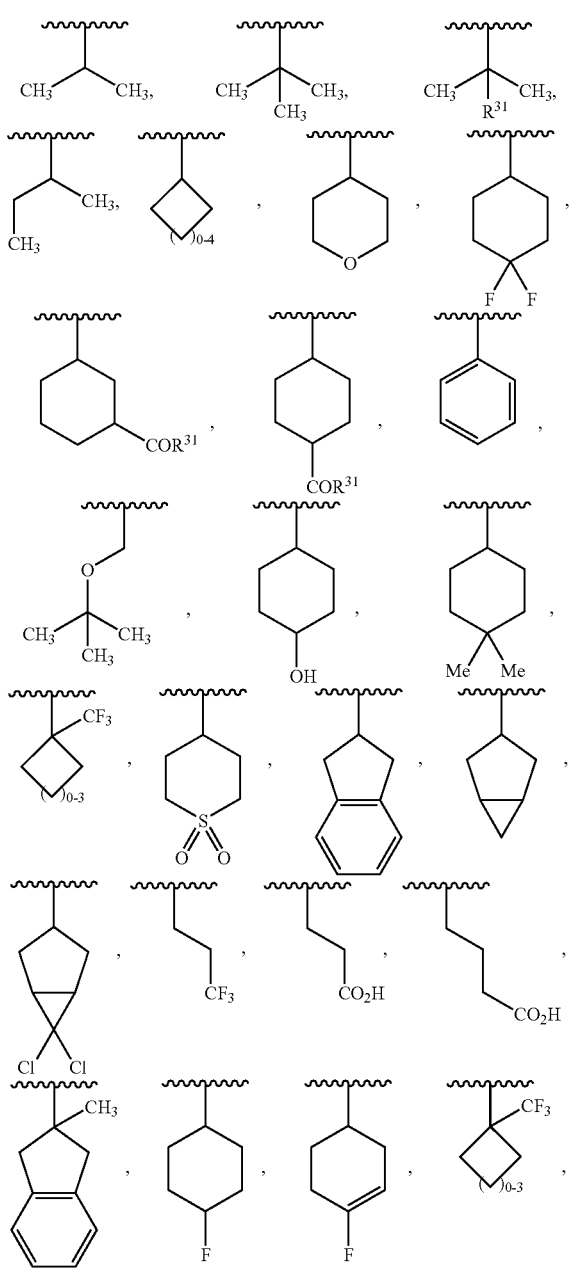
-continued
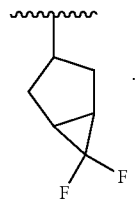
11. The compound of claim 1, wherein G is NH.
12. The compound of claim 1, wherein Y is selected from the following moieties:
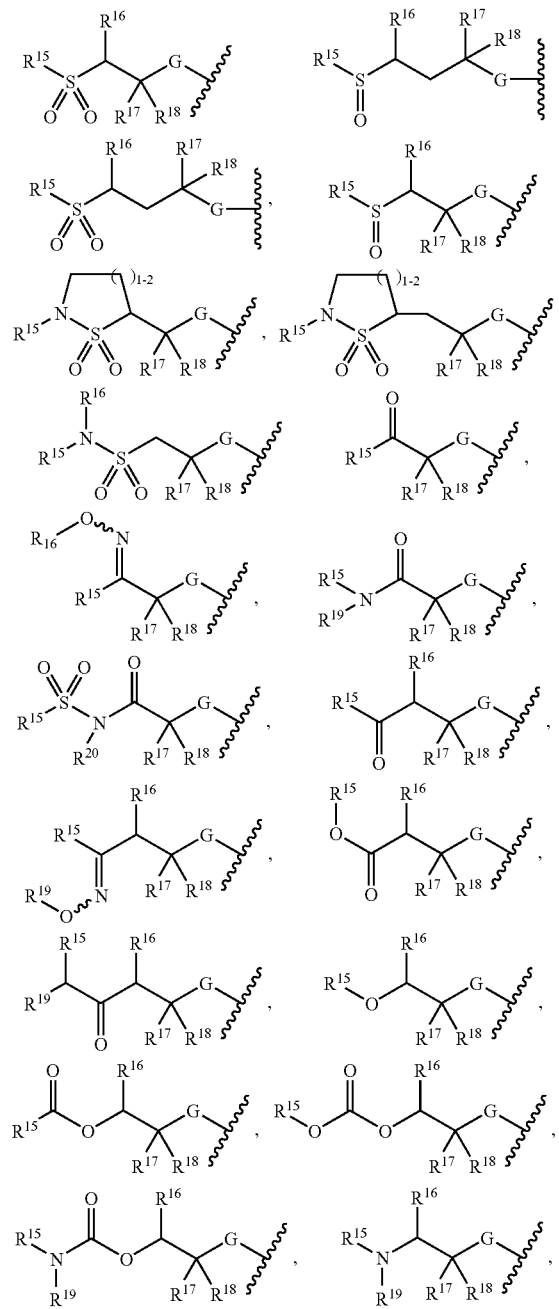

-continued

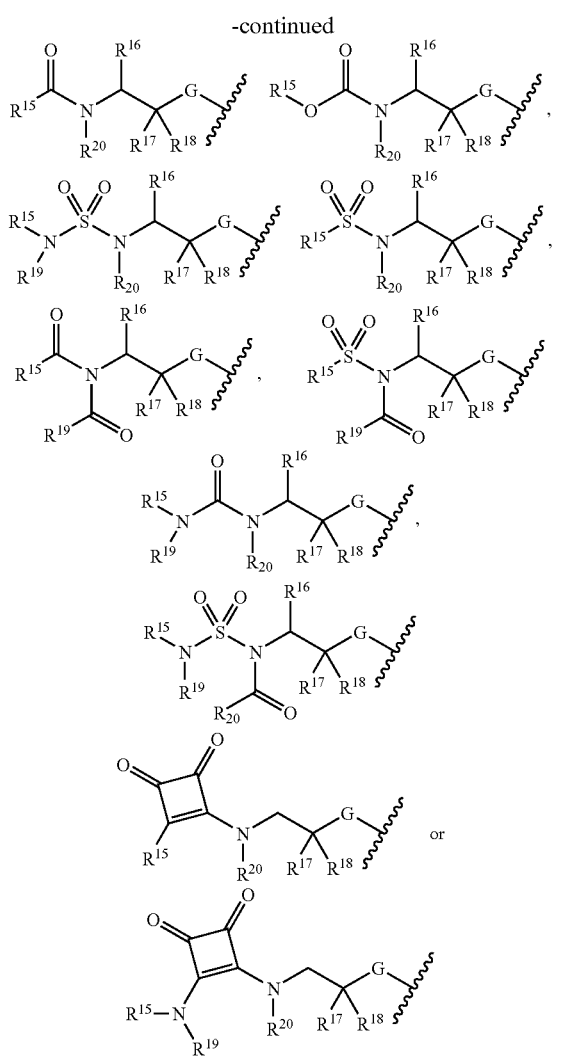

wherein $R^{15}$, $R^{16}$, $R^{17}$, $R^{18}$, $R^{19}$ and $R^{20}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, alkenyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

13. The compound of claim 12, wherein the moiety:

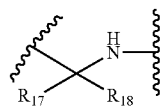

is selected from the following:

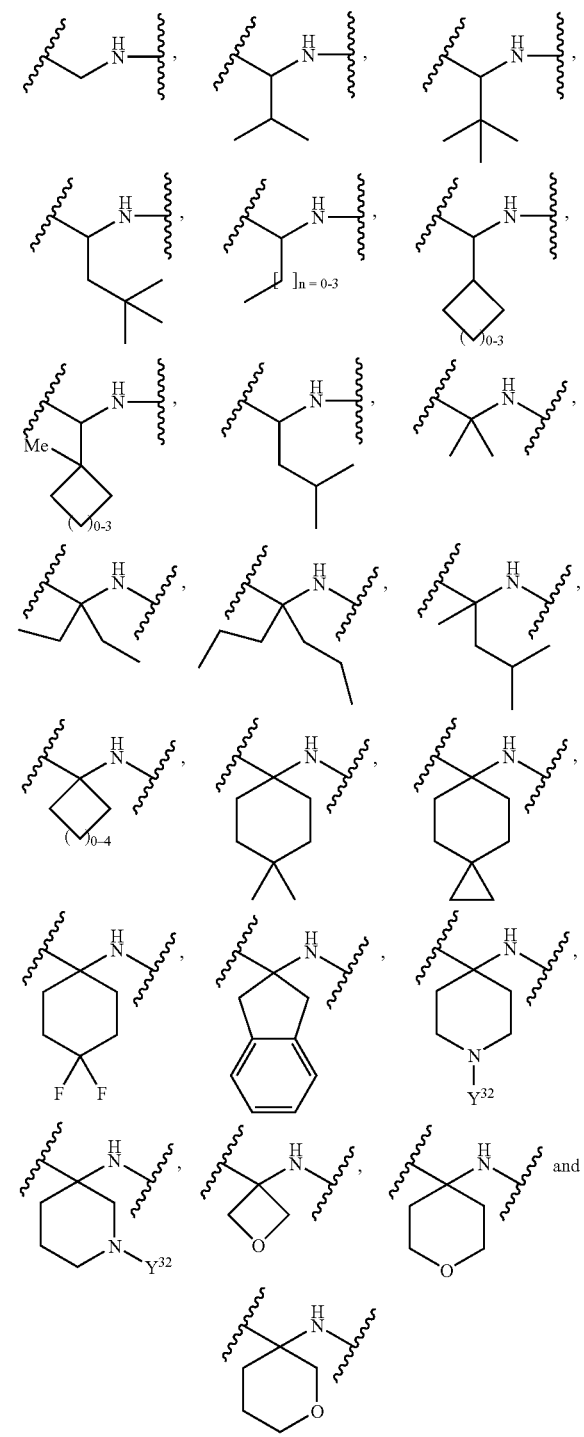

wherein $Y^{32}$ is selected from the group consisting of:
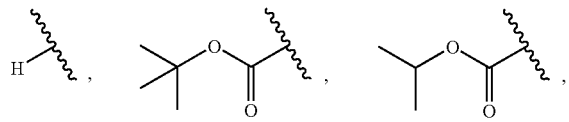
14. The compound of claim 12, wherein Y is selected from:
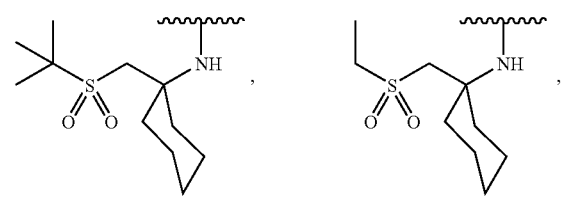
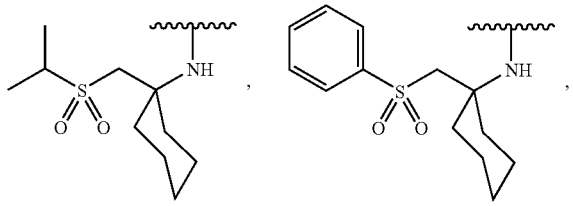
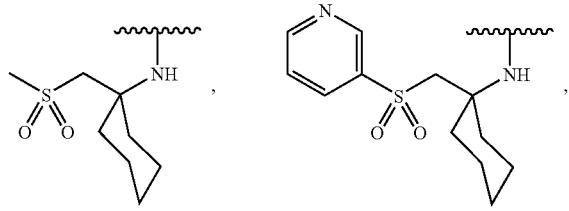
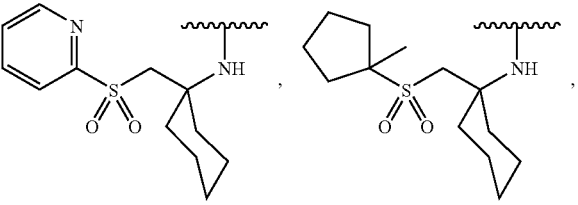
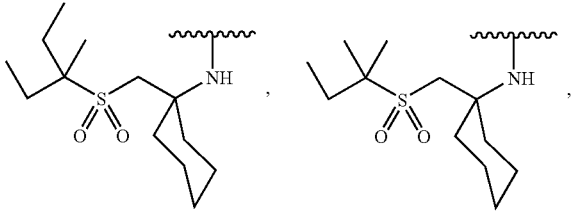
-continued
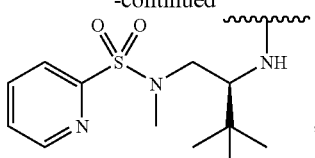
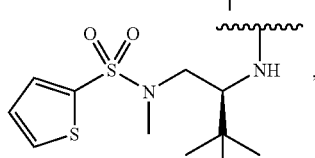
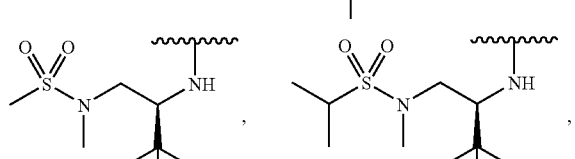
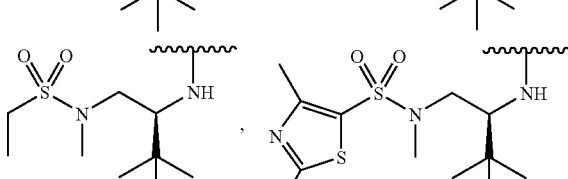
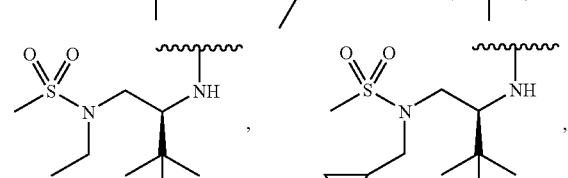
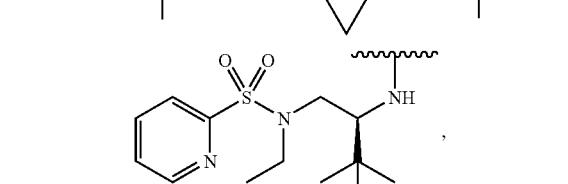
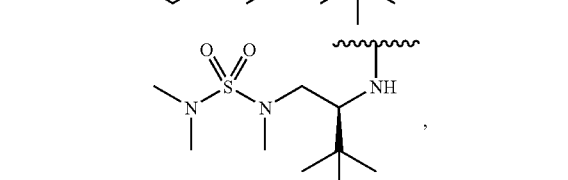
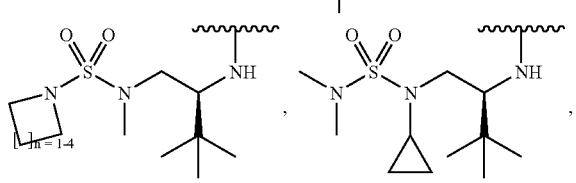
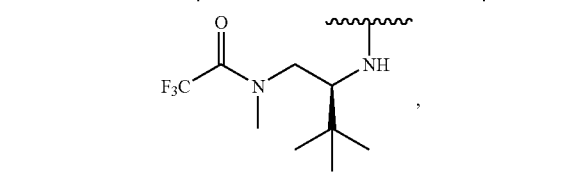
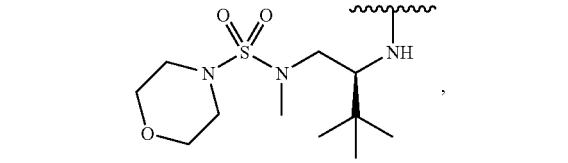

107
-continued
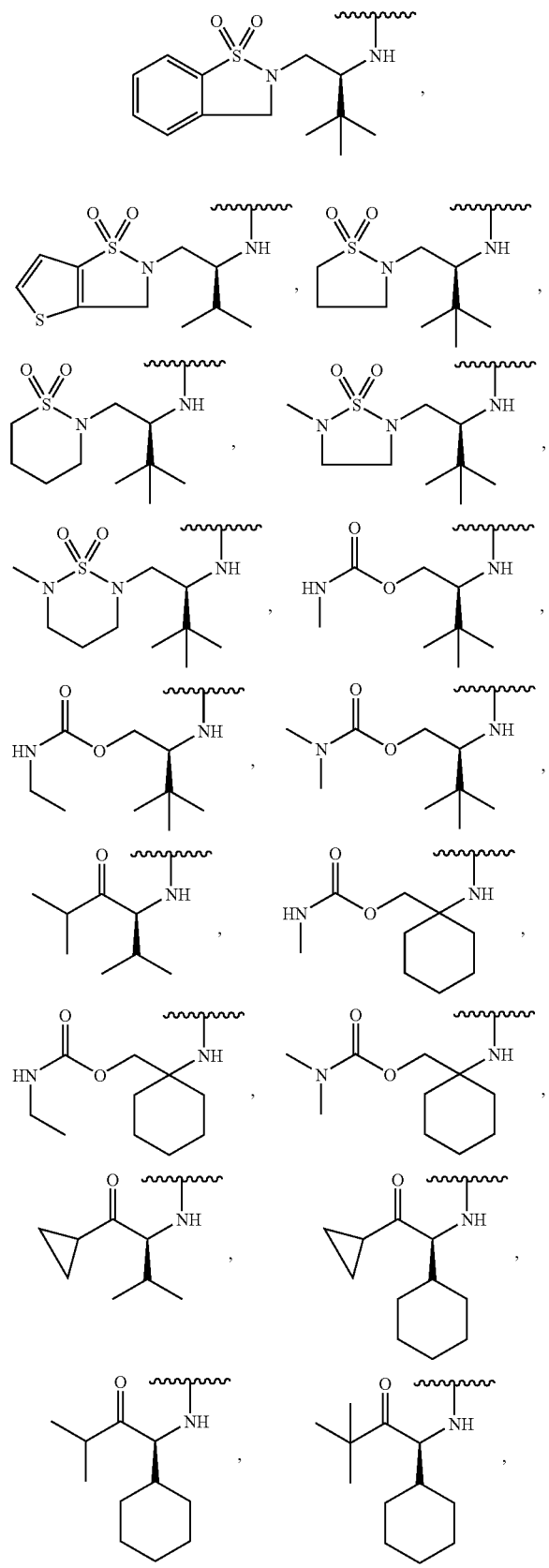
108
-continued
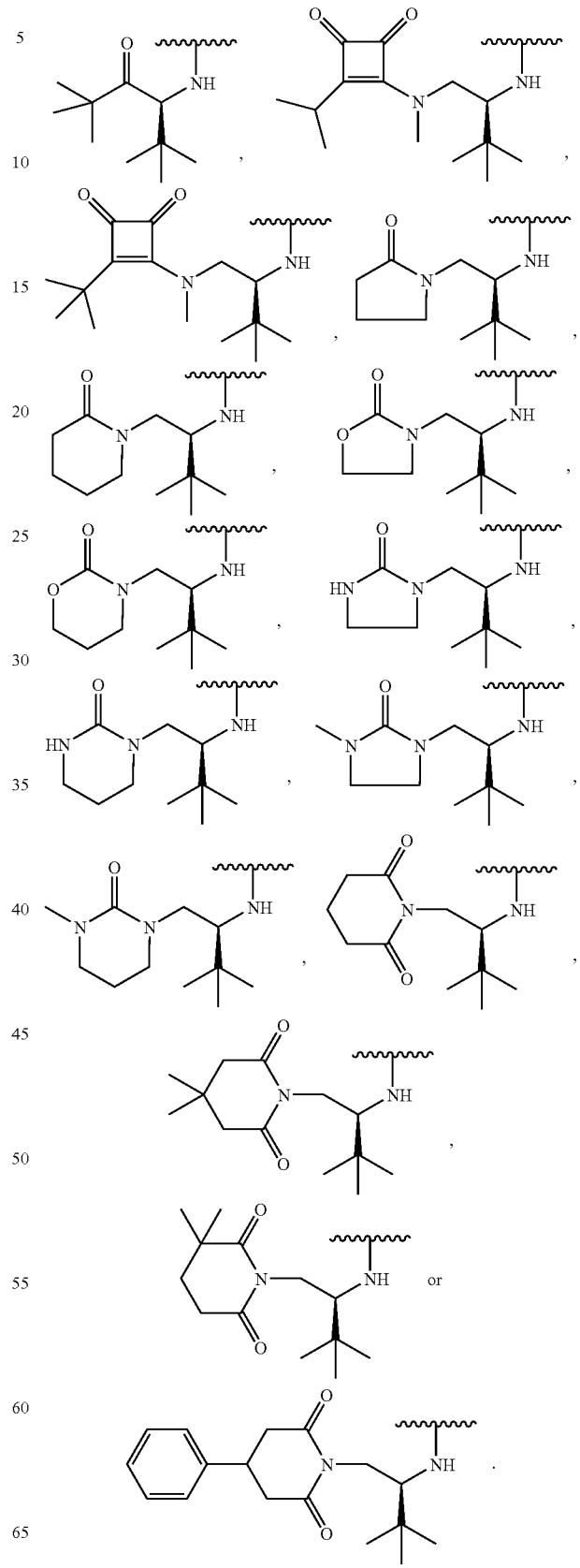

15. The compound of claim 1, wherein the moiety:
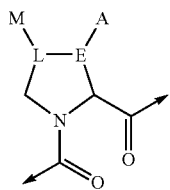
is selected from the following structures:
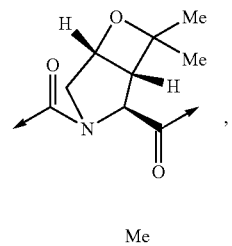 , 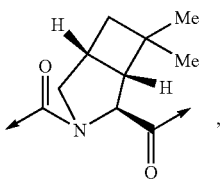 ,
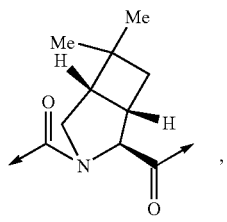 , 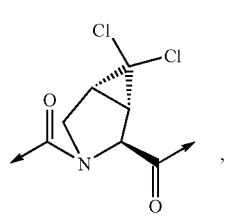 ,
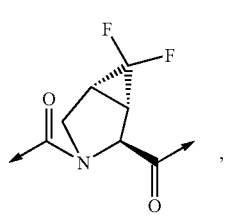 , 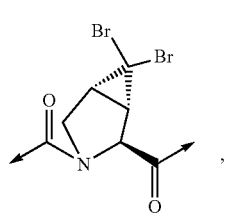 ,
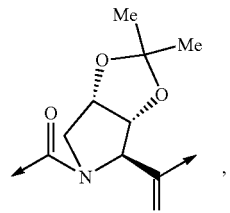 , 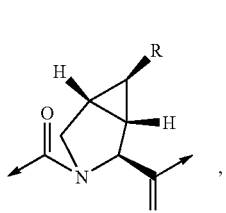 ,
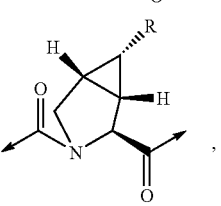 , 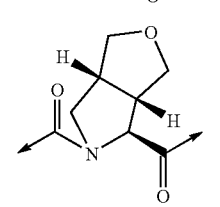 ,
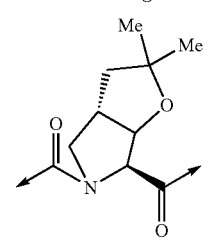 , 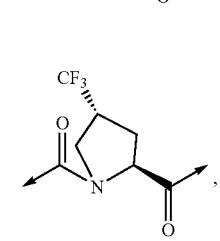 ,
-continued
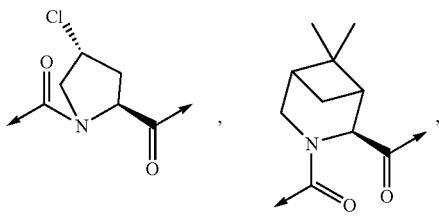
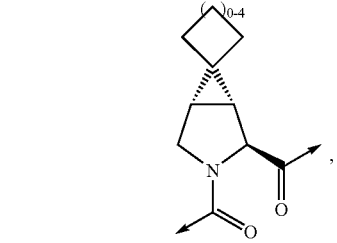
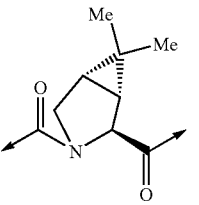 , 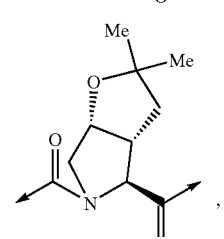 ,
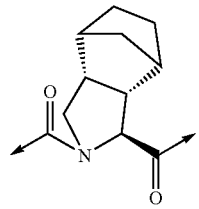 , 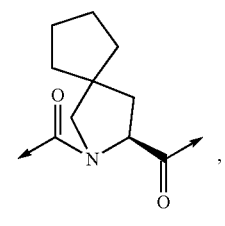 ,
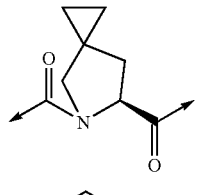 , 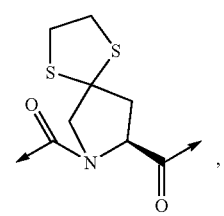 ,
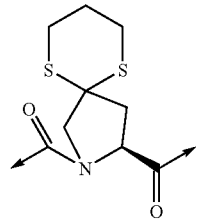 , 
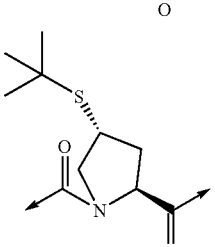 , 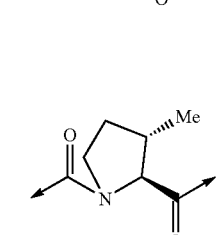

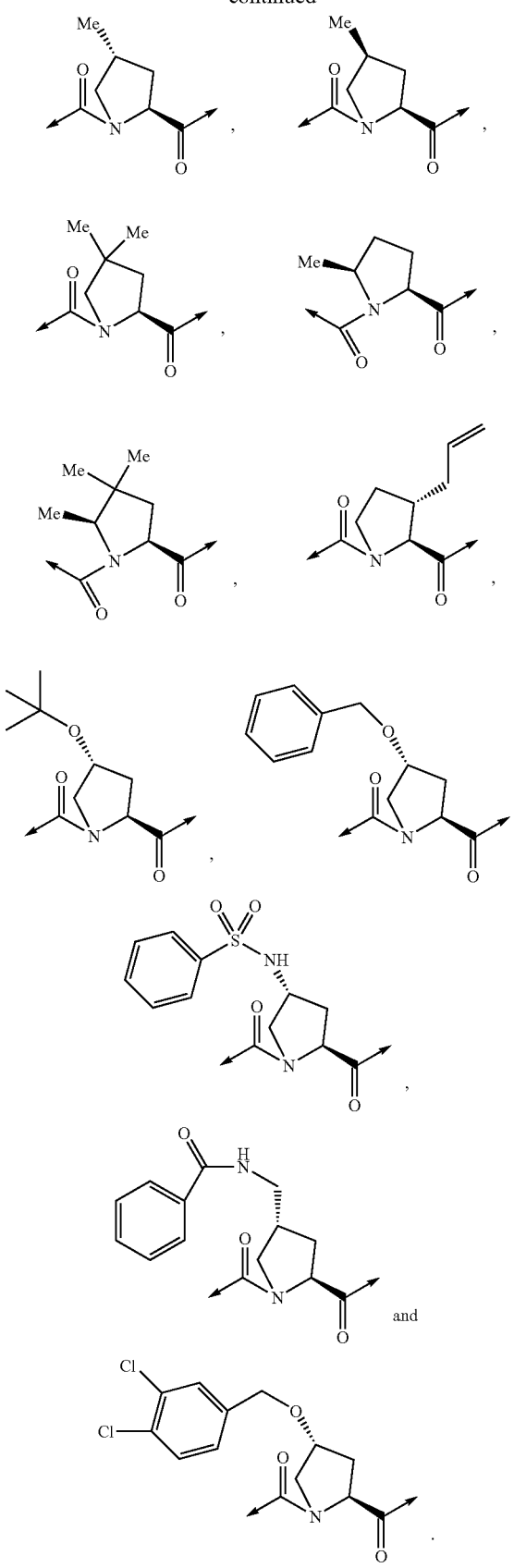
16. The compound of claim 15, wherein the moiety:
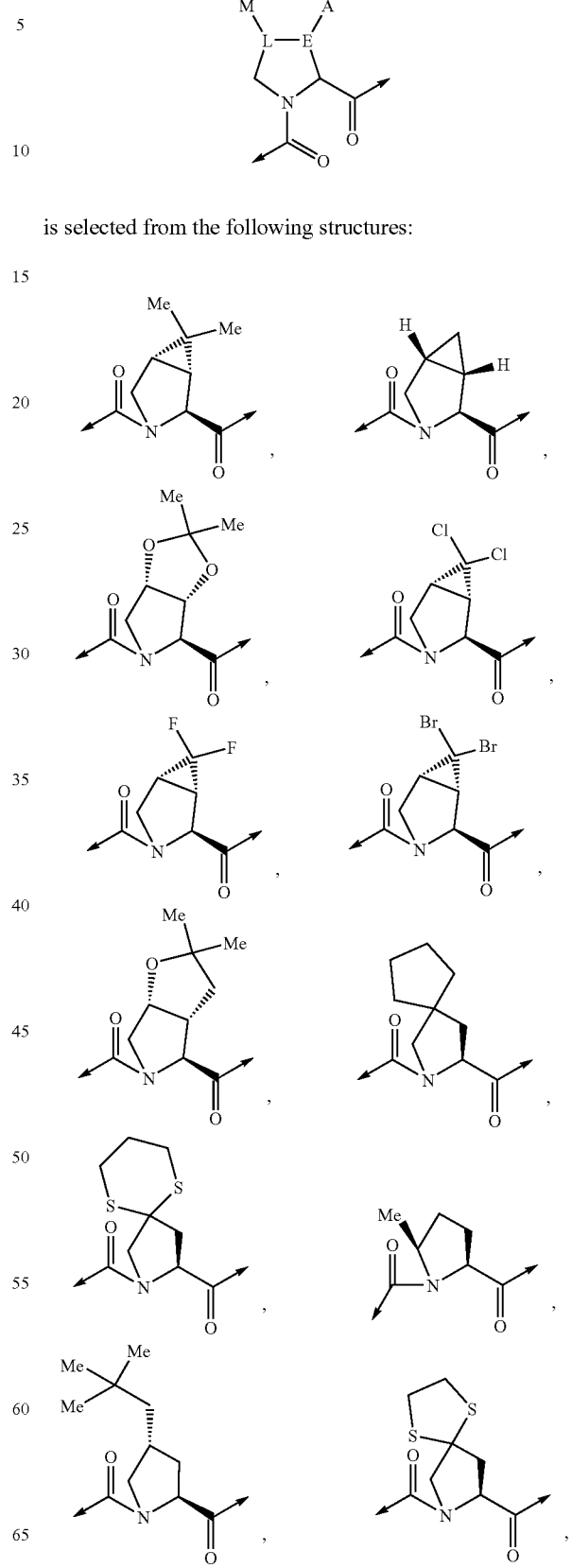
is selected from the following structures:

-continued
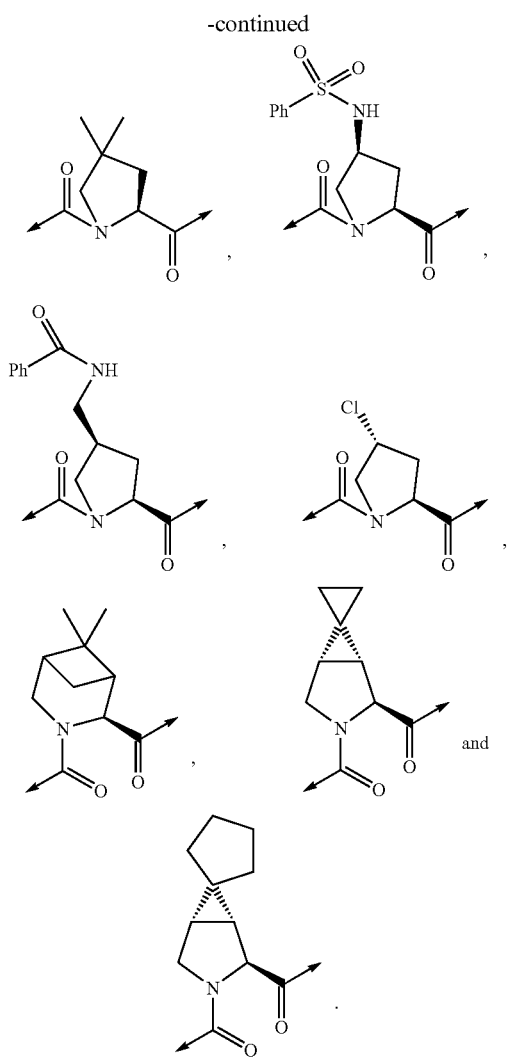
17. The compound of claim 16, wherein the moiety:
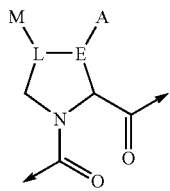
is selected from the following structures:
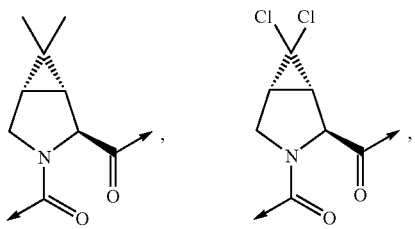
-continued
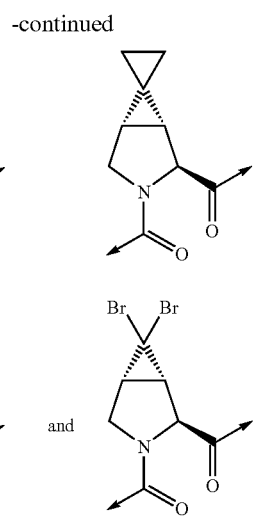
18. The compound of claim 1, wherein $R^8$ is phenyl or cyclopropyl;
$R^9$ is H, methyl, allyl or cyclopropyl;
$R^2$ is selected from the group consisting of the following moieties:
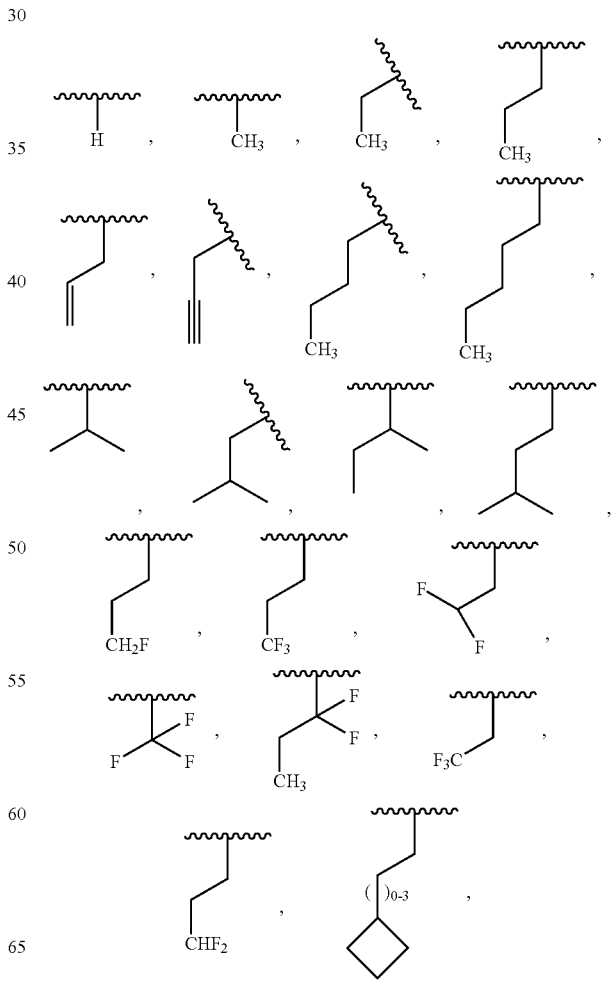

-continued
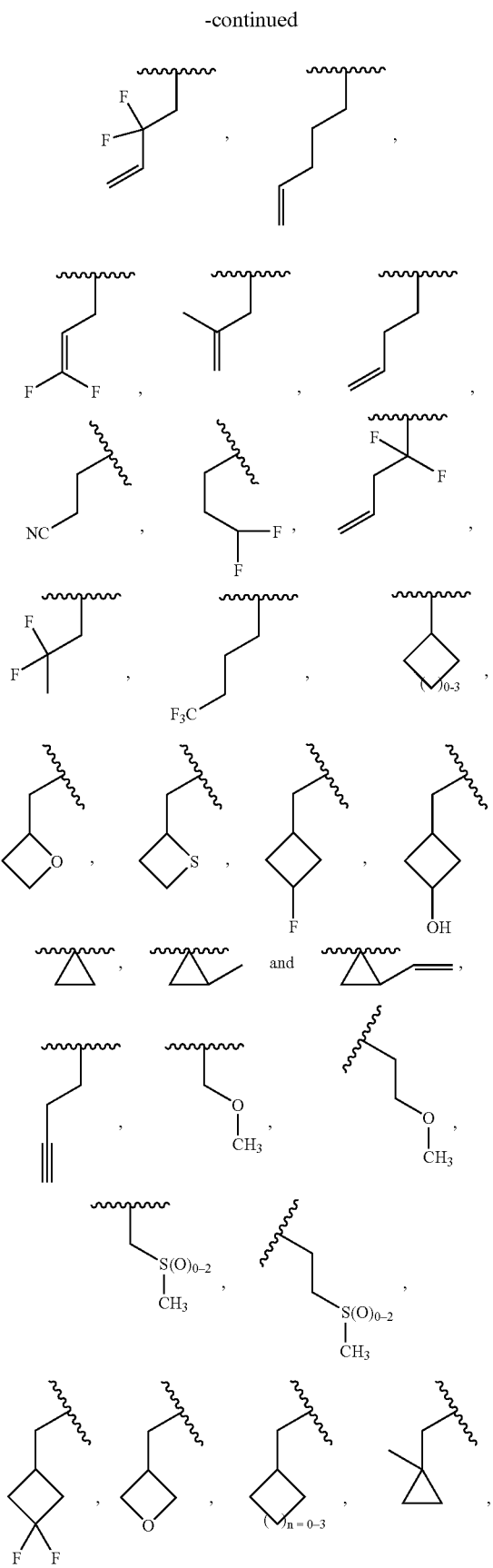
R³ is selected from the group consisting of the following moieties:
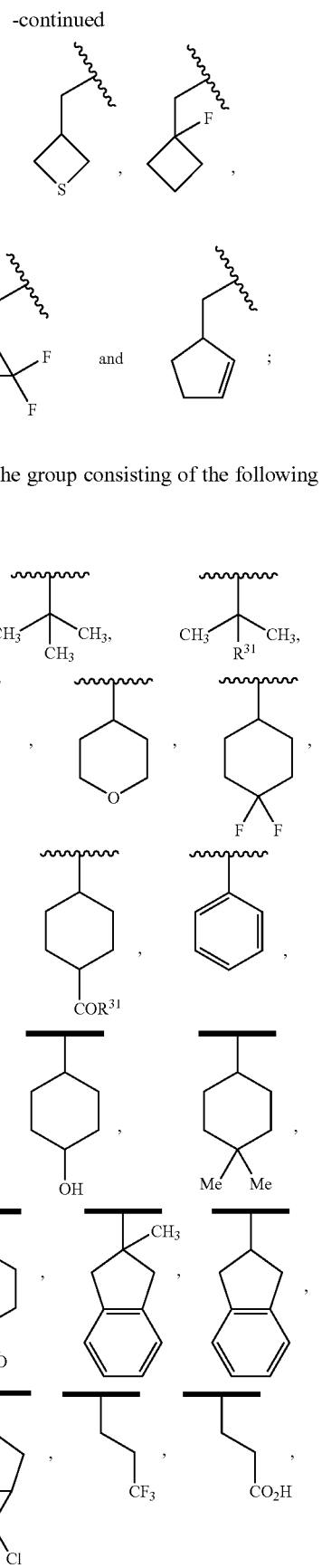

-continued
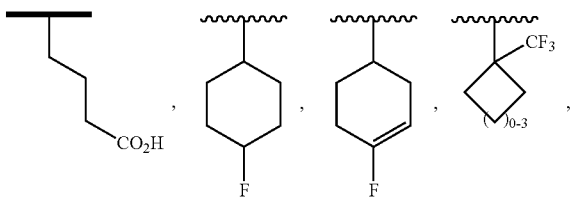
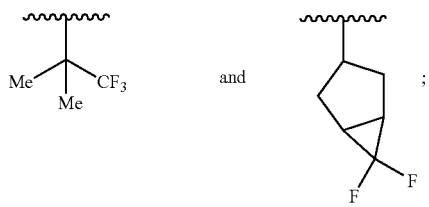
the moiety:
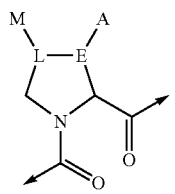
is:
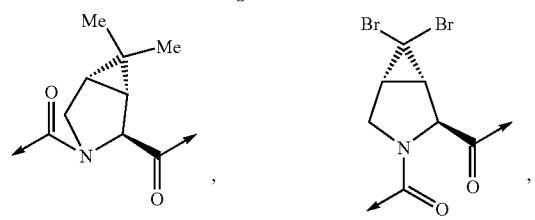
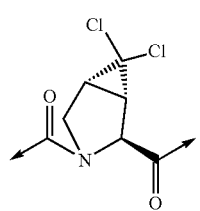, 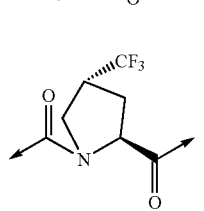,
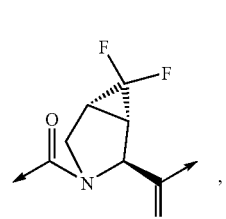, 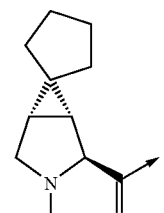,
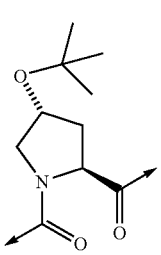, 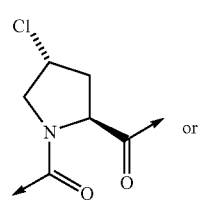 or
-continued
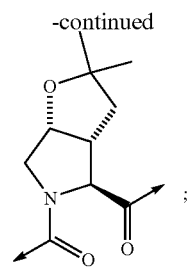;
and Y is selected from:
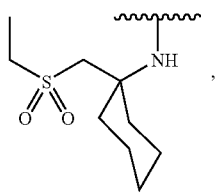
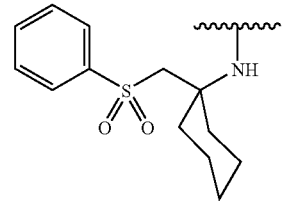
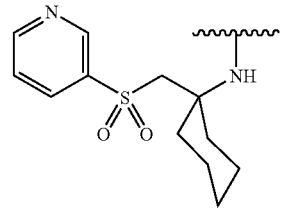
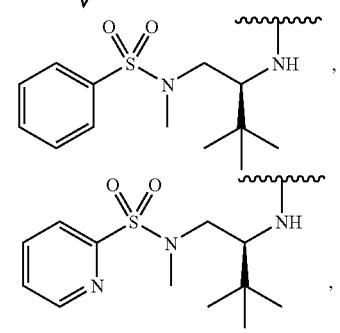

-continued
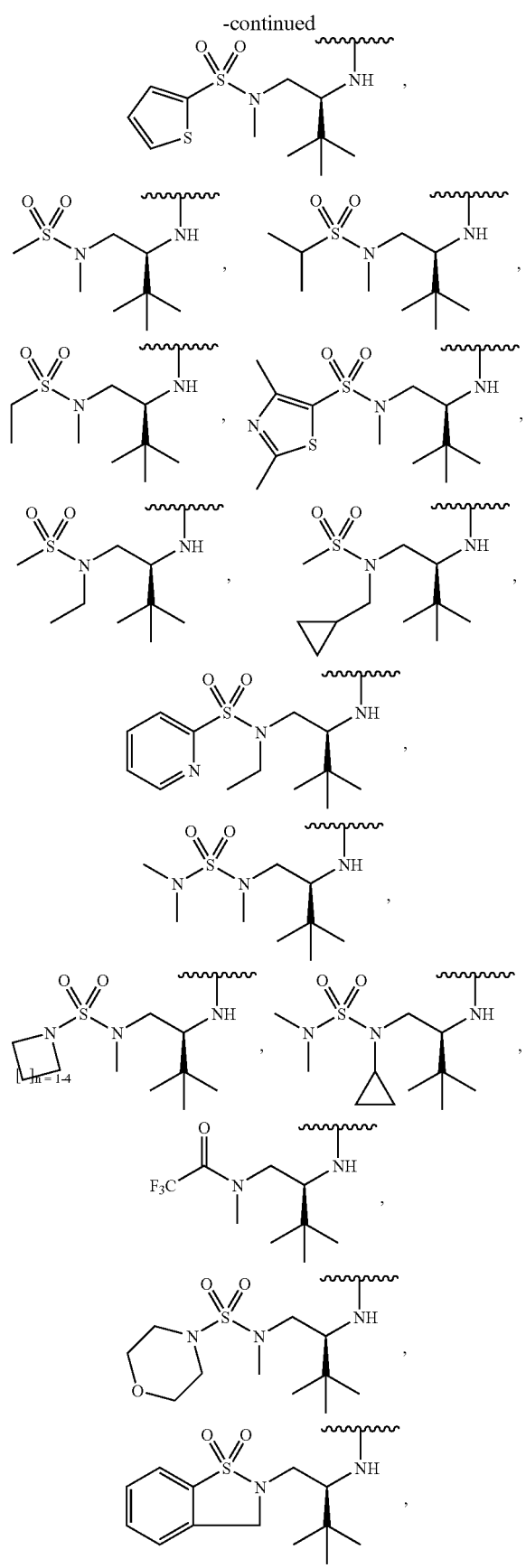
-continued
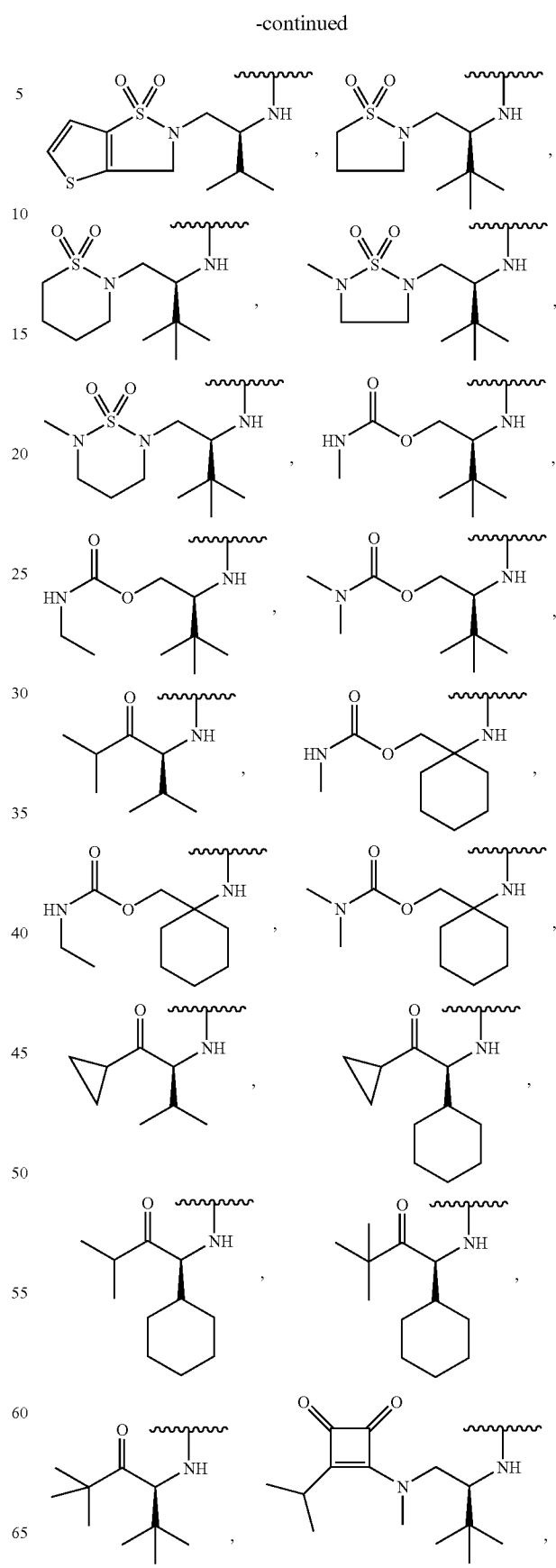

-continued

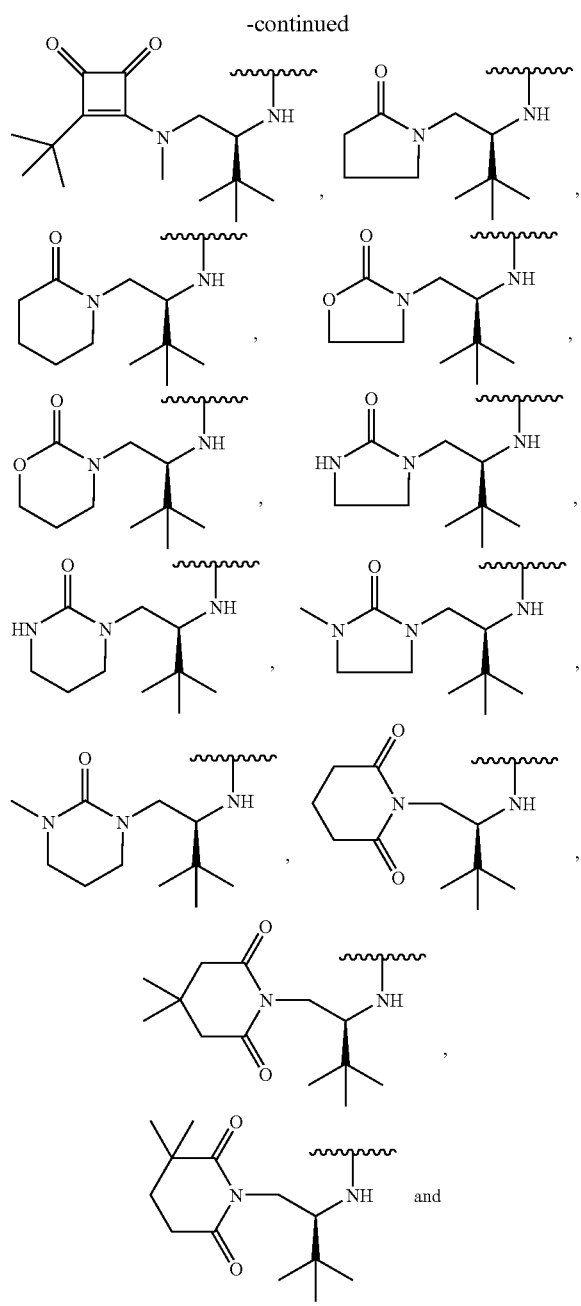

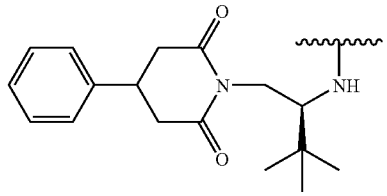

19. A pharmaceutical composition comprising as an active ingredient at least one compound of claim 1 additionally comprising at least one pharmaceutically acceptable carrier.

20. The pharmaceutical composition of claim 19, additionally containing at least one antiviral agent.

21. The pharmaceutical composition of claim 20, additionally containing at least one interferon.

22. The pharmaceutical composition of claim 21, wherein said at least one antiviral agent is ribavirin and said at least one interferon is α-interferon or pegylated interferon.

23. A method of treating HCV infection, said method comprising administering to a patient in need of such treatment a pharmaceutical composition which comprises therapeutically effective amounts of at least one compound of claim 1 and a pharmaceutically acceptable carrier thereof.

24. The method of claim 23, wherein said administration is oral or subcutaneous.

25. A method of treating HCV infection, said method comprising administering to a patient in need of such treatment therapeutically effective amounts of at least one compound of claim 1 and therapeutically effective amounts of at least one antiviral agent.

26. The method of claim 25, wherein said at least one compound and said at least one antiviral agent are administered simultaneously, concurrently or sequentially.

27. The method of claim 25, wherein said at least one compound and said at least one antiviral agent are administered in different amounts or in a fixed dose said fixed dose containing fixed amount of said at least one compound and fixed amount of said at least one antiviral agent.

28. The method of claim 25, wherein said administration is oral or subcutaneous.

29. A compound exhibiting HCV protease inhibitory activity, or enantiomers, stereoisomers, rotamers, tautomers, and racemates of said compound, or a pharmaceutically acceptable salt, solvate or ester of said compound, said compound being selected from the compounds of structures listed below:

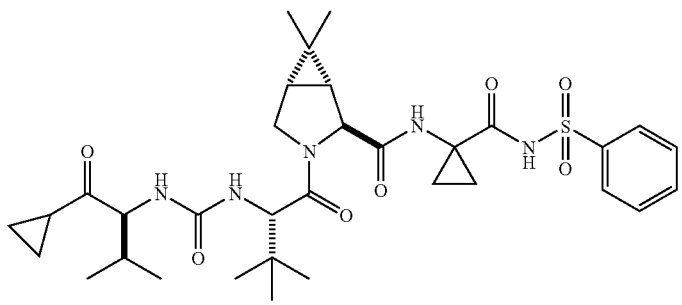

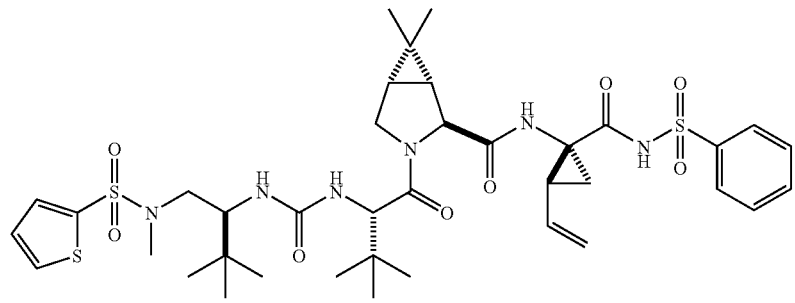
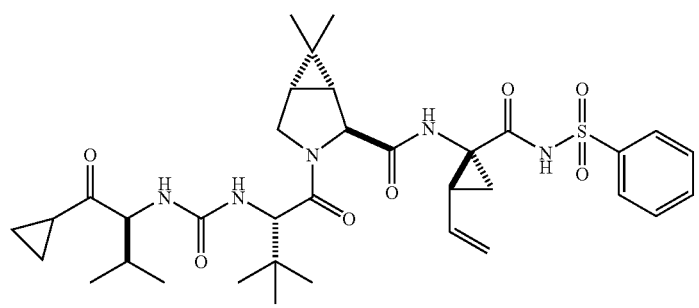
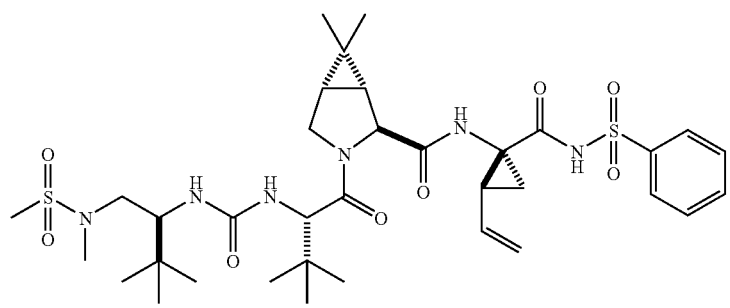
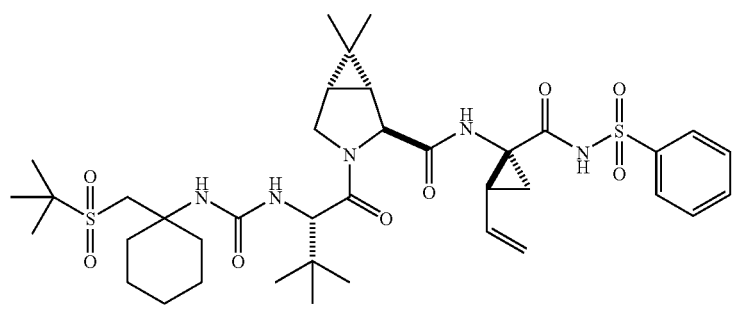

-continued

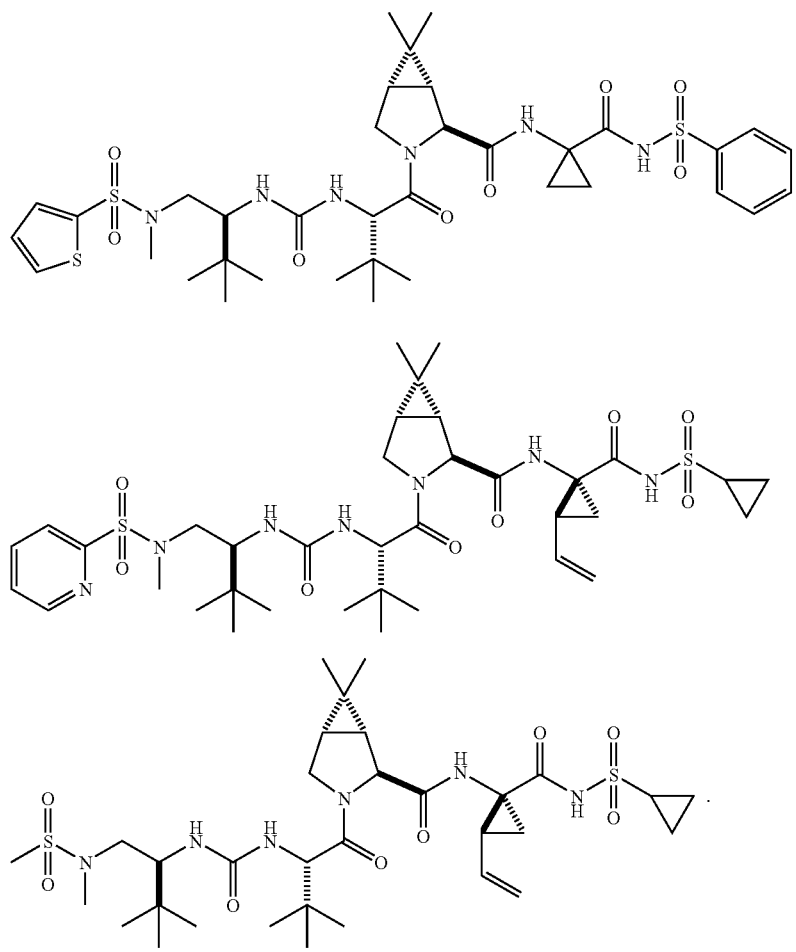

30. A pharmaceutical composition for treating a HCV infection, said composition comprising therapeutically effective amount of one or more compounds in claim 29 and a pharmaceutically acceptable carrier.

31. The pharmaceutical composition of claim 30, additionally containing at least one antiviral agent.

32. The pharmaceutical composition of claim 31, additionally containing at least one interferon or PEG-interferon alpha conjugate.

33. The pharmaceutical composition of claim 32, wherein said at least one antiviral agent is ribavirin and said at least one interferon is α-interferon.

34. A method of treatment of a hepatitis C virus infection, comprising administering an effective amount of one or more compounds of claim 29 to a person in need thereof.

35. A method of treating, or ameliorating one or more symptoms of hepatitis C, comprising administering a therapeutically effective amount of one or more compounds of claim 29 to a mammal in need thereof.

36. A compound of claim 1 in isolated and purified form.

37. A compound, or enantiomers, stereoisomers, rotamers, tautomers, and racemates of said compound, said compound having the general structure shown in Formula II:

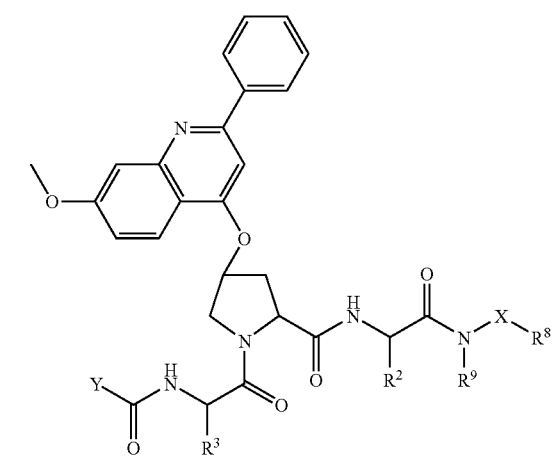

or a pharmaceutically acceptable salt, solvate or ester thereof, wherein:

$R^8$ is selected from the group consisting of alkyl-, aryl-, heteroalkyl-, heteroaryl-, cycloalkyl-, heterocyclyl-, arylalkyl-, heteroarylalkyl-, spiro-linked cycloalkyl, and heterocyclylalkyl;

$R^9$ is selected from the group consisting of H, alkyl, alkenyl, alkynyl, aryl and cycloalkyl;

X is S(O) or $S(O_2)$;

$R^2$ is selected from the group consisting of H, alkyl, heteroalkyl, alkenyl, heteroalkenyl, alkynyl, heteroalkynyl, non-spiro-linked cycloalkyl, heterocyclyl, aryl, arylalkyl, heteroaryl, and heteroarylalkyl;

$R^3$ is selected from the group consisting of H, alkyl, heteroalkyl, alkenyl, heteroalkenyl, alkynyl, heteroalkynyl, cycloalkyl, spiro-linked cycloalkyl, heterocyclyl, aryl, arylalkyl, heteroaryl, and heteroarylalkyl;

Y is selected from the following moieties:

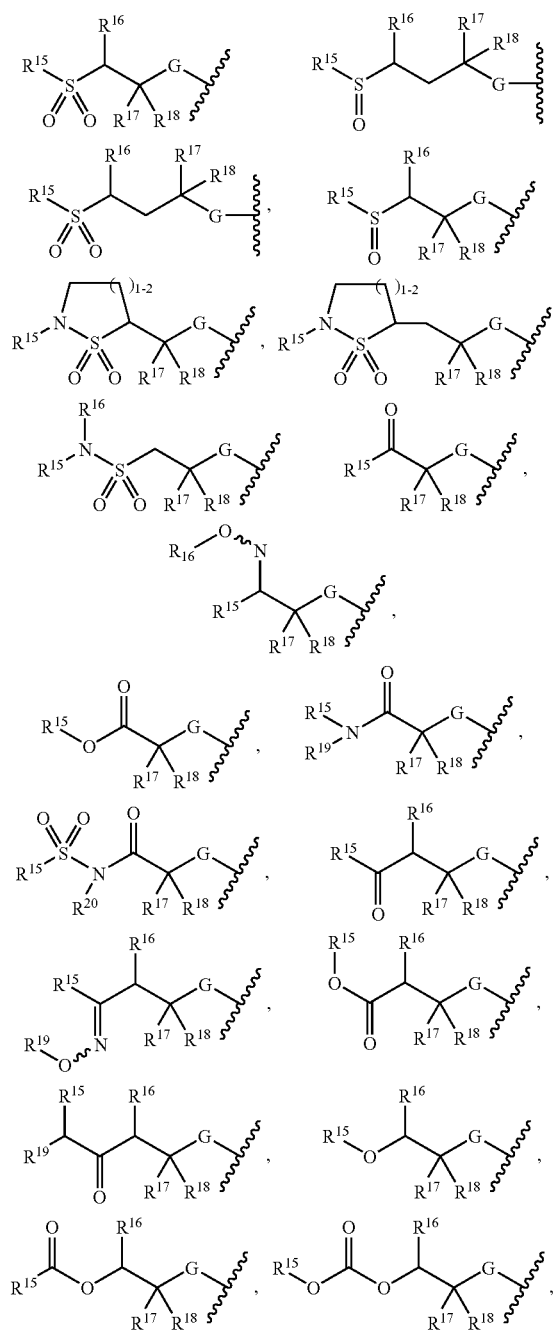

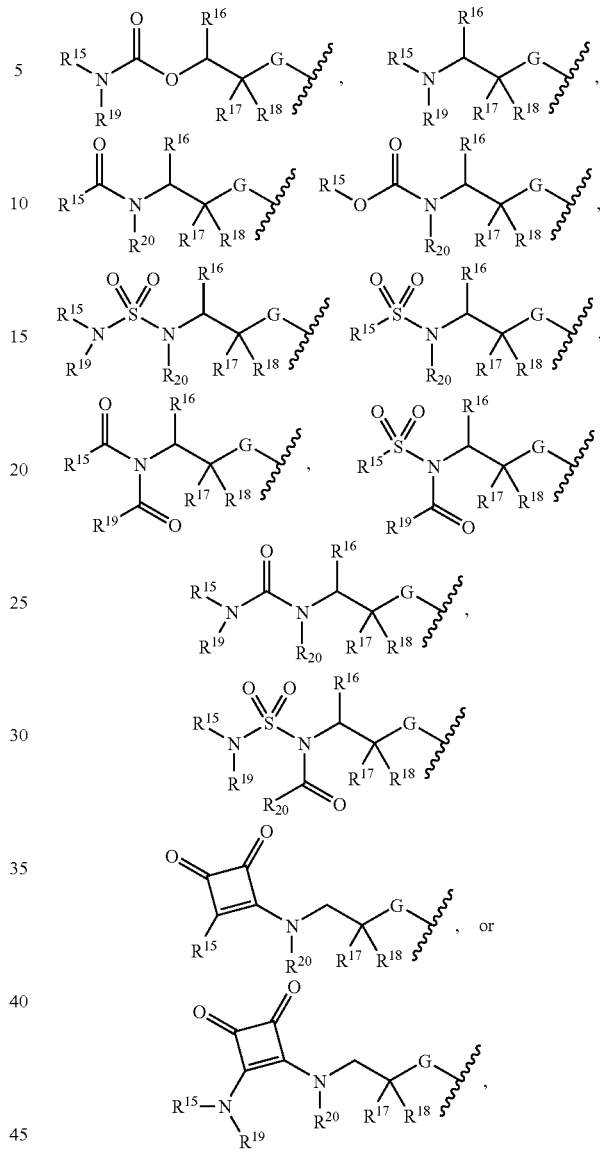

wherein G is NH; and $R^{15}$, $R^{16}$, $R^{17}$, $R^{18}$, $R^{19}$ and $R^{20}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl or heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, alkenyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

38. The compound of claim 37, wherein $R^8$ is selected from the group consisting of alkyl-, aryl-, heteroaryl-, cycloalkyl-, arylalkyl- and heteroarylalkyl-.

39. The compound of claim 38, wherein $R^8$ is aryl or cycloalkyl.

40. The compound of claim 39, wherein $R^8$ is phenyl or cyclopropyl.

41. The compound of claim 37, wherein $R^9$ is H, methyl, allyl or cyclopropyl.

42. The compound of claim 37, wherein $R^2$ is selected from the group consisting of:

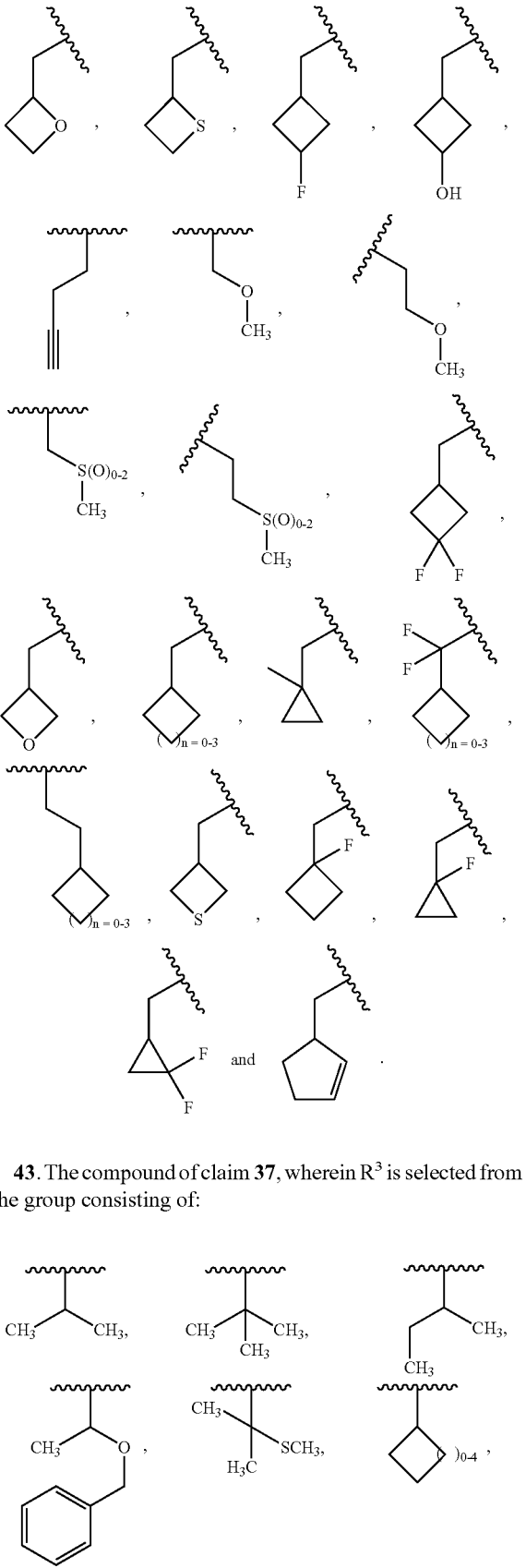

43. The compound of claim 37, wherein $R^3$ is selected from the group consisting of:

-continued
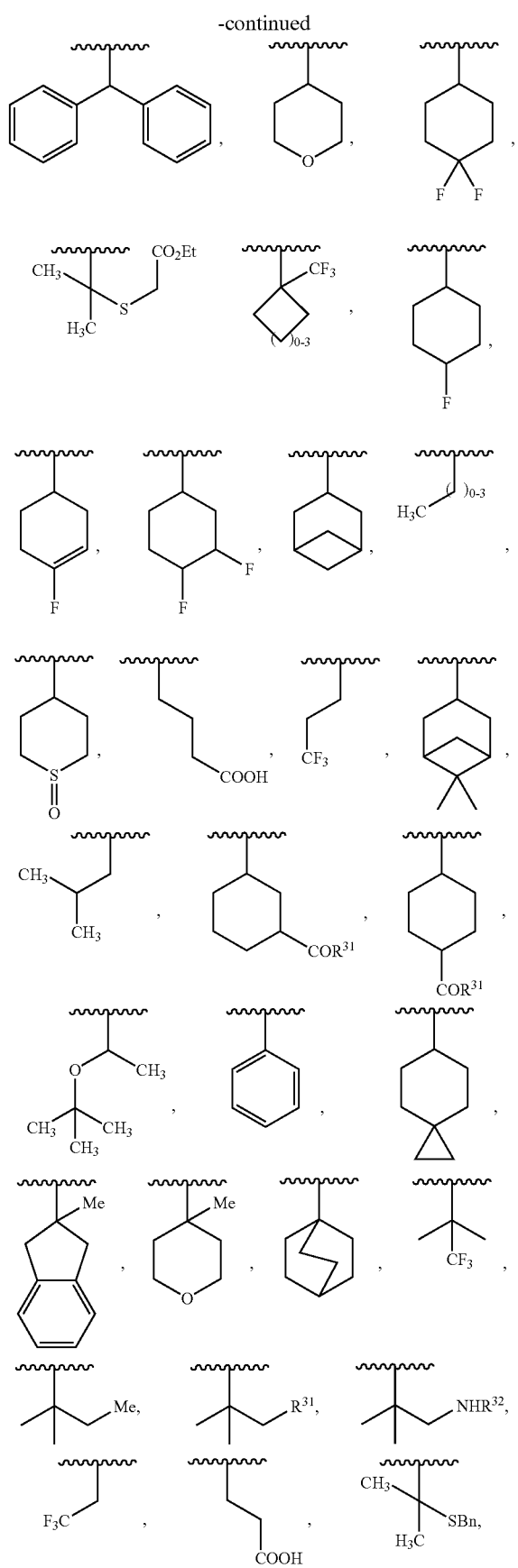
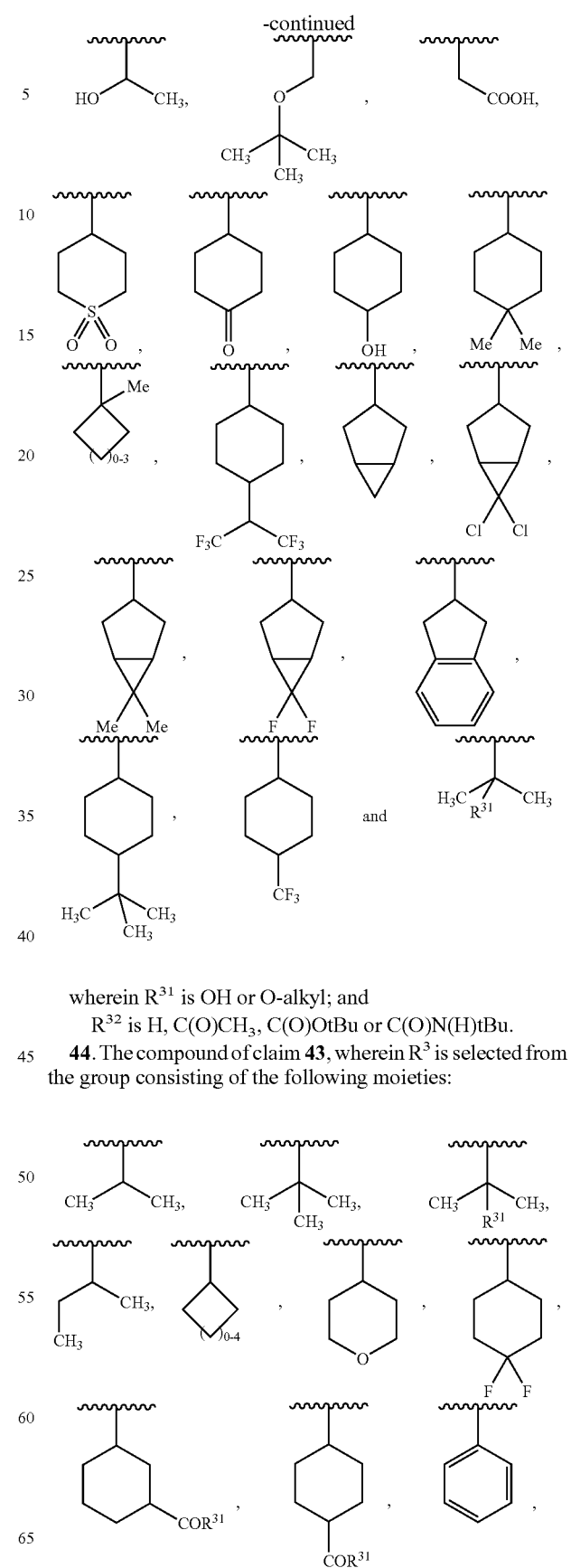
wherein $R^{31}$ is OH or O-alkyl; and
$R^{32}$ is H, C(O)CH$_3$, C(O)OtBu or C(O)N(H)tBu.
44. The compound of claim 43, wherein $R^3$ is selected from the group consisting of the following moieties:
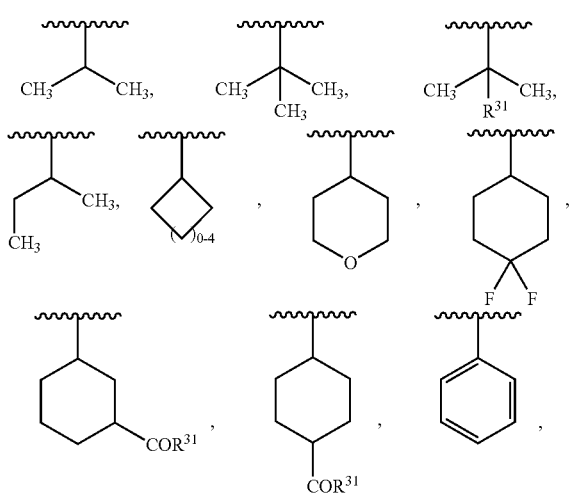

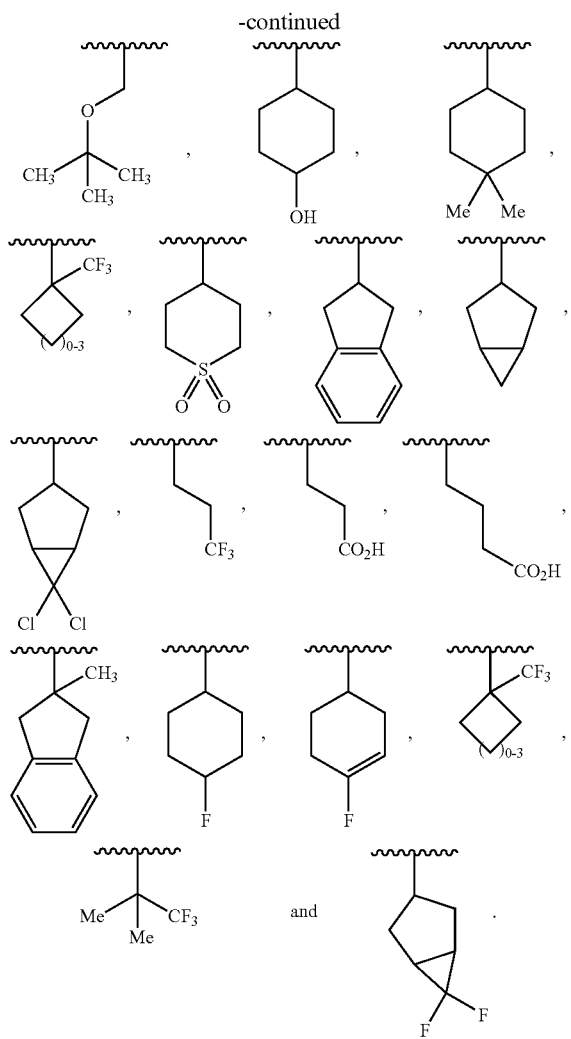
45. The compound of claim 37, wherein G is NH.
46. The compound of claim 37, wherein Y is selected from the following moieties:
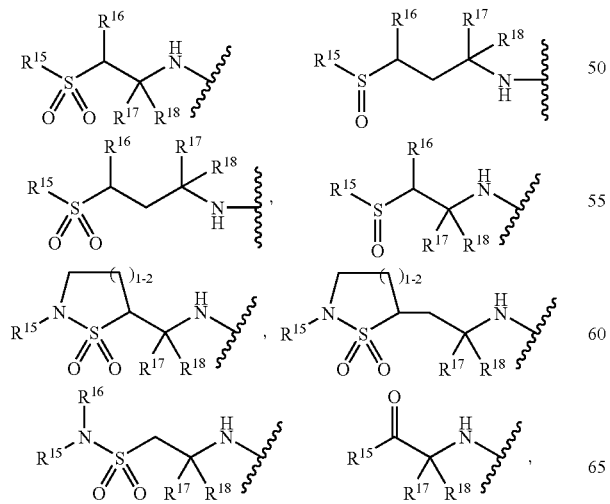
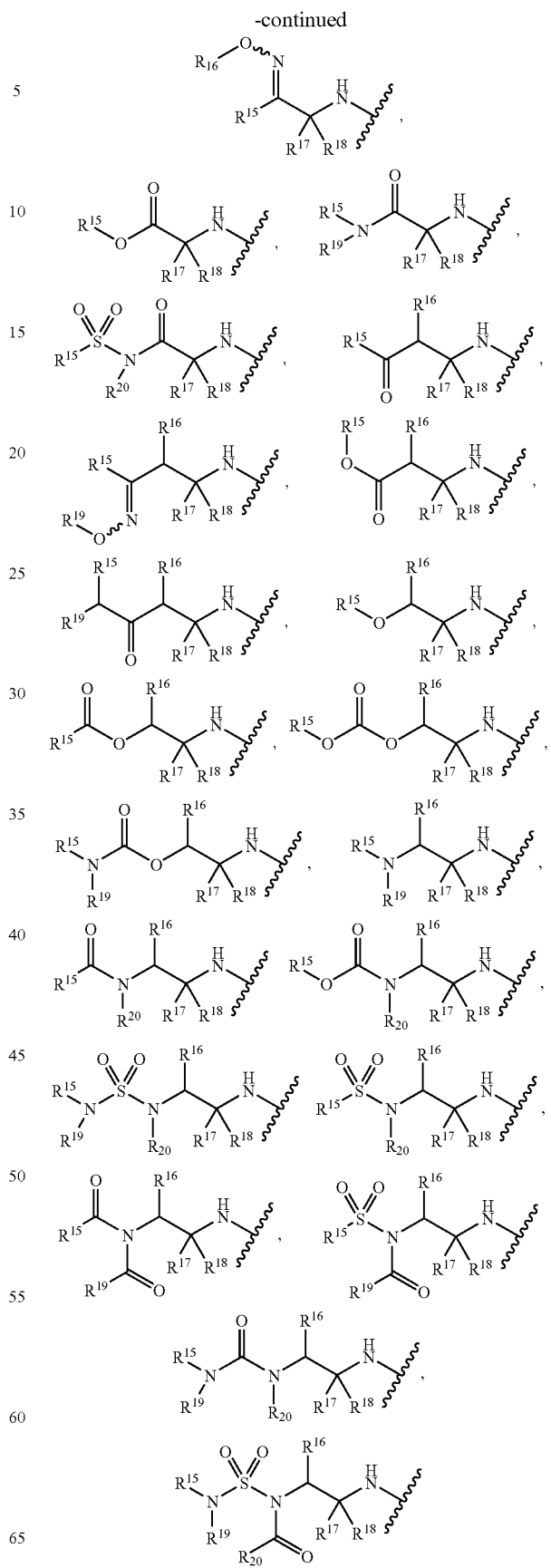

-continued

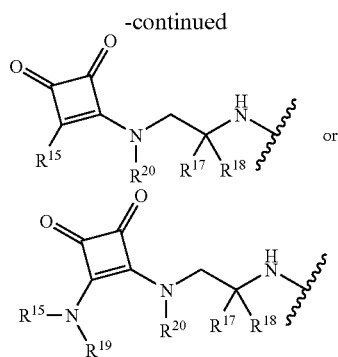

wherein $R^{15}$, $R^{16}$, $R^{17}$, $R^{18}$, $R^{19}$ and $R^{20}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, alkenyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

47. The compound of claim 46, wherein the moiety:

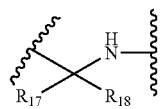

is selected from the following:

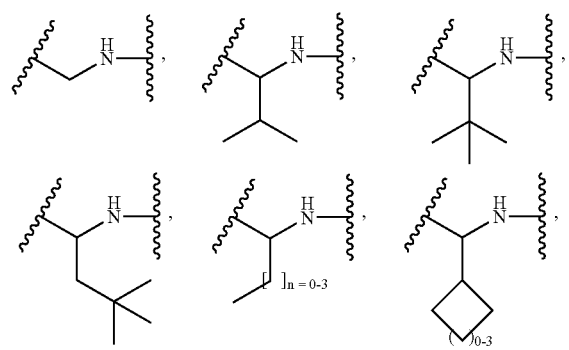

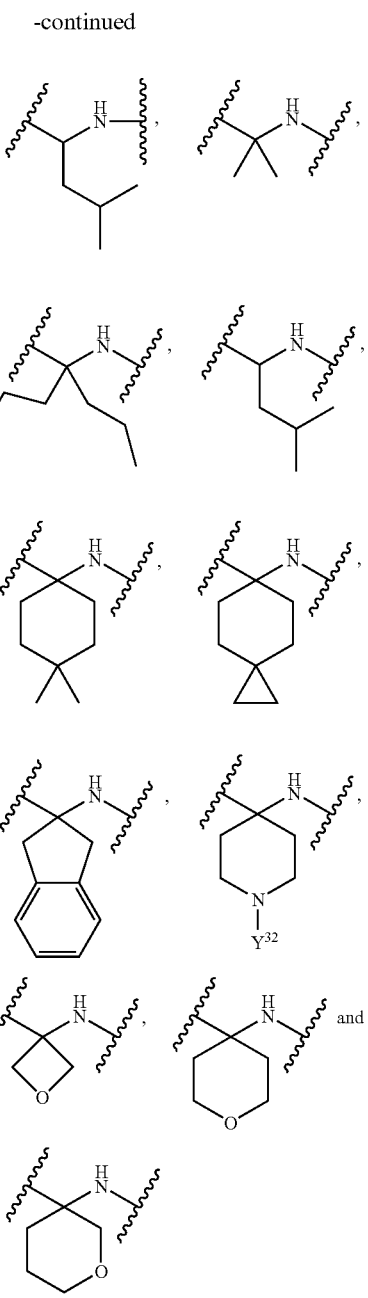

wherein $Y^{32}$ is selected from the group consisting of:

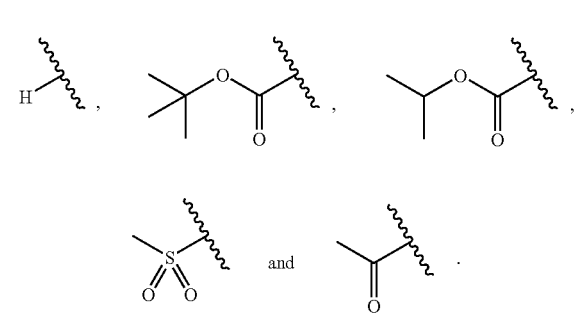

48. The compound of claim 37, wherein Y is selected from:
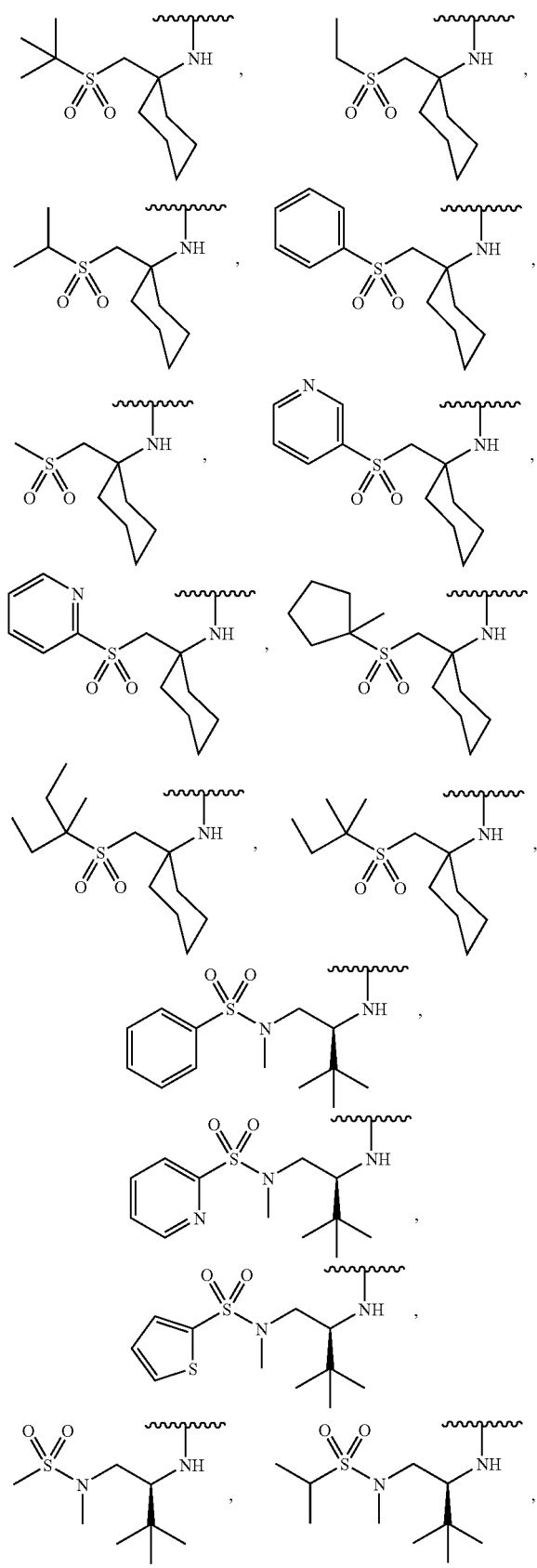
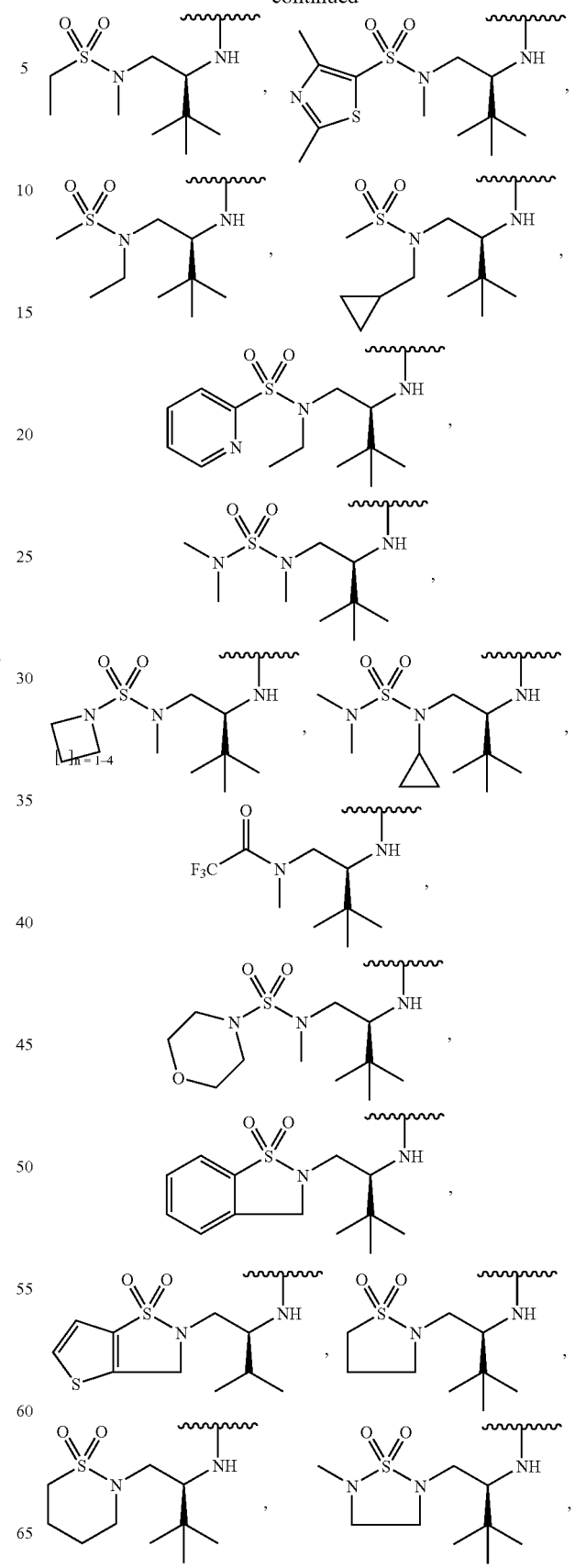

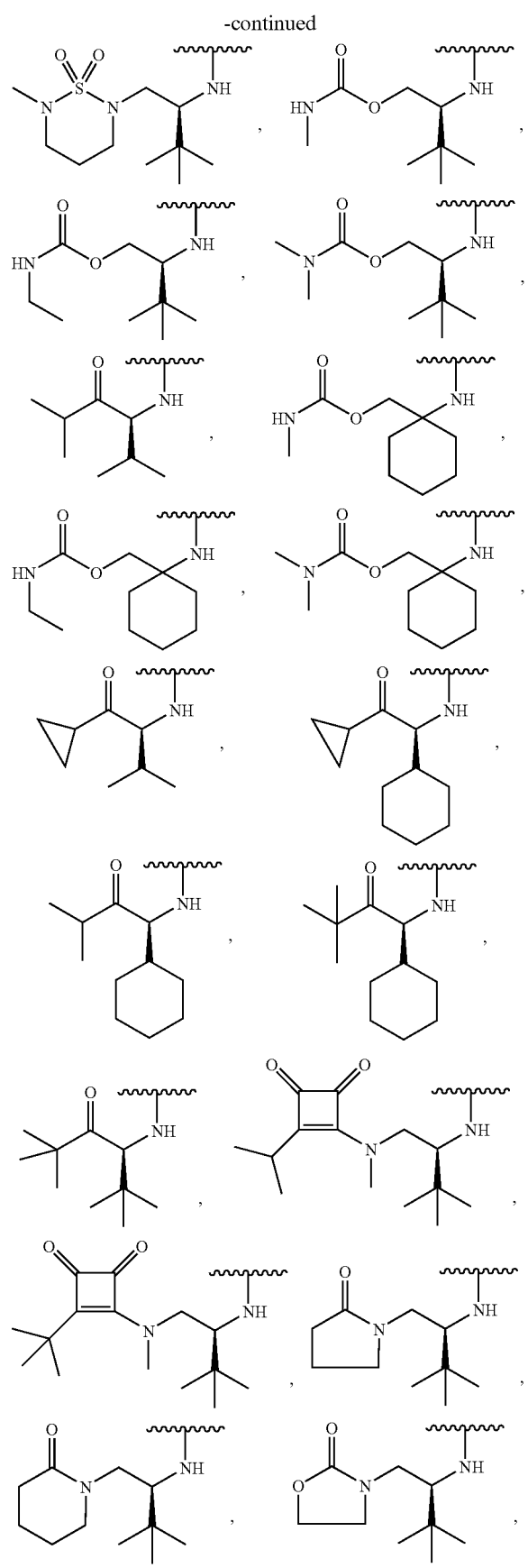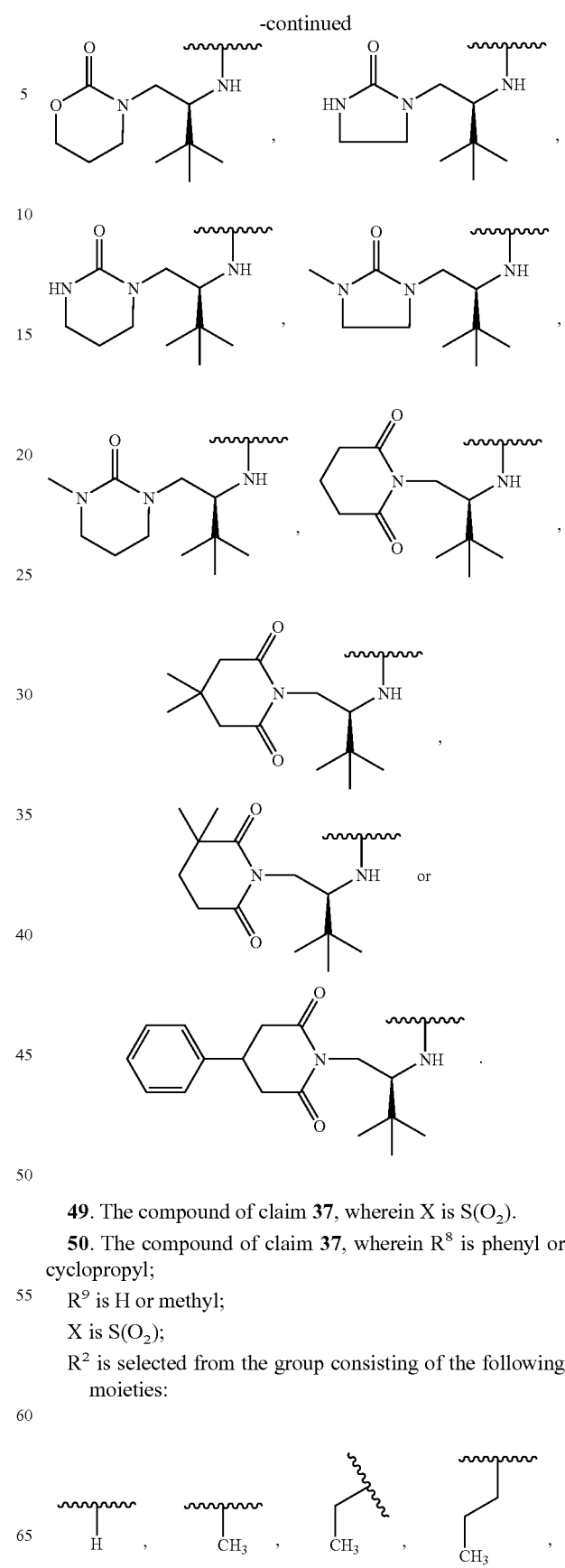
49. The compound of claim 37, wherein X is $S(O_2)$.
50. The compound of claim 37, wherein $R^8$ is phenyl or cyclopropyl;
$R^9$ is H or methyl;
X is $S(O_2)$;
$R^2$ is selected from the group consisting of the following moieties:
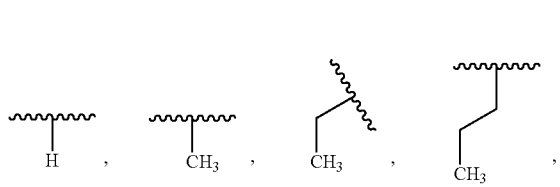

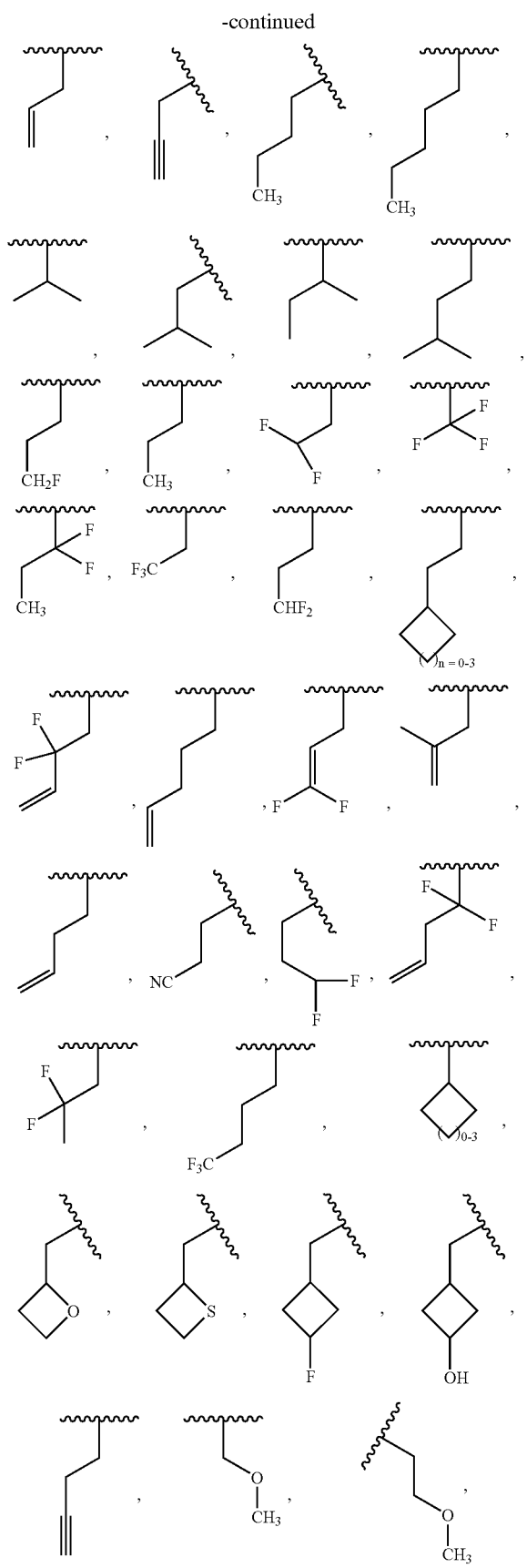
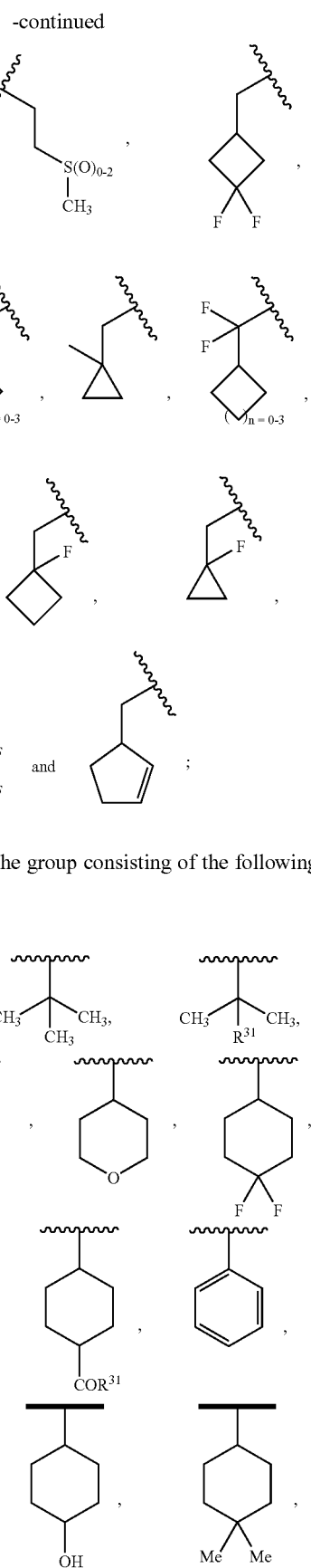
R³ is selected from the group consisting of the following moieties:

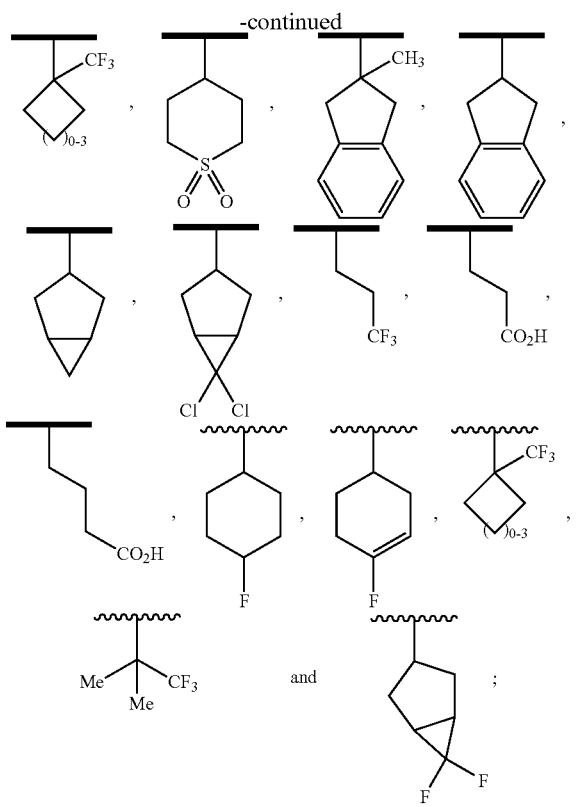
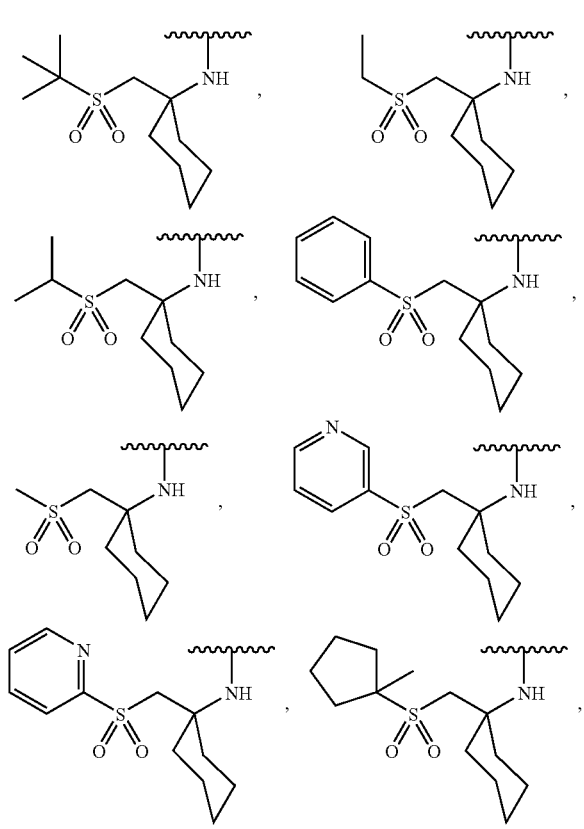
and Y is selected from:
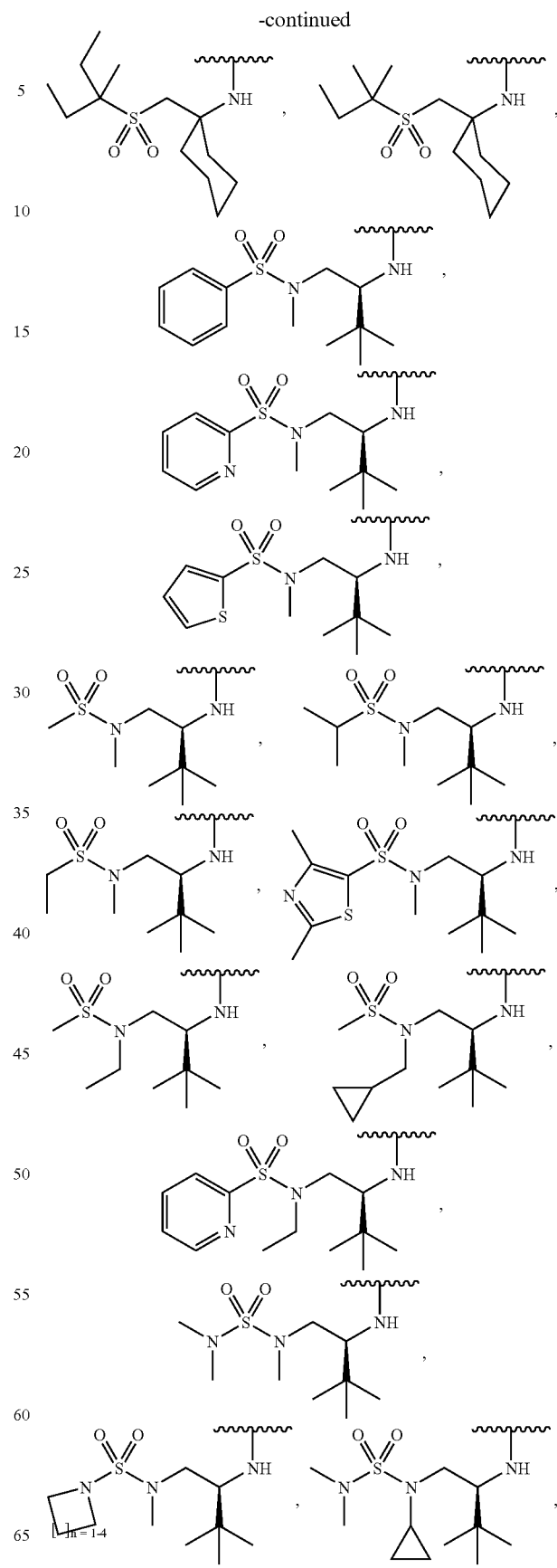

-continued
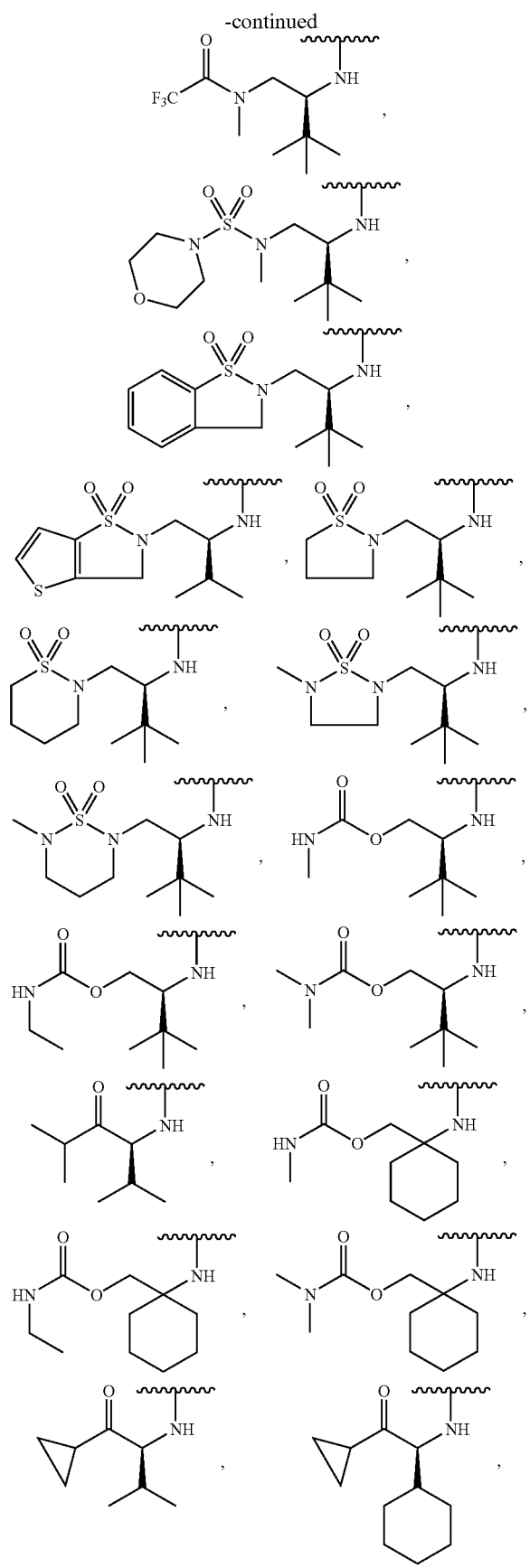
-continued
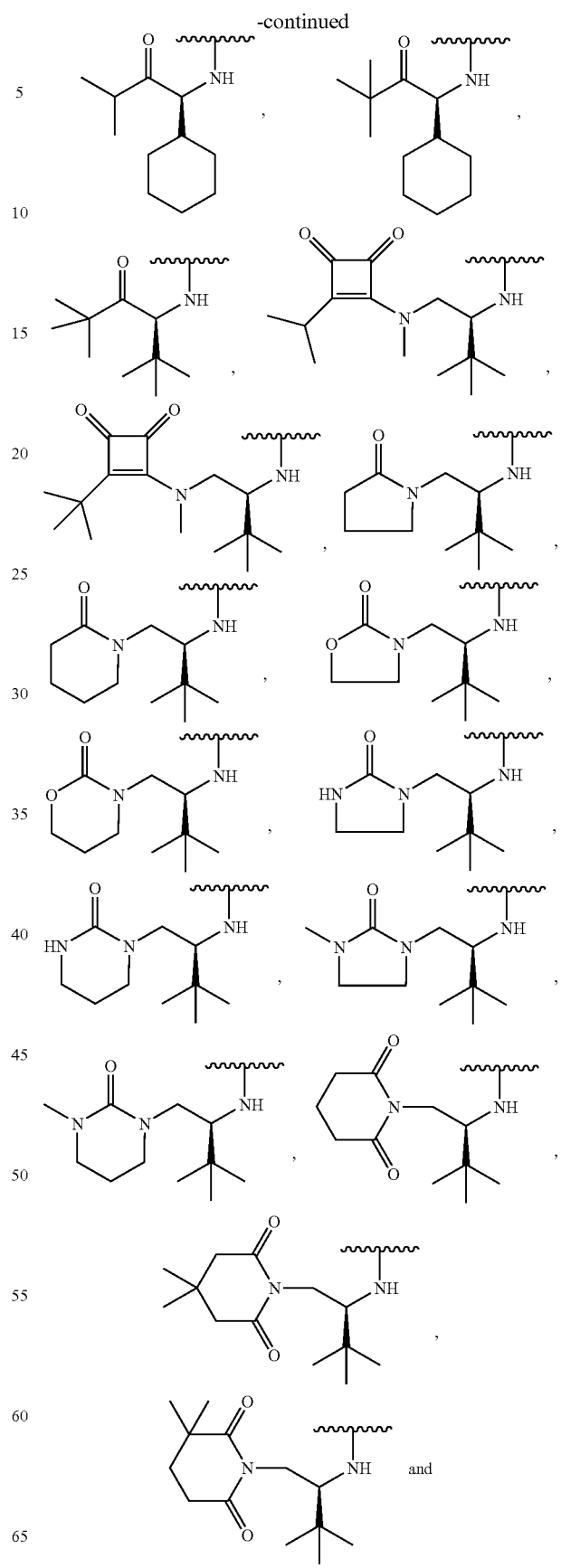

-continued

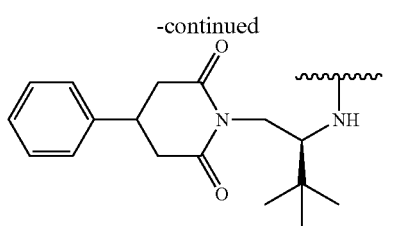

51. A pharmaceutical composition for treating a HCV infection, said composition comprising therapeutically effective amount of one or more compounds in claim 37 and a pharmaceutically acceptable carrier.

52. The pharmaceutical composition of claim 51, additionally containing at least one antiviral agent.

53. The pharmaceutical composition of claim 51, additionally containing at least one interferon or PEG-interferon alpha conjugate.

54. The pharmaceutical composition of claim 53, wherein said at least one antiviral agent is ribavirin and said at least one interferon is α-interferon or pegylated interferon.

55. A method of treatment of an infection of hepatitis C virus, comprising administering an effective amount of one or more compounds of claim 37 to a mammal in need thereof.

56. A method of treating or ameliorating one or more symptoms of hepatitis C, comprising administering a therapeutically effective amount of one or more compounds of claim 37 to a mammal in need thereof.

57. A compound of claim 37 in isolated and purified form.

* * * * *